US006826422B1

(12) United States Patent
Modell et al.

(10) Patent No.: US 6,826,422 B1
(45) Date of Patent: **\*Nov. 30, 2004**

(54) SPECTRAL VOLUME MICROPROBE ARRAYS

(75) Inventors: Mark Modell, Natick, MA (US); Ze'ev Hed, Nashua, NH (US); David Bee, Groton, MA (US); David Lipson, Newton, MA (US); Jennie Kwo, Cambridge, MA (US); Matthew Emans, Boston, MA (US); Robert Nordstrom, Hanover, MA (US)

(73) Assignee: MediSpectra, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/481,762
(22) Filed: Jan. 11, 2000

Related U.S. Application Data

(63) Continuation-in-part of application No. 09/241,806, filed on Feb. 2, 1999, now Pat. No. 6,411,835, and a continuation-in-part of application No. 08/782,936, filed on Jan. 13, 1997, now Pat. No. 6,104,945.
(60) Provisional application No. 60/115,373, filed on Jan. 11, 1999.

(51) Int. Cl.[7] .................................................. A61B 5/05
(52) U.S. Cl. ..................... 600/407; 600/473; 600/476; 250/461.2; 356/317
(58) Field of Search .......................... 600/121–125, 600/310, 407, 473, 475–479; 356/317, 318, 337, 341–343; 250/341.1, 363.01–363.02, 372, 458.1, 459.1, 461.1, 461.2

(56) References Cited

U.S. PATENT DOCUMENTS 3,013,467 A  12/1961  Minsky ........................ 88/14

(List continued on next page.)

FOREIGN PATENT DOCUMENTS

| EP | 0 135 134 | 3/1985 |
| EP | 0 280 418 | 8/1988 |

(List continued on next page.)

OTHER PUBLICATIONS

P. Davidovits et al. "Scanning Laser Microscope for Biological Investigations", Applied Optics, vol. 10, No. 7, pp. 1615–1619, Jul. 1971.

C.J.R. Sheppard et al. "Depth of Field in the Scanning Microscope", Optics Letters, vol. 3, No. 3, Sep. 1978, pp. 115–117.

(List continued on next page.)

Primary Examiner—Ruth S. Smith
(74) Attorney, Agent, or Firm—Testa, Hurwitz & Thibeault, LLP

(57) ABSTRACT

Methods and apparatus are provided for determining a characteristic of a sample of a material by the interaction of electromagnetic radiation with the sample. The apparatus includes an optical assembly and a protective barrier. The optical assembly sequentially illuminates a plurality of volume elements in the sample with an intensity distribution in the sample that drops off substantially monotonically from a first region in a first optical path and collects electromagnetic radiation emanating from each of the volume elements. The optical assembly collects the electromagnetic radiation emanating from each of the volume elements with a collected distribution that drops off substantially monotonically from a second region in a second optical path. The first and second regions at least partially overlap in each of the volume elements. The optical assembly can be configured as a probe, to be directed to the evaluation of a sample of a biological material. A protective barrier can be disposed between the optical assembly and a body tissue, to prevent contamination of the optical assembly by said body tissue.

14 Claims, 26 Drawing Sheets

U.S. PATENT DOCUMENTS

| | | |
|---|---|---|
| 3,632,865 A | 1/1972 | Haskell et al. .................. 178/6 |
| 3,809,072 A | 5/1974 | Ersek et al. ................... 128/23 |
| 3,890,462 A | 6/1975 | Limb et al. .................. 178/6.8 |
| 3,963,019 A | 6/1976 | Quandt et al. |
| D242,393 S | 11/1976 | Bauman |
| D242,396 S | 11/1976 | Bauman |
| D242,397 S | 11/1976 | Bauman |
| D242,398 S | 11/1976 | Bauman |
| 4,017,192 A | 4/1977 | Rosenthal et al. ........... 356/201 |
| 4,071,020 A | 1/1978 | Puglise et al. .................. 128/2 |
| 4,198,571 A | 4/1980 | Sheppard .................... 250/571 |
| 4,218,703 A | 8/1980 | Netravali et al. ........... 358/136 |
| 4,254,421 A | 3/1981 | Kreutel, Jr. ................. 343/754 |
| 4,273,110 A | 6/1981 | Groux ........................... 128/6 |
| 4,357,075 A | 11/1982 | Hunter ....................... 350/294 |
| 4,397,557 A | 8/1983 | Herwig et al. .............. 356/342 |
| 4,549,229 A | 10/1985 | Nakano et al. ................. 360/8 |
| 4,646,722 A | 3/1987 | Silverstein et al. ............ 128/4 |
| 4,662,360 A | 5/1987 | O'Hara et al. ................. 128/9 |
| 4,733,063 A | 3/1988 | Kimura et al. .............. 250/201 |
| 4,741,326 A | 5/1988 | Sidall et al. .................... 128/4 |
| 4,753,530 A | 6/1988 | Knight et al. ................. 356/73 |
| 4,768,513 A | 9/1988 | Suzuki ........................ 128/634 |
| 4,800,571 A | 1/1989 | Konishi ........................ 375/10 |
| 4,844,617 A | 7/1989 | Kelderman et al. ......... 356/372 |
| 4,845,352 A | 7/1989 | Benschop .................. 250/201 |
| 4,852,955 A | 8/1989 | Doyle et al. ................. 350/1.2 |
| 4,877,033 A | 10/1989 | Seitz, Jr. ................ 128/660.05 |
| 4,878,485 A | 11/1989 | Adair ............................ 128/6 |
| 4,891,829 A | 1/1990 | Deckman et al. .............. 378/4 |
| 4,930,516 A | 6/1990 | Alfano et al. ............... 128/665 |
| 4,945,478 A | 7/1990 | Merickel et al. ....... 364/413.22 |
| 4,965,441 A | 10/1990 | Picard .................... 250/201.3 |
| 4,972,258 A | 11/1990 | Wolf et al. .................... 358/93 |
| 4,974,580 A | 12/1990 | Anapliotis ..................... 128/4 |
| 4,979,498 A | 12/1990 | Oneda et al. .................. 128/6 |
| 4,997,242 A | 3/1991 | Amos ........................ 350/6.91 |
| 5,003,979 A | 4/1991 | Merickel et al. ....... 364/413.22 |
| 5,011,243 A | 4/1991 | Doyle et al. ................. 350/1.2 |
| 5,022,757 A | 6/1991 | Modell ....................... 356/318 |
| 5,028,802 A | 7/1991 | Webb et al. ................. 250/571 |
| 5,032,720 A | 7/1991 | White ......................... 250/236 |
| 5,034,613 A | 7/1991 | Denk et al. ............... 250/458.1 |
| 5,036,853 A | 8/1991 | Jeffcoat et al. .............. 128/634 |
| 5,042,494 A | 8/1991 | Alfano ....................... 128/665 |
| 5,048,946 A | 9/1991 | Sklar et al. ................. 351/206 |
| 5,054,926 A | 10/1991 | Dabbs et al. ................ 356/345 |
| 5,065,008 A | 11/1991 | Hakamata et al. .......... 250/216 |
| 5,071,246 A | 12/1991 | Blaha et al. ................. 351/221 |
| 5,074,306 A | 12/1991 | Green et al. ................. 128/664 |
| 5,083,220 A | 1/1992 | Hill ............................ 359/234 |
| 5,091,652 A | 2/1992 | Mathies et al. .......... 250/458.1 |
| 5,101,825 A | 4/1992 | Gravenstein et al. ....... 128/633 |
| 5,120,953 A | 6/1992 | Harris ...................... 250/227.2 |
| 5,122,653 A | 6/1992 | Ohki .......................... 250/216 |
| 5,132,526 A | 7/1992 | Iwasaki .................... 250/201.3 |
| 5,139,025 A | 8/1992 | Lewis et al. ................ 128/665 |
| 5,154,166 A | 10/1992 | Chikama ....................... 128/4 |
| 5,159,919 A | 11/1992 | Chikama ....................... 128/4 |
| 5,161,053 A | 11/1992 | Dabbs ........................ 359/384 |
| 5,162,641 A | 11/1992 | Fountain .................. 250/201.2 |
| 5,162,941 A | 11/1992 | Favro et al. ................. 359/386 |
| 5,168,157 A | 12/1992 | Kimura ....................... 250/234 |
| 5,192,980 A | 3/1993 | Dixon et al. ................ 356/326 |
| 5,193,525 A | 3/1993 | Silverstein et al. ............ 128/4 |
| RE34,214 E | 4/1993 | Carlsson et al. ............. 358/93 |
| 5,199,431 A | 4/1993 | Kittrell et al. ............... 128/634 |
| 5,201,318 A | 4/1993 | Rava et al. ................. 128/665 |
| 5,201,908 A | 4/1993 | Jones ............................ 128/4 |
| 5,203,328 A | 4/1993 | Samuels et al. ............. 128/633 |
| 5,225,671 A | 7/1993 | Fukuyama .................. 250/216 |
| 5,235,457 A | 8/1993 | Lichtman et al. ........... 359/368 |
| 5,237,984 A | 8/1993 | Williams, III et al. .......... 128/4 |
| 5,239,178 A | 8/1993 | Derndinger et al. ........ 250/234 |
| 5,248,876 A | 9/1993 | Kerstens et al. ............ 250/561 |
| 5,253,071 A | 10/1993 | MacKay ..................... 358/222 |
| 5,257,617 A | 11/1993 | Takahashi ...................... 128/4 |
| 5,260,569 A | 11/1993 | Kimura ....................... 250/234 |
| 5,260,578 A | 11/1993 | Bliton et al. .............. 250/461.1 |
| 5,261,410 A | 11/1993 | Afano et al. ................ 128/664 |
| 5,262,646 A | 11/1993 | Booker et al. .............. 250/341 |
| 5,274,240 A | 12/1993 | Mathies et al. .......... 250/458.1 |
| 5,284,149 A | 2/1994 | Dhadwal et al. ............ 128/665 |
| 5,286,964 A | 2/1994 | Fountain .................. 250/201.2 |
| 5,289,274 A | 2/1994 | Kondo ........................ 348/208 |
| 5,294,799 A | 3/1994 | Aslund et al. ............ 250/458.1 |
| 5,296,700 A | 3/1994 | Kumagai ..................... 250/216 |
| 5,303,026 A | 4/1994 | Strobl et al. ................ 356/318 |
| 5,306,902 A | 4/1994 | Goodman ................. 250/201.3 |
| 5,313,567 A | 5/1994 | Civanlar et al. ............. 395/124 |
| 5,319,200 A | 6/1994 | Rosenthal et al. .......... 250/341 |
| 5,321,501 A | 6/1994 | Swanson et al. |
| 5,324,979 A | 6/1994 | Rosenthal ............... 250/504 R |
| 5,325,846 A | 7/1994 | Szabo ............................ 128/4 |
| 5,329,352 A | 7/1994 | Jacobsen .................... 356/301 |
| 5,337,734 A | 8/1994 | Saab ............................. 128/4 |
| 5,343,038 A | 8/1994 | Nishiwaki et al. .......... 250/234 |
| 5,345,306 A | 9/1994 | Ichimura et al. ............ 356/346 |
| 5,345,941 A | 9/1994 | Rava et al. ................. 128/665 |
| 5,349,961 A | 9/1994 | Stoddart et al. ............. 128/665 |
| 5,398,685 A | 3/1995 | Wilk et al. ................ 128/653.1 |
| 5,402,768 A | 4/1995 | Adair ............................ 128/4 |
| 5,406,939 A | 4/1995 | Bala |
| 5,413,092 A | 5/1995 | Williams, III et al. .......... 128/4 |
| 5,413,108 A | 5/1995 | Alfano ....................... 128/665 |
| 5,415,157 A | 5/1995 | Welcome ....................... 128/4 |
| 5,418,797 A | 5/1995 | Bashkansky et al. .......... 372/3 |
| 5,419,311 A | 5/1995 | Yabe et al. ..................... 128/4 |
| 5,419,323 A | 5/1995 | Kittrell et al. ............... 128/653 |
| 5,421,337 A | 6/1995 | Richards-Kortum et al. ............. 128/665 |
| 5,421,339 A | 6/1995 | Ramanujam et al. ....... 128/665 |
| 5,424,543 A | 6/1995 | Dombrowski et al. ...... 250/330 |
| 5,450,857 A | 9/1995 | Garfield et al. ............. 128/778 |
| 5,451,931 A | 9/1995 | Muller et al. ................ 340/630 |
| 5,458,132 A | 10/1995 | Yabe et al. ..................... 128/4 |
| 5,458,133 A | 10/1995 | Yabe et al. .................. 600/121 |
| 5,467,767 A | 11/1995 | Alfano et al. ............... 128/665 |
| 5,469,853 A | 11/1995 | Law et al. ............. 128/662.06 |
| 5,477,382 A | 12/1995 | Pernick ....................... 359/559 |
| 5,480,775 A | 1/1996 | Ito et al. ....................... 435/7.2 |
| 5,493,444 A | 2/1996 | Khoury et al. .............. 359/559 |
| 5,496,259 A | 3/1996 | Perkins ....................... 600/124 |
| 5,507,295 A | 4/1996 | Skidmore .................... 600/121 |
| 5,516,010 A | 5/1996 | O'Hara et al. .............. 600/122 |
| 5,519,545 A | 5/1996 | Kawahara ..................... 360/46 |
| 5,529,235 A | 6/1996 | Bolarski et al. .......... 227/175.1 |
| 5,536,236 A | 7/1996 | Yabe et al. .................. 600/125 |
| 5,545,121 A | 8/1996 | Yabe et al. .................. 600/121 |
| 5,551,945 A | 9/1996 | Yabe et al. .................. 600/122 |
| 5,556,367 A | 9/1996 | Yabe et al. .................. 600/124 |
| 5,562,100 A | 10/1996 | Kittrell et al. ............... 128/665 |
| 5,579,773 A | 12/1996 | Vo-Dinh et al. ............. 128/665 |
| 5,582,168 A | 12/1996 | Samuels et al. ............. 128/633 |
| 5,587,832 A | 12/1996 | Krause ....................... 359/385 |
| 5,596,992 A | 1/1997 | Haaland et al. ............. 128/664 |
| 5,599,717 A | 2/1997 | Vo-Dinh ....................... 436/63 |
| 5,609,560 A | 3/1997 | Ichikawa et al. ............ 600/101 |
| 5,612,540 A | 3/1997 | Richards-Korum et al. ............. 250/461.2 |
| 5,623,932 A | 4/1997 | Ramanujam et al. ....... 128/665 |

| | | | |
|---|---|---|---|
| 5,647,368 A | 7/1997 | Zeng et al. .................. 128/665 |
| 5,662,588 A | 9/1997 | Lida ........................... 600/121 |
| 5,685,822 A | 11/1997 | Harhen ....................... 600/125 |
| 5,693,043 A | 12/1997 | Kittrell et al. ................ 606/15 |
| 5,695,448 A | 12/1997 | Kimura et al. .............. 600/121 |
| 5,697,373 A | 12/1997 | Richards-Kortum et al. ............. 128/664 |
| 5,699,795 A | 12/1997 | Richards-Kortum ..................... 128/634 |
| 5,704,892 A | 1/1998 | Adair ......................... 600/121 |
| 5,707,343 A | 1/1998 | O'Hara et al. .............. 600/121 |
| 5,713,364 A | 2/1998 | DeBaryshe et al. |
| 5,717,209 A | 2/1998 | Bigman et al. ......... 250/339.12 |
| 5,730,701 A | 3/1998 | Furukawa et al. .......... 600/127 |
| 5,733,244 A | 3/1998 | Yasui et al. .................. 600/127 |
| 5,735,276 A | 4/1998 | Lemelson et al. .......... 128/653 |
| 5,746,695 A | 5/1998 | Yasui et al. .................. 600/127 |
| 5,768,333 A | 6/1998 | Abdel-Mottaleb ........... 378/37 |
| 5,769,792 A | 6/1998 | Palcic et al. ................ 600/477 |
| 5,773,835 A | 6/1998 | Sinofsky et al. ......... 250/462.1 |
| 5,791,346 A | 8/1998 | Craine et al. ............... 128/653 |
| 5,795,632 A | 8/1998 | Buchalter .................. 428/35.2 |
| 5,800,350 A | 9/1998 | Coppleson et al. ......... 600/372 |
| 5,807,248 A | 9/1998 | Mills .......................... 600/322 |
| 5,813,987 A | 9/1998 | Modell et al. .............. 600/473 |
| 5,817,015 A | 10/1998 | Adair ......................... 600/121 |
| 5,830,146 A | 11/1998 | Skladnev et al. ........... 600/478 |
| 5,833,617 A | 11/1998 | Hayashi ..................... 600/476 |
| 5,840,035 A | 11/1998 | Heusmann et al. ........... 600/47 |
| 5,842,995 A | 12/1998 | Mahadevan-Jansen et al. ............... 600/473 |
| 5,855,551 A | 1/1999 | Sklandnev et al. |
| 5,860,913 A | 1/1999 | Yamaya et al. ............. 600/127 |
| 5,863,287 A | 1/1999 | Segawa ...................... 600/121 |
| 5,865,726 A | 2/1999 | Katsurada et al. .......... 600/127 |
| 5,876,329 A | 3/1999 | Harhen ....................... 600/125 |
| 5,920,399 A | 7/1999 | Sandison et al. ........... 356/418 |
| 5,921,926 A | 7/1999 | Rolland et al. ............. 600/407 |
| 5,929,985 A | 7/1999 | Sandison et al. ........... 365/318 |
| 5,931,779 A | 8/1999 | Arakaki et al. ............. 600/310 |
| 5,938,617 A | 8/1999 | Vo-Dinh ..................... 600/476 |
| 5,941,834 A | 8/1999 | Skladnev et al. ........... 600/587 |
| 5,983,125 A | 11/1999 | Alfano et al. ............... 600/473 |
| 5,989,184 A | 11/1999 | Blair et al. ................. 600/167 |
| 5,991,653 A | 11/1999 | Richards-Kortum et al. ............. 660/475 |
| 6,021,344 A | 2/2000 | Lui et al. .................... 600/476 |
| 6,069,689 A | 5/2000 | Zeng et al. .................. 356/773 |
| 6,091,985 A | 7/2000 | Alfano et al. ............... 600/476 |
| 6,095,982 A | 8/2000 | Richards-Kortum et al. ............. 600/476 |
| 6,096,065 A | 8/2000 | Crowley ...................... 607/88 |
| 6,099,464 A | 8/2000 | Shimizu et al. ............. 600/104 |
| 6,104,945 A * | 8/2000 | Modell et al. .............. 600/473 |
| 6,119,031 A | 9/2000 | Crowley ..................... 600/407 |
| 6,124,597 A | 9/2000 | Shehada et al. ......... 250/461.2 |
| 6,146,897 A | 11/2000 | Cohenford et al. ............ 436/63 |
| 6,169,817 B1 | 1/2001 | Parker et al. ............... 382/131 |
| 6,208,887 B1 | 3/2001 | Clarke et al. ............... 600/476 |
| 6,241,662 B1 | 6/2001 | Richards-Kortum et al. ............. 600/310 |
| 6,243,601 B1 | 6/2001 | Wist ........................... 600/473 |
| 6,246,471 B1 | 6/2001 | Jung et al. .................... 356/73 |
| 6,246,479 B1 | 6/2001 | Jung et al. .................. 356/419 |
| 6,285,639 B1 | 9/2001 | Maenza et al. ........... 369/47.28 |
| D453,832 S | 2/2002 | Morrell et al. ............. D24/138 |
| D453,962 S | 2/2002 | Morrell et al. ............. D24/138 |
| D453,963 S | 2/2002 | Morrell et al. ............. D24/138 |
| D453,964 S | 2/2002 | Morrell et al. ............. D24/138 |
| 6,377,842 B1 | 4/2002 | Pogue et al. ................ 600/478 |
| 6,385,484 B2 | 5/2002 | Nordstrom et al. .......... 600/476 |
| 6,411,835 B1 * | 6/2002 | Modell et al. .............. 600/407 |
| 6,411,838 B1 | 6/2002 | Nordstrom et al. ......... 600/476 |
| D460,821 S | 7/2002 | Morrell et al. ............. D24/138 |
| 6,421,553 B1 | 7/2002 | Costa et al. ................ 600/476 |
| 6,427,082 B1 | 7/2002 | Nordstrom et al. ......... 600/476 |
| 6,571,118 B1 | 5/2003 | Utzinger et al. ............ 600/476 |
| 6,574,502 B2 | 6/2003 | Hayashi ..................... 600/476 |
| 2002/0007123 A1 | 1/2002 | Balas et al. ................. 600/476 |

FOREIGN PATENT DOCUMENTS

| | | |
|---|---|---|
| EP | 0 335 725 | 10/1989 |
| EP | 0 444 689 A2 | 9/1991 |
| EP | 0 474 264 | 3/1992 |
| EP | 0 641 542 | 3/1995 |
| EP | 0 689 045 | 12/1995 |
| EP | 0 737 849 A2 | 10/1996 |
| JP | 08-280602 | 10/1996 |
| SU | 1 223 092 | 4/1986 |
| WO | WO 92/19148 | 11/1992 |
| WO | WO 93/14688 | 8/1993 |
| WO | WO 94/26168 | 11/1994 |
| WO | 95/00067 | 1/1995 |
| WO | 95/04385 | 2/1995 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/59366 | 10/2000 |

OTHER PUBLICATIONS

C.J. Koester, "Scanning Mirror Microscope with Optical Sectioning Characteristics: Applications in Ophthalmology", Applied Optics. vol. 19, No. 11, Jun. 1980, pp. 1749–1757.

Jeffrey W. Hall, et al. "Near–Infrared Spectrophotometry: A New Dimension in Clinical Chemistry", Clin. Chem 38/9, 1623–1631 (1992).

Kevin T. Schomacker, et al. "Ultraviolet Laser–Induced Fluorescence of Colonic Tissue; Basic Biology and Diagnostic Potential", Lasers in Surgery and Medicine, 12: 63–78, (1992).

S. Schwartz, "Real–time laser–scanning Confocal ratio imaging", American Laboratory, pp. 53–62 Apr. 1993.

R. Richards–Kortum et al. Description and Performance of a Fiber–optic Confocal Fluorescence Spectrometer, Applied Spectroscopy, vol. 48, No. 3 pp. 350–355. (1994).

J.M. Schmitt et al. "Interferometric Versus Confocal Techniques for Imaging Microstructures in Turbid Biological Media", Proc. SPIE, 2135 (1994), pp. 1–12.

N. Ramanujam et al. Fluorescence Spectroscopy; A Diagnostic Tool for Cervical Intraepithelial Neoplasia (CIN), Gynecologic Oncology 52, pp. 31–38 (1994).

S.G. Anderson, "Confocal Laser Microscopes See A Wider Field of Application", Laser Focus World, pp. 83–86, Feb. 1994.

J.M. Schmitt et al. "Confocal Microscopy in Turbid Media", J. Opt. Soc. Am., vol. 11, pp. 2225–2235, Aug. 1994.

N. Ramanujam et al. "In vivo diagnosis of cervical intraepithelial neoplasia using 337–nm–excited laser–induced fluorescence", Pro. Natl. Acad. Sci. USA, vol. 91, pp. 10193–10197, Oct. 1994.

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

Althof et al. (1997), "A rapid and automatic image registration algorithm with subpixel accuracy," *IEEE Transactions on Medical Imaging*, 16(3):308–316.

Aström et al. (1999), "Motion estimation in image sequences using the deformation of apparent contours," *IEEE Transactions on Pattern Analysis and Machine Intelligence*, 21(2):114–127.

Balas (1997), "An Imaging Colorimeter for Noncontact Tissue Color Mapping," *IEEE Transactions on Biomedical Engineering*, 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96–104.

Balas et al. (1997), "A modular diffuse reflection and fluorescence emission imaging colorimeter for the in–vivo study of parameters related with the phototoxic effect in PDT," *SPIE*, 3191:50–57.

Balas et al. (1998), "In Vivo Assessment of Acetic Acid–Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm, Sweden, *SPIE*, vol. 3568:31–37.

Balas et al. (1999), "In Vivo Detection and Staging of Epithelial Dysplasias and Malignancies Based on the Quantitative Assessment of Acetic Acid–Tissue Interaction Kinetics," *Journal of Photochemistry and Photobiology B: Biology*, 53:153–157.

Bessey et al. (1949), "The Fluorometric measurement of the nucleotides of riboflavin and their concentration in tissues," *J. Biol.–Chem.*: 180:755–769.

Bors et al. (1998), "Optical flow estimation and moving object segmentation based on median radial basis function network," *IEEE Transactions on Image Processing*, 7(5):693–702.

Bouthemy et al. (1999), "A unified approach to shot change detection and camera motion characterization," *IEEE Transactions on Circuits and Systems for Video Technology*, 9(7):1030–1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.*, 62:84R–101R.

Camus et al. (1997), "Real–time quantized optical flow," *Real–Time Imaging*, 3:71–86.

Caplier et al. (1998), "Real–time implementation of a MRF–based motion detection algorithm," *Real–Time Imaging*, 4:41–54.

Contini et al. (1989), "Colposcopy and Computer Graphics: a New Method?" *Amer. J. Obstet. Gynecol.*, 160(3):535–538.

Craine et al. (1993), "Digital Imaging Colposcopy: basic concepts and applications," *Amer. J. Obstet. Gynecol.*, 82(5):869–873.

Craine et al. (1998), "Digital imaging colposcopy: Corrected area measurements using shape–from–shading," *IEEE Transactions on Medical Imaging*, 17(6):1003–1010.

Crisp et al. (1990), "The Computerized Digital Imaging Colposcope: Future Directions," *Amer. J. Obstet. Gynecol.*, 162(6):1491–1497.

Cronjé et al. (1997), "Effects of Dilute Acetic Acid on the Cervical Smear," *Acta. Cytol.*, 41:1091–1094.

Dickman et al. (2001), "Identification of Cervical Neoplasia Using a Simulation of Human Vision," *Journal of Lower Genital Tract Disease*, 5(3):144–152.

Drezek et al. (1999), "Light scattering from cells: finite–difference time–domain simulations and goniometric measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.*, 182(5):1135–1139.

Dumontier et al. (1999), "Real–time DSP implementation for MRF–based vidoe motion detection," *IEEE Transactions on Image Processing*, 8(10):1341–1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927–932.

Edebiri, A.A. (1990), "The relative significance of colposcopic discriptive appearances in the dianosis of cervical intraepithelial neoplasia," *Int. J. Gynecol. Obstet.*, 33:23–29.

Eisner et al. (1987), "Use of Cross–Correlation Function to Detect Patient Motion During Spectral Imaging," *Journal of Nuclear Medicine*, 28(1):97–101.

Ferris et al. (1998), "Colposcopy Quality Control: Establishing Colposcopy Criterion Standards for the NCI ALTS Trial Using Cervigrams," *J. Lower Genital Tract Disease*, 2(4):195–203.

Fleet et al. (1995), "Recursive Filters for Optical Flow," *IEEE Transactions on Pattern Analysis and Machine Intelligence*, 17(1):61–67.

Gao et al. (1998), "A work minimization approach to image morphing," *The Visual Computer*, 14:390–400.

Gauch (1999), "Image Segmentation and Analysis Via Multiscale Gradient Watershed Hierarchies," *IEEE Transactions on Image Processing*, 8(1):69–79.

Haralick (1984), "Digital Step Edges from Zero Crossing of Second Directional Derivatives," *IEEE Transactions on Pattern Analysis and Machine Intelligence*, 6(1):58–68.

Haris et al. (1998), "Hybrid Image Segmentation Using Watersheds and Fast Region Merging," *IEEE Transactions on Image Processing*, 7(12):1684–1699.

Helmerhorst et al. (1987), "The accuracy of colposcopically directed biopsy in diagnosis of CIN 2/3." *Eur. J. Obstet. Gyn. Reprod. Biol.*, 24, 221–229.

Horn et al. (1993), "Determining Optical Flow": a retrospective, *Artificial Intelligence*, 59:81–87.

Horn et al. (1981), "Determining Optical Flow," *Artificial Intelligence*, 17(1–3):185–203.

Huang et al. (1979), "A fast two–dimensional median filtering algorithm," *IEEE Transactions on Acoustics, Speech, and Signal Processing*, 27(1):13–18.

Jackway (1996), "Gradient Watersheds in Morphological Scale–Space," *IEEE Transactions on Image Processing*, 5(6):913–921.

Ji et al. (2000), "Texture Analysis for Classification of Cervix Lesions," *IEEE Transactions on Medical Imaging*, 19(11):1144–1149.

Kierkegaard et al. (1995), "Association between Colposcopic Findings and Histology in Cervical Lesions: The Significance of the Size of the Lesion" *Gynecologic Oncology*, 57:66–71.

Kumar et al. (1996), "Optical Flow: A Curve Evolution Approach," *IEEE Transactions on Image Processing*, 5(4):598–610.

Linde et al. (1980), An algorithm for vector quantizer design,: *IEEE Transactions on Communications*, 28(1):84–95.

MacAulay et al. (2002), "Variation of fluorescence spectroscopy during the menstrual cycle," *Optics Express*, 10(12):493–504.

MacLean A.B. (1999), "What is Acetowhite Epithelium," *Abstract Book: 10$^{th}$ World Congress of Cervical Pathology and Colposcopy, Nov. 7–11*, Buenos Aires, Argentina 41.

Marzetta et al. (1999), "A surprising radon transform result and its application to motion detection," *IEEE Transactions on Image Processing*, 8(8):1039–1049.

Miike et al. (1999), "Motion enhancement for preprocessing of optical flow and scientific visualization," *Pattern Recognition Letters*, 20:451–461.

Mikhail et al. (1995), "Computerized colposcopy and conservative management of cervical intraepithelial neoplasia in pregnancy," *Acta Obstet. Gynecol. Scand.*, 74:376–378.

Milanfar (1999), "Two–dimensional matched filtering for motion estimation," *IEEE Transactions on Image Processing*, 8(3):438–444.

Mitchell et al. (1998), "Colposcopy for the diagnosis of squamous intraepithelial lesions: a meta–analysis," *Obstet Gynecol.*, 91(4):626–631.

Mycek et al. (1998), "Colonic polyp differentiation using time–resolved autofluorescence spectroscopy," *Gastrointestinal Endoscopy*, 48(4):390–394.

Nanda et al. (2000), "Accuracy of the Papanicolaou test in screening for and follow–up of cervical cytologic abnormalities: a systematic review," *Ann Intern Med.*, 132(10):810–819.

Nesi et al. (1998), "RETIMAC REalTIme Motion Analysis Chip," *IEEE Transactions on Circuits and Systems–II: Analog and Digital Signal Processing*, 45(3):361–375.

Noumeir et al. (1996), "Detection of Motion During Tomographic Acquisition by an Optical Flow Algorithm," *Computers and Biomedical Research*, 29(1):1–15.

O'Sullivan et al. (1994), "Interobserver variation in the diagnostic and grading of dyskaryosis in cervical smears: specialist cytopathologists compared with non–specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):119–131.

Pan et al. (1998), "Correlation–feedback Technique in Optical Flow Determination," *IEEE Transactions on Image Processing*, 7(7):1061–1067.

Perona et al. (1990), "Scale–space and edge detection using anisotropic diffusion," *IEEE Transactions on Pattern Analysis and Machine Intelligence*, 12(7):629–639.

Pogue et al. (2001), "Analysis of Acetic Acid–Induced Whitening of High–Grade Squamous Intraepithelial Lesions," *Journal of Biomedical Optics*, 6(4):397–403.

Radjadhyaksha et al. (2000), "Confocal microscopy of excised human skin using acetic acid and crossed polarization: rapid detection of non–melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Reid et al. (1985), "Genital warts and cervical cancer. VII. An improved colposcopic index for differentiating benign papillomaviral infections from high–grade CIN," *Am. J. Obstet. Gynecol.*, 153(6):611–618.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantitative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164–171.

Schomacker et al. (1992), "Ultraviolet Laser–Induced Fluorescence of Colonic Polyps," *Gastroenterology*, 102:1155–1160.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three–dimensional medical image sequences," *IEEE Transactions on Medial Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence*, 13(6):583–598.

Vincent et al. (1993), "Morphological grayscale reconstruction in image analysis: Applications and efficient algorithms," *IEEE Transactions on Image Processing*, 2(2):176–201.

Wang et al. (1999), "Fast algorithms for the estimation of motion vectors," *IEEE Transactions on Image Processing*, 8(3):435–438.

Weng et al. (1997), "Three–Dimensional Surface Reconstruction Using Optical Flow for Medical Imaging," *IEEE Transactions on Medical Imaging*, 16(5):630–641.

Wolberg et al. (1998), "Image morphing: a survey," *The Visual Computer*, 14:360–372.

You et al. (1996), "Behavioral analysis of anisotropic diffusion in image processing," *IEEE Transactions on Image Processing*, 5(11):1539–1553.

Zahm et al. (1998), "Colposcopic appearance of cervical intraepithelial neoplasia is age dependent," *Am. J. Obstet. Gynecol.*, 179(5):1298–1304.

Zeger et al. (1992), "Globally optimal vector quantizer design by stochastic relaxation," *IEEE Transactions on Signal Processing*, 40(2):310–322.

Zeng et al. (1993), "A computerized autofluorescence and diffuse reflectance spectroanalyser system for in vivo skin studies," *Phys. Med. Biol.*, 38:231–240.

Zeng et al. (1997), "Optimization of fast block motion estimation algorithms," *IEEE Transactions on Circuits and Systems for Video Technology*, 7(6):833–844.

Zhang et al. (1999), "Shape from shading: a survey," *IEEE Transactions on Pattern Analysis and Machine Intelligence*, 21(8):690–706.

Zheng et al. (1991), "Estimation of illumination direction, albedo, and shape from shading," *IEEE Transactions on Pattern Analysis and Machine Intelligence*, 13(7):680–702.

Zhengfang et al. (1998), "Identification of Colonic Dysplasia and Neoplasia by Diffuse Reflectance Spectroscopy and Pattern Recognition Techniques," *Applied Spectroscopy*, 52(6):833–839.

\* cited by examiner

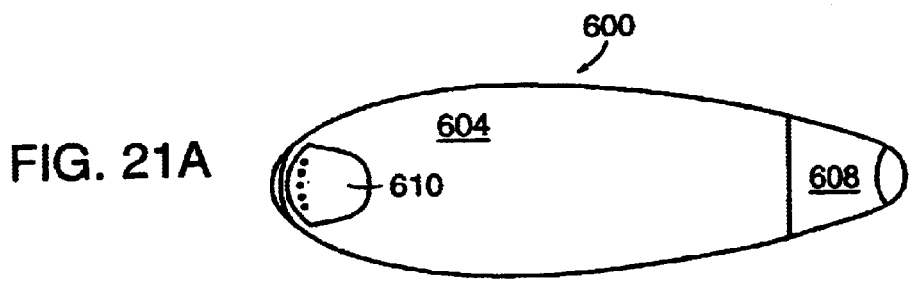
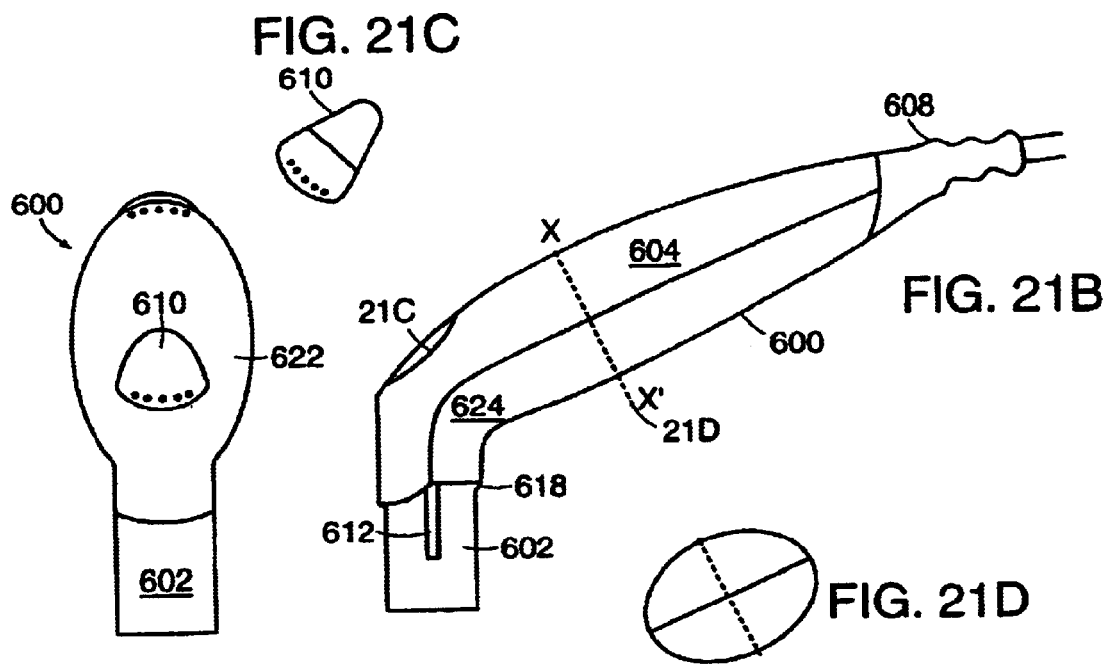
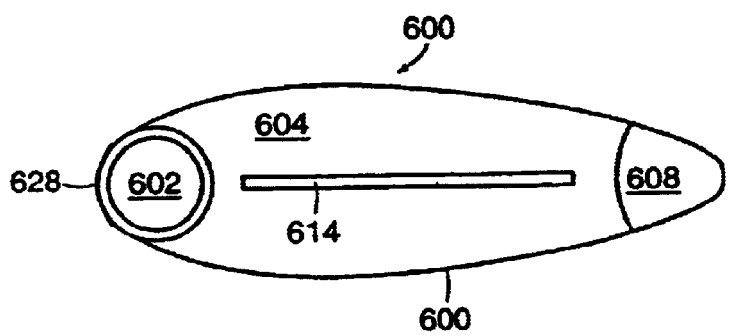

SPECTRAL VOLUME MICROPROBE ARRAYS

PRIOR APPLICATION

This application claims the benefit of U.S. Provisional Patent Application No. 60/115,373, filed Jan. 11, 1999, and is a continuation-in-part of U.S. patent application Ser. No. 09/241,806 filed Feb. 2, 1999, now U.S. Pat. No. 6,411,835, this latter Application having been filed as a continuation-in-part of U.S. patent application Ser. No. 08/782,936 filed Jan. 13, 1997 now U.S. Pat. No. 6,104,945. Both such applications are herein incorporated by reference.

FIELD OF THE INVENTION

The present invention relates to systems and methods for providing a barrier to prevent contact of an optical probe from surrounding features of the environment. More particularly, the present invention relates to systems and methods for providing a disposable sheath for a medical apparatus.

BACKGROUND OF THE INVENTION

An important requirement exists for an instrument that will provide rapid and automatic diagnostic information, for example of cancerous and otherwise diseased tissue. In particular, there is a need for an instrument that would map the extent and stage of cancerous tissue without having to excise a large number of tissue samples for subsequent biopsies. In the current art, the medical profession relies generally on visual analysis and biopsies to determine specific pathologies and abnormalities. Various forms of biochemical imaging are used as well. Unique optical responses of various pathologies are being exploited in attempts to characterize biological tissue as well. These prior art techniques, however, contain limitations. pathologies are being exploited in attempts to characterize biological tissue as well. These prior art techniques, however, contain limitations.

For example, performing a tissue biopsy and analyzing the extracted tissue in the laboratory requires a great deal of time. In addition, tissue biopsies can only characterize the tissue based upon representative samples taken from the tissue. This results in a large number of resections being routinely performed to gather a selection of tissue capable of accurately representing the sample. In addition, tissue biopsies are subject to sampling and interpretation errors. Magnetic resonance imaging is a successful tool, but is expensive and has serious limitations in detecting pathologies that are very thin or in their early stages of development.

One technique used in the medical field for tissue analysis is induced fluorescence. Laser induced fluorescence utilizes a laser tuned to a particular wavelength to excite tissue and to cause the tissue to fluoresce at a set of secondary wavelengths that can then be analyzed to infer characteristics of the tissue. Fluorescence can originate either from molecules normally found within the tissue, or from molecules that have been introduced into the body to serve as marker molecules.

Although the mechanisms involved in the fluorescence response of biological tissue to UV excitation have not been clearly defined, the fluorescence signature of neoplasia appears to reflect both biochemical and morphological changes. The observed changes in the spectra are similar for many cancers, which suggest similar mechanisms are at work. For example, useful auto-fluorescence spectral markers may reflect biochemical changes in the mitochondria, e.g., in the relative concentration of nicotinamide adenine dinucleotide (NADH) and flavins. Mucosal thickening and changes in capillary profusion are structural effects that have been interpreted as causing some typical changes in the spectroscopic record.

The major molecules in biological tissue which contribute to fluorescence emission under 337 nm near UV light excitation, have been identified as tryptophan (390 nm emission), chromophores in elastin (410 nm) and collagen (300 nm), NADH (470 nm), flavins (520 nm) and melanin (540 nm). However, it should be noted that in tissue, there is some peak shifting and changes in the overall shape relative to the pure compounds. Accordingly, the sample can be illuminated with a UV beam of sufficiently short wavelength and record responses from the above enumerated wavelengths of light in order to determine the presence of each of above identified contributions to tissues types.

It has been further shown that hemoglobin has an absorption peak between 400 and 540 nm, while both oxyhemoglobin and hemoglobin have strong light absorption above 600 nm. Blood distribution may also influence the observed emission spectra of elastin, collagen, NAD, and NADH. Further compounds present in tissue which may absorb emitted light and change the shape of the emitted spectra include myoglobin, porphyrins, and dinucleotide co-enzymes.

A general belief is that neoplasia has high levels of NADH because its metabolic pathway is primarily anaerobic. The inability of cells to elevate their NAD+: NADH ratio at confluence is a characteristic of transformed cells related to their defective growth control. The ratio of $NAD^+$: NADH is an indicator of the metabolic capability of the cell, for example, its capacity for glycolysis versus gluconeogenesis. Surface fluorescence has been used to measure the relative level of NADH in both in vitro and in vivo tissues. Emission spectra obtained from individual myocytes produce residual green fluorescence, probably originating from mitochondrial oxidized flavin proteins, and blue fluorescence is consistent with NADH of a mitochondrial origin.

Collagen, NADH, and flavin adenine dinucleotide are thought to be the major fluorophores in colonic tissue and were used to spectrally decompose the fluorescence spectra. Residuals between the fits and the data resemble the absorption spectra of a mix of oxy-and deoxy-hemoglobin; thus the residuals can be attributed to the presence of blood.

Alfano, U.S. Pat. No. 4,930,516, teaches the use of luminescence to distinguish cancerous from normal tissue when the shape of the visible luminescence spectra from the normal and cancerous tissue are substantially different, and in particular when the cancerous tissue exhibits a shift to the blue with different intensity peaks. For example, Alfano discloses that a distinction between a known healthy tissue and a suspect tissue can be made by comparing the spectra of the suspect tissue with the healthy tissue. According to Alfano, the spectra of the tissue can be generated by exciting the tissue with substantially monochromatic radiation and comparing the fluorescence induced at least at two wavelengths.

Alfano, in U.S. Pat. No. 5,042,494, teaches a technique for distinguishing cancer from normal tissue by identifying how the shape of the visible luminescence spectra from the normal and cancerous tissue are substantially different.

Alfano further teaches, in U.S. Pat. No. 5,131,398, the use of luminescence to distinguish cancer from normal or benign tissue by employing (a) monochromatic or substantially monochromatic excitation wavelengths below about 315 nm, and, in particular, between about 260 and 315 nm, and, specifically, at 300 nm, and (b) comparing the resulting luminescence at two wavelengths about 340 and 440 nm.

Alfano, however, fails to teach a method capable of distinguishing between normal, malignant, benign, tumorous, dysplastic, hyperplastic, inflamed, or infected tissue. Failure to distinguish these entities prevents selecting appropriate therapies. While the simple ratio, difference and comparison analysis of Alfano and others have proven to be useful tools in cancer research and provocative indicators of tissue status, these have not, to date, enabled a method nor provided means which are sufficiently accurate and robust to be clinically acceptable for cancer diagnosis.

It is understood that the actual spectra obtained from biological tissues are extremely complex and thus difficult to resolve by standard peak matching programs, spectral deconvolution or comparative spectral analysis. Furthermore, spectral shifting further complicates such attempts at spectral analysis. Last, laser fluorescence and other optical responses from tissues typically fail to achieve depth resolution because either the optical or the electronic instrumentation commonly used for these techniques entail integrating the signal emitted by the excited tissue over the entire illuminated tissue volume.

Rosenthal, U.S. Pat. No. 4,017,192, describes a technique for automatic detection of abnormalities, including cancer, in multi-cellular bulk biomedical specimens, which purports to overcome the problems associated with complex spectral responses of biological tissues. Rosenthal teaches the determination of optical responses (transmission or reflection) data from biological tissue over a large number of wavelengths for numerous samples and then the correlation of these optical responses to conventional, clinical results to select test wavelengths and a series of constants to form a correlation equation. The correlation equation is then used in conjunction with optical responses at the selected wavelengths taken on an uncharacterized tissue to predict the status of this tissue. However, to obtain good and solid correlations, Rosenthal excises the tissues and obtains in essence a homogeneous sample in which the optical responses do not include the optical signatures of underlying tissues. Rosenthal's methods, therefore, may not be suitable for in vivo applications.

In studies carried out at the Wellman Laboratories of Photomedicine, using a single fiber depth integrating probe, Schomacker has shown that the auto-fluorescence of the signature of human colon polyps in vivo is an indicator of normality, benign hyperplasia, pre-cancerous, and malignant neoplasia. See Schomacker et al., *Lasers Surgery and Medicine*, 12, 63–78 (1992), and *Gastroenternlogy* 102, 1155–1160 (1992). Schomacker further teaches using multivariant linear regression analysis of the data to distinguish neoplastic from non-neoplastic polyps. However, using Schomacker's techniques, the observation of mucosal abnormalities was hindered by the signal from the submucosa, since 87% of the fluorescence observed in normal colonic tissue can be attributed to submucosal collagen.

Accordingly, there is a need for a more effective and accurate device to characterize specimens, and particularly in vivo specimens, which will obtain responses from well defined locations or volume elements within said specimen, and present data automatically from a relatively large area comprising a plurality of such locations or volume elements. Furthermore, there is a need for methods to automatically interpret such data in terms of simple diagnostic information on said locations or volume elements.

In U.S. Pat. No. 5,713,364, DeBaryshe et al. teaches the general principles of obtaining valuable analytical data from a volume element in a target sample by using spatial filters with dimensions that are generally larger than the diffraction limits for the wavelengths of the probing radiation. Such spatial filtration is obtained by an optical device including an illumination and a detection system both containing field stops and the field stops being conjugated to each other via the volume element to be analyzed, providing in essence a non imaging volume microprobe.

While the family of devices described in the aforementioned application are very useful in the analysis of a plurality of points within a target sample, there is a need to easily and automatically obtain such data on a full array of points so as to convert these data to an artificial image of the analytical findings over a large area of the sample. This is particularly important when heterogeneous samples, such as biological samples are examined with the non imaging volume microprobe. For instance, when examining tissues to determine the presence or absence of oncological pathologies, or other pathologies, visual techniques are followed, in some cases, by the resection of biopsy specimen. Such techniques are naturally limited in that the physician eye can only assess the visual appearance of potential pathologies, and the number of biopsies taken is by necessity limited. The appearance of pathological tissues does not provide information on the depth of the pathologies, and cannot provide positive diagnosis of the pathology. Furthermore, since biopsies are carried out ex vivo, a time lag between the taking of the biopsy and obtaining its results cannot be avoided. It would be very useful for physicians to have a device capable of performing such diagnostic tasks in vivo and to obtain differential diagnostics (between healthy and pathological tissues) while performing the examination. This is particularly important when performing exploratory surgical procedures, but can be very useful when examining more accessible tissues as well.

A number of devices have been described in the prior art relating particularly to confocal microscopy where illumination and detection arrays are provided. For instance, a confocal scanning microscope in which mechanical scanning of the illuminating and the transmitted (or the reflected) beams is avoided is described in U.S. Pat. No. 5,065,008. A light shutter array is used to provide synchronous detection of a scanned light beam without the need to move a photodetector to follow the scanning beam, and each of the shutters is serving, in essence, as a field stop in the confocal microscope. In other embodiments, two overlapping arrays of liquid crystals are used as optical shutter arrays to attempt reduction in the size of the field stops. As is well known in the art of confocal microscopy, in order to obtain the desired resolution afforded by this technique, the dimensions of the field stops need to be small relative to the diffraction limit of the optical beam used in the system. Other embodiments also provide for two sets of field stops, conjugated within the sample, one set for the illuminating beam and one set for the transmitted or reflected beam. While this patent teaches the use of electronic scanning of the illumination and response beams, the illumination intensity and response signal strength are drastically limited due to the use of dual liquid crystal optical shutters required to achieve the pin-hole effect of a scanning confocal microscope.

Another confocal imaging device is taught in U.S. Pat. No. 5,028,802, where a microlaser array provides a flying spot light source in a confocal configuration. Similarly U.S. Pat. No. 5,239,178 provides for an illuminating grid for essentially the same purpose, except that light emitting diodes are used for the grid's light sources. These approaches, however, are limited to monochromatic illumination and are usable only with relatively long wavelengths at which solid state laser diodes and thus microlaser arrays or light emitting diode arrays are available.

None of these devices provide for an array of non-imaging volume microprobes. Accordingly, there is a need for a device comprising an array of non-imaging volume microprobes in which a plurality of volume elements in a sample can rapidly be scanned in order to obtain diagnostic or analytical information over a relatively large area of the sample without integrating the data from all the sampled volume elements or locations.

Where a diagnostic device is to come into contact with body tissues, there is a further need that its surfaces be insulated from contact with those tissues in order to avoid contamination. During sterile procedures, the device can introduce contamination into body tissues. Furthermore, the device can become contaminated by contact with the tissues of one patient and transmit that contamination to another patient. While these problems may be avoided by sterilizing the diagnostic device before each use, its delicate optical components may be damaged or incompletely sterilized by available techniques; furthermore, a sterilization cycle prior to each use, even if effective, may be costly and time-consuming.

As an alternative, some form of barrier may be provided that is to be interposed between the diagnostic device and the patient's tissues. In order to avoid the abovementioned problems of contamination and cross-contamination, however, it is important that a sterile barrier be applied prior to each use of the diagnostic device. Sterility may be effected either by sterilizing the barrier apparatus each time it is used, or by fabricating the barrier apparatus as a single-use device which is sterile and disposable. It is furthermore important with a single-use device that its reuse be prevented so that a fresh sterile insulator is employed for each patient.

It is desirable that an apparatus that provides a barrier insulating the diagnostic device be compatible with the optical characteristics of the diagnostic device, so that the presence of the barrier does not impair the diagnostic device's accuracy or ease of use. Thus, the method used to isolate the probe from the target tissue must be compatible with the requirement that excitation beams traveling to the tissue and the optical responses therefrom be transmitted through the barrier with minimal optical losses and without signal alteration. When the barrier apparatus is applied to the diagnostic device, it is further important that the optical properties of the system remain stable throughout the diagnostic test, and remain consistent from one test to another. To ensure these qualities, it is desirable that the barrier be tightly adherent to the probe during a diagnostic procedure. Tight adherence of the barrier to the probe will furthermore avoid accidental detachment between the probe and the sheath during the procedure, thus preventing this mechanism of contamination.

It would be further desirable to provide a barrier apparatus that conforms to the anatomic area in which it is being used. For example, a differently shaped barrier apparatus may be required for diagnosing tissues through an endoscope than would be useful for diagnosing abnormalities of the cervix.

One device adapted for the examination of the cervix uteri may be termed a colpoprobe. A barrier apparatus shaped to fit over a colpoprobe might have particular anatomic and optical characteristics. It would be advantageous, for example, during a colposcopic examination to provide not only an image of the cervix, but also a set of data correlated with important tissue variations from the normal state which cannot be visualized in normal imaging systems. It is desirable that, since the contemplated use of certain diagnostic systems such as the colpoprobe includes screening of large populations, it is important that the systems and their biological isolation sheaths be easy to use in an error-free manner, and that the sheath be readily attached and detached from the diagnostic system rapidly, simply and without mistake. A barrier insulating the colpoprobe from the tissues of the vagina and the cervix would advantageously be compatible with both imaging and non-imaging applications.

The prior art teaches the uses of an external barrier or sheath as an alternative to the complete sterilization of a diagnostic or therapeutic device. For instance, sanitary covers or speculate for tympanic thermometers probes are described in three US patents issued to O'Hara et al., U.S. Pat. Nos. 4,662,360, 5,516,010 and 5,707,343. However, the covers disclosed in these patents only fit tympanic thermometers and cover only the tip of the device, not permitting modification. Furthermore, nothing in the design of these tympanic thermometers covers prevents their repeated use.

As another example, Furukawa et al., in U.S. Pat. Nos. 5,730,701 and 5,860,913, and Katsurada et al., U.S. Pat. No. 5,865,726, teach the use of disposable tips for side view type endoscope. However, these tips do not provide biological isolation for anything beyond the tip. Furukawa et al. in U.S. Pat. No. 5,730,701 suggest that the attachment means or locks plastically deform upon detachment, thus preventing the reuse of the same tip cover. However, these locking mechanisms merely deform, rather then break away. Thus reshaping a used disposable tip to the original shape by manipulation of the locking mechanism is feasible, permitting the tip's reuse. Furthermore, this feature requires that the first attempt in affixing the tip to an endoscope's end be successful; otherwise, the tip cannot be used and will need to be discarded.

Yabe et al., in a number of U.S. Pat. Nos. 5,419,311, 5,458,132, 5,458,133, 5,536,236, 5,545,121 and 5,556,367, describe a variety of endoscope covers that engulf the whole endoscope. However, these devices are specific to the particular device, an endoscope with a set of complex features. The covers themselves are complicated devices, difficult to assemble over an endoscope and requiring specialized training, making their use impractical for a screening setting. Furthermore, these covers include channels for fluids and for air insufflation and are specifically designed each to fit a specific endoscope design and specific endoscope functionality. As an example, U.S. Pat. No. 5,536,236 discloses an endoscope cover bearing optical filters preventing back scattering from laser beams used in endoscopic procedures through said endoscope. The endoscope cover of the '236 Patent is further characterized by an inner surface designed to hold it in place over the endoscope by friction fitting. As another example, U.S. Pat. No. 5,545,121, teaches display means that indicate that the cover has been properly applied to the specific endoscope for which it is used. U.S. Pat. No. 5,556,367 discloses the additional feature of adjustable length, whereby the cover may be lengthened to fit any of a preselected series of endoscopes. As previously mentioned, each of these covers is intended for a use with a particular endoscope system. Further, none of these provides a biological barrier that may be fitted on a simple optical diagnostic device with great ease by operators with little training. Nor do these covers provide means that assure that the same barrier or sheath is not used sequentially on different patients.

Chikama in U.S. Pat. Nos. 5,154,166 and 5,159,919 discloses an endoscope cover made of a rigid material that has a complex structure including a mating longitudinal groove in the endoscope anchoring an opposing anchoring projection in the rigid endoscope cover. This cover has the same shortcomings cited above for the various endoscope covers taught by Yabe et al.

Kimura et al. in U.S. Pat. No. 5,695,448 disclose a simple tubular disposable sheath having at least a distal transparent end for viewing and special positioning means assuring that the distal transparent end is within the view range of the endoscope. This cover, like many of those mentioned above, does not have means for preventing reuse. Furthermore, no special means are disclosed whereby the transparent window may transmit not only images of the target operational area but also accurate optical responses from target tissues subjected to excitation beams for diagnostic purposes.

Williams et al. in U.S. Pat. Nos. 4,237,984 and 5,413,092 describe a sheath-like cover for an endoscope bearing a very thin lens cover (between 0.002" to 0.010" thick) intended as an improvement over thicker lens covers for reducing back reflections of light from the illumination channel into the field of view of the endoscope. This feature is not adapted for UV-induced fluorescence systems like those contemplated herein because in these systems the excitation beam uses wavelengths that differ markedly from the wavelengths obtained as responses from the excited tissue, and minor reflections of the excitation beams are of little importance.

Saab in U.S. Pat. No. 5,37,734 and Hamlin et al. in U.S. Pat. No. 5,690,605 disclose rigid tubular structures as disposable endoscopic sheaths of a configuration inapplicable to the devices of the present invention. Further, neither patent teaches methods for preventing reuse.

Another type of a disposable endoscope cover is taught by Sidall et al. (U.S. Pat. No. 4,741,326), which describes a sheath that is manually rolled over the endoscope. The sheath has a complex structure comprising its distal element. Employing this device is complicated, so it has not been widely adopted. Furthermore, the complex distal end has tubular structures attached thereto that are not suitable for probes such as those disclosed herein.

Oneda et al. in U.S. Pat. No. 4,979,498 describe a disposable light transmitting sleeve disposed about the distal member of a cervicoscope. This device, however, fails to provide for means that prevent the reuse of the sleeve, nor does it provide the special distal end properties required to optimize the transmission of the excitation beams to the tissues and reception by the system of optical responses from said tissues.

Sinofsky in U.S. Pat. No. 5,773,835 proposes the use of a casing made of a. fluoropolymer, acting as a disposable sheath over a thin UV illuminator/collector assembly that could be used in fluorescence analysis of tissue within body cavities. Using such a material for a sheath may be particularly beneficial when the optical head provides for diagnostic information by excitation of target tissue with a UV beam and detection of the fluorescence response from the tissue, because fluoropolymers have only minimal autofluorescence. However, the Sinofsky sheath provides no means that assure that it will not be reused on multiple subjects. Nor does the Sinofsky sheath provide an optical window adapted for a plurality of optical functions, as may be required by an optical probe according to the systems and methods of the present invention.

Similarly, Sklandev et al. in U.S. Pat. No. 5,855,551 describe a disposable sheath intended to be used with a probe that uses both optical and electrical responses from body tissues for diagnostic purposes. In this device, however, the disposable sheath itself contains active elements of the diagnostic system such as light emitting diodes and electrical contacts. Furthermore, this patent teaches no means for preventing reuse of the disposable sheath on subsequent patients.

There is therefore a need in the art to provide for a disposable biological barrier or sheath compatible with the particular characteristics of a non-imaging volume microprobe. There is a need for a sheath that minimizes the fluorescence response directly from the optical window thereof In addition, it would be advantageous to have a sheath adapted for the anatomic area where the non-imaging volume microprobe would be used. Furthermore, there is a need for such a sheath constructed to prevent its reuse. Finally, there is a need to devise a sheath that is of simple structure, easy to mount and to remove from the diagnostic instrument.

SUMMARY OF THE INVENTION

In one embodiment, the present invention may automatically obtain optical responses from a three dimensional array of volume elements or locations by providing a plurality of non imaging volume microprobes in parallel which automatically presents mapping of the diagnostic information sought, in a plane generally parallel to the surface of the specimen (the xy plane) and in the z direction which is generally perpendicular to the xy plane. As used in this specification, the term "location" refers to any point in three dimensional space related to the tissue sample. A location may be a point within the substance of a tissue sample, or it may be found on the surface of the tissue sample. A location within a tissue sample may be termed a volume element. In some embodiments, the systems and methods of the present invention may be used for the evaluation of any material. To evaluate a material, these systems and methods may determine a characteristic of the material. In certain embodiments, the systems and methods of the present invention are directed to a sample of a biological material. A biological material is understood to include those materials derived from or related to unicellular or multicellular biological organisms. A sample of a biological material may include one or more than one specimens of the biological material under investigation. The sample of biological material may be located in an in vivo system or in an in vitro system. If in vivo, the sample may be adjacent to other tissues of like or different kinds. The sample may represent an area of abnormality within a tissue, or the sample may represent an entire tissue. The tissues comprising an in vivo system may be surrounded by other adjacent tissues. The systems and methods of the present invention may be used within a living organism to examine a body tissue in vivo. A body tissue may reside or be derived from a human or a non-human living organism. Other uses for these systems and methods will be apparent to ordinary practitioners of the relevant arts. For the purposes of this specification, the term "patient" refers to anyone undergoing diagnostic evaluation using certain of the systems and methods disclosed herein.

In one embodiment of these disclosed systems and methods, optical responses from an array of volume elements are further analyzed to provide visually (namely on a monitor) information which is not readily available by direct examination of the sample. This is achieved by, in essence, providing an artificial three dimensional biochemical map composed from the optical responses, or more accurately, derivatives of such responses, of each individual volume element examined in an array, and by further converting these biochemical data to an artificial pathological image delineating the nature, extent and depth of pathologies observed. This is achieved by creating an artificial pathological scale, for each pathology of interest, by training the instrument to recognize specific pathologies. In one embodiment, a training set of specimens on which optical responses with a non imaging volume microprobe were collected, is subjected to a rigorous laboratory determination of the pathological state of each of its specimens and a value is assigned to each specimen on the artificial pathological scale. A set of linear equations relating to the responses (or functions of the responses) for each specimen to the pathological states, is constructed and optimized solutions for the correlation coefficients sought. These correlation coefficients are then used to transform responses obtained on unknown specimen to obtain the pathological state of these unknown specimen.

The objectives of the instant invention are achieved by providing an array of optical assemblies each consisting of two conjugated, or partially conjugated, optical assemblies. In each such assembly, the first optical assembly is designed to image selectively a transmitted beam from a light source, or another source of radiation, within a plurality of selected volume elements of a sample in a sequential manner. The second optical assembly is designed to collect light, or radiation emanating from the volume elements, in the same sequential manner, and transmit the collected light or radiation to a detector for further analysis of the interaction of the first transmitted beam with the volume elements. The first optical assembly includes a first field stop to achieve selective illumination of a selected volume element, and the second optical assembly includes a second field stop to restrict acceptance of said emanating radiation or light into the collection optics, essentially only from the selected volume element. Furthermore, a controller is provided to adjust the depth of the selected volume elements relative to the surface of the sample by controlling the respective focal points of the two optical assemblies while keeping them conjugated and having the volume element as a common conjugation point for both optical assemblies.

Sequential illumination of the various volume elements in an array is desired to assure that only responses from a given volume element are collected by the optical assembly associated with the volume element at any given time.

The sequential illumination of a plurality of volume elements may be carried out with a variety of devices. In some embodiments of the invention, an array of optical shutters is interposed between the light source and the sample, each shutter serving as either a field stop or an aperture stop for a specific optical assembly. In some embodiments, a single array of optical shutters is provided, while in other embodiments two arrays of optical shutters are provided. In yet another embodiment of the invention, an array of micromirrors is used to control the sequential illumination and response collection of the various volume elements in the sample. In yet another embodiment of the invention, an arrayed bundle of optical fibers is used to sequentially illuminate an array of volume elements in the sample and to collect sequentially responses from the volume elements. Appropriate movement of the optics so as to probe various depths of the sample is provided.

The optical responses from the selected volume elements bear important information about the volume elements, such as chemistry, morphology, and in general the physiological nature of the volume elements. When the sample is spectrally simple, these optical responses are analyzed by classical spectral techniques of peak matching, deconvolution or intensity determination at selected wavelengths. One such system may be the determination of the degree of homogeneity of a mixture or a solution of a plurality of compounds. However, when the samples are complex biological specimens, as mentioned above, the spectral complexity is often too great to obtain meaningful diagnosis. When such biological specimens are analyzed for subtle characteristics, we surprisingly found that the application of correlation transforms to spatially filtered optical responses obtained from an array of discrete volume elements, or the use of such transforms in conjunction with data obtained through non imaging microscopy, yields diagnostically meaningful results.

Specifically, we first select a training sample of a specific target pathology. Such a sample will preferably have at least 10 specimens. Optical responses are first collected from well defined volume elements in the specimens and recorded. These optical responses may be taken with an array microprobe or with a single volume microprobe device as described in the aforementioned co-pending application. The same volume elements that have been sampled with the non imaging volume microprobe are excised and biopsies (namely cytological analysis of the excised volume elements) is carried out in a classical pathological laboratory and the specimens are scored on an arbitrary scale which relates to the extent of the pathology, C (for instance a specific cancer) being characterized. These scores, $C_j$, where $C_j$ is the score value assigned to the specimen j within the training set, should be as accurate as possible, and thus an average of a number of pathologists' scores (determined on the same volume elements, j), may be used. We now create a set of equations $Ga_{ic}$ $F(I_{ij})=C_j$, where i designates a relatively narrow spectral window (usually between 5 and 50 nm) and thus $F(I_{ij})$ is a specific function of the response intensity or other characteristics of the spectral response in the window i for volume element j. The function F is sometimes the response intensity itself, in that window, namely, $F(I_{ij})=I_{ij}$, or $F(I_{ij})=(dI_{ij}/d\lambda)$, where $\lambda$ is the median wavelength in the window i. The factors $a_{ic}$, the correlation transform's coefficients for the pathology C, are now found from the set of equations created above, by means well known in the prior art, such as multivariate linear regression analysis or univariant linear regression analysis. In such analysis, the number of wavelength windows i required to obtain faithful correlations between the optical responses and the pathological derivations of the values $C_j$, is minimized and the set of correlation coefficients $a_{ic}$ for the pathology, C are found. When we now record the responses $(I_{ik})$ (which is a vector in the space of i optical windows, now minimized to a limited number of discrete elements) on a sample outside the training set and apply the transform operator $(a_{ic})$ on the vector $F(I_{ik})$, namely obtain the sum $\Sigma a_{ic}$ $F(I_{ik})=C_k$, we automatically obtain the score for the target pathology C for the volume element sampled.

It should be understood that other statistical tools, such as principal component regression analysis of the optical responses, may be used as well. In addition, linear discriminant analysis (LDA), quadratic discriminant analysis (QDA), or their weighted average i.e. regularized discriminant analysis (RDA) can be used. One may also consider using in the correlation transforms, in lieu of functions of the optical responses at specific wavelengths, the Fourier transform of the total spectral responses. Furthermore, while taking the spectral responses from specific volume elements, these responses may be treated optically through either a spatial Fourier transform generator (such as a Sagnac interferometer) or a temporal Fourier transform generator (such as a Michelson interferometer), and then the data obtained may be used to create the desired correlation matrices to train the system for further data acquisition and image generation of the distribution of possible pathologies.

Instruments embodying the invention are deemed useful for obtaining artificial images of some characteristics of turbid materials, such as biological tissue, plastics, coatings, and chemical reaction processes, and may offer particular benefits in analysis of biological tissue, both in vitro and in vivo. To provide analysis of biological materials located within a living body, certain embodiments of the present invention may be adapted to work with existing endoscopes, laparoscopes, or arthroscopes. The systems and methods of the present invention may be adapted to work within a body orifice, such as the mouth, the ear canal, or the vagina. The systems and methods of the present invention may be adapted to work within a body lumen, such as the colon or the bladder. The systems and methods of the present invention may be adapted to work within a body cavity such as the peritoneal or the pleural cavity. Other adaptations may be envisioned by ordinary skilled artisans in the field.

To adapt the invention for diagnostic purposes involving contact with biological tissues, the diagnostic apparatus may be provided with a covering to insulate it from contact with biological tissues. It is an objective of the present invention to provide a protective sheath for in vivo optical diagnostic systems that may serve as a biological barrier between patient's tissue and the optical probe. In one embodiment, the systems and methods of the invention may provide a barrier disposed external to the diagnostic probe that separates the probe from any tissue of the body, including those tissues in continuity with the target tissue sample and including those tissues adjacent to or in proximity to the tissue sample. A barrier according to these systems and methods may insulate a colposcopic probe, for example, from contact with the tissues of the cervix, vagina and vulva. Other barriers may be envisioned by practitioners skilled in the relevant arts that will prevent the probe from contact with relevant body tissues. It is a further objective in certain embodiments that the biological barrier be disposable and adapted for a single use. The term "single use" is understood to comprise the use for a single diagnostic measurement performed by the probe. It is desirable that the barrier or disposable sheath be capable of use with only one patient. As used in only one patient, a unique individual, the biological barrier may be adapted for a single use or may be adapted for multiple uses. Systems according to the present invention are adapted to prevent the use of the probe in more than one patient.

It is yet another objective to provide a sheath constructed to conform to the optical requirements of the diagnostic systems and methods of the present invention. In one embodiment, such a sheath advantageously would provide minimal interference with the optical responses produced by tissues after their excitation by a beam of electromagnetic radiation produced by a diagnostic system according to the present invention. In one embodiment, such a sheath would include an optical window, an optical filter, a lens or a polarizer capable of being exposed to ultraviolet radiation without producing a significant fluorescent response.

It is yet another objective to provide a protective sheath for a colposcopic optical probe or an optical probe adapted for the examination of the cervix uteri.

It is yet another object of the present invention to provide a sheath which may be mounted and dismounted on the optical probe with great ease and minimal training. It is an object of the invention that a sheath be equipped with an affixation mechanism that also orients the sheath on the probe in a preselected, optimal direction. It is a further object of the invention that a sheath possess mechanisms that facilitate the assurance of single use for the sheath. In one embodiment, a sheath may be provided with a mechanical affixation mechanism that is suitable only for a single use. In one embodiment, the affixation mechanism may entail damage to the attachment apparatus when the sheath is detached from the probe. In another embodiment, the sheath may be provided with an identifying marker that may be read by the probe so that the system may determine that the sheath is suitable for use. An identifying marker may provide data about the unused state of the sheath or data about the previous use of the sheath. It is an object of the present invention that the sheath interact with the probe to prevent the use of the probe in the absence of an unused sheath. A probe being used with the barrier may comprise a processing system that correlates certain data borne by the identifying marker on the sheath with an indicator that indicates or relates to an unused or a previously used state of the sheath. The probe to be used with the barrier may include a receptor system that receives a signal generated by a sensor on the barrier and that thereupon renders the probe operable or inoperable, depending upon the type of signal received. A probe rendered capable of being used may be termed operable or activated. In one embodiment, the probe may be inoperable in the absence of an unused sheath. In another embodiment, an unused sheath may be required for a signal to be produced that activates the probe. In one embodiment, the invention may provide a system for controlling use of a diagnostic apparatus that includes a diagnostic apparatus, a disposable sheath with an identifier that bears unique data to characterize that particular disposable sheath, a detector that produces a signal indicative of the unique data borne by the identifier, and a receiver system that responds to the signal produced by the detector, that determines the state of the disposable sheath and that provides a second signal that regulates activation of the probe. As understood herein, a signal or any other mechanism that regulates activation of the probe may activate the probe, may prevent it from being activated, or may provide any other type of regulation that affects the use of the probe.

It is an object of the invention that these systems and methods include a plurality of interactions between sheath and probe whereby the integrity of the sheath and its proper use are assured. In one embodiment, these systems and methods may comprise a database with which the probe apparatus communicates to determine the unused state of the sheath. In another embodiment, these systems and methods may comprise a set of diagnostic tests that ensure the integrity of the sheath and its proper positioning upon the probe, or that ensure the proper positioning of the probe with respect to the patient, or that ensure the proper type of sheath be placed on the probe. It is an object of the invention to provide proper sheaths for a plurality of anatomic areas where the probe may be used, for example the cervix and the endocervix.

The above and other subjects, features and advantages of the present invention will become apparent from the following description with reference to the accompanying drawings which illustrate examples of the present invention.

DESCRIPTION OF THE DRAWINGS

In FIG. 4A, the detection lens array is replaced with a single lens.

FIGS. 21A–F show various projections of an embodiment of an optical probe system with a protective sheath in place.

DETAILED DESCRIPTION OF THE INVENTION

Figure 1:
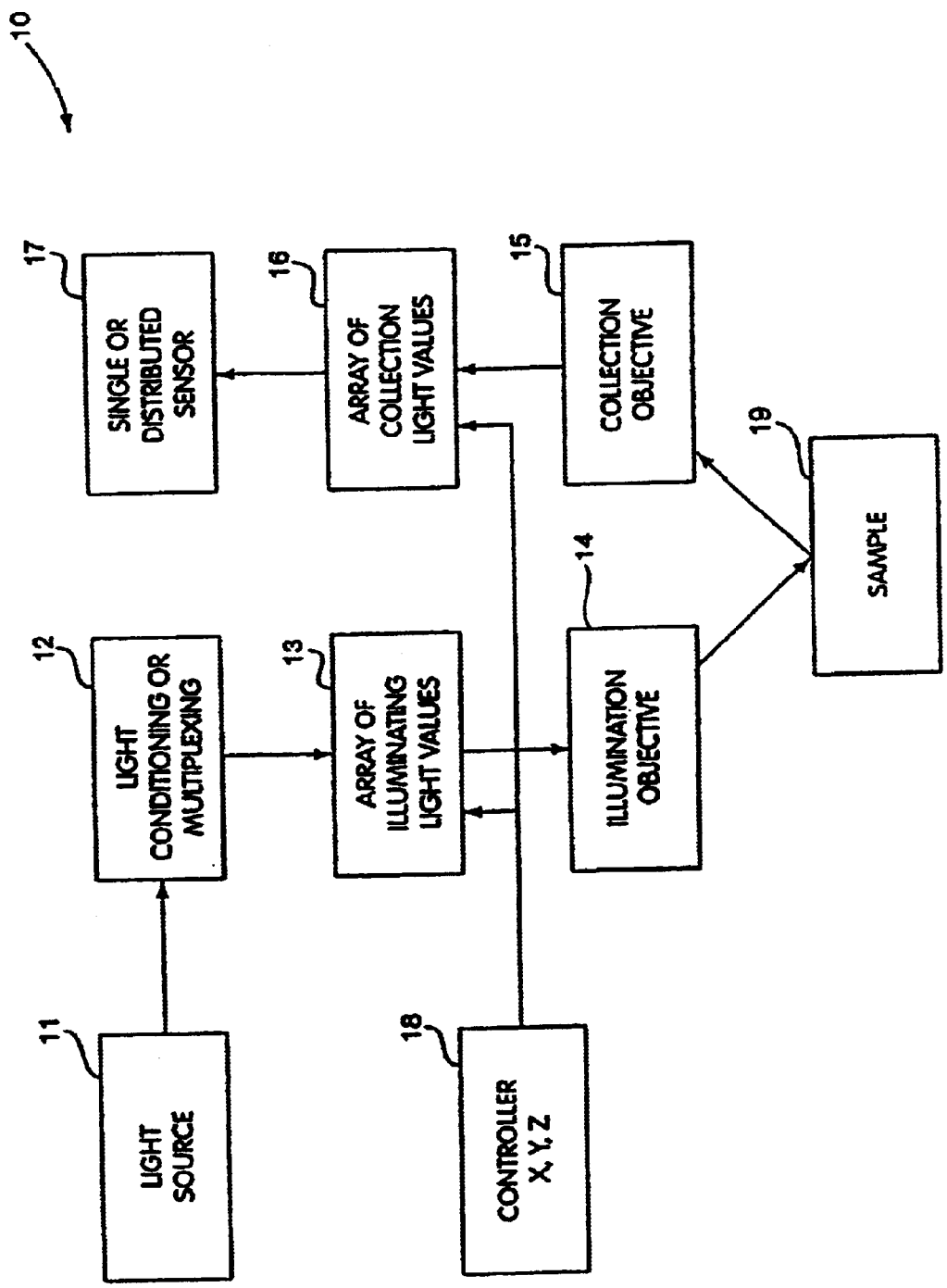
FIG. 1 is a schematic and generalized block diagram of the major elements of the present invention.

In FIG. 1 we show a generalized schematic volume probe array, 10, whose function is to collect data from a plurality of points in a target sample. The system generally includes an appropriate light source I 1, whose light output is conditioned and may be multiplexed in block 12 to create a plurality of light sources to be relayed to an array 13 of light valves. These light valves may act as illuminating field stops or aperture field stops, and only one valve is open at a given time, thus providing for sequential illumination of volume elements in sample 19. The light emanating from each light valve is then directed to a targeted volume element in the sample 19 with an appropriate illumination objective 14. In some embodiments, a single objective lens is used, while in other embodiments, we incorporate an array of objective microlens having the same periodicity as that of the light valve array.

Responses from each targeted volume element in the form of light emanating from the volume elements, is collected through a collection optics objective 15 (which in some embodiments may be the same as the illumination objective and an array of microlens), and through an array 16 of light valves (which may also be the same array as the one used for illumination). The responses are then directed to one or more detectors 17 to determine their optical and spectral characteristics.

It should be emphasized that both the illumination optics and the collection optics each contain a field stop having dimensions that are relatively large in relation to the average wavelength of the illuminating radiation, and furthermore, these field stops are conjugated to each other through the volume element examined. As a result, a well defined volume element is illuminated at any time, and the optical response from the element collected through the field stop of the collection optics is essentially limited to responses emanating from the volume element.

A controller 18 is provided to control the sequencing of the volume elements scanned (in the x,y plane, the plane of the sample) and to control the depth of the volume elements examined (in the z direction.)

Figure 2:
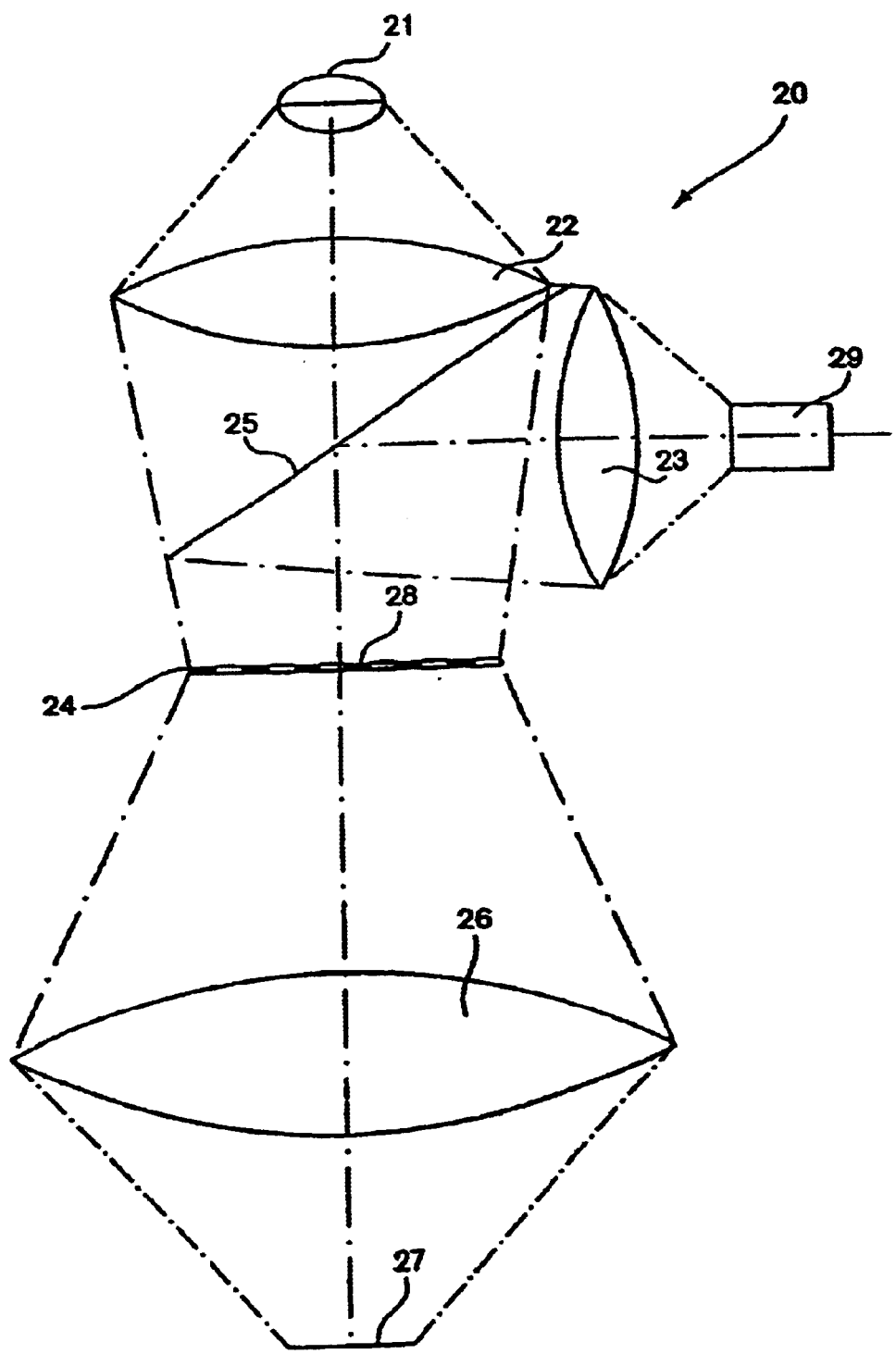
FIG. 2 is a block diagram of an embodiment of the invention with an array of light valves, in which each light valve acts as an addressable field stop for the illumination and detection beams.

In FIG. 2, a simple example of an array volume microprobe system 20 is shown. The system includes a light source 21. Light from the light source is condensed with a lens 22 onto an array of light shutters 24, through a beam splitter 25. In this embodiment, each element 28 in the light shutter array serves as a field stop which is being imaged through an objective lens 26 on a sample 27. The dimensions and shape of the shutters determine the morphology of volume elements sampled in a manner discussed in detail in U.S. Pat. No. 5,713,364. In essence, the mean dimension, d, of each shutter is selected to be larger than the wavelength divided by the numerical aperture, NA, of the objective of $d > \lambda/NA$. Thus the image of the field stop in the plane of the sample is larger than the diffraction limited resolution for the wavelength. As a result, a very large proportion of the light that traverses a given field stop and is imaged in the sample is within a well-defined volume element of the sample. Similarly, while the total response to the illumination is distributed over a very large spatial angle (essentially 4B steradians), only responses that are emanating from within the same volume element are imaged back onto the field stop and reach detector 29, by being reflected on the beam splitter 25 onto a collector lens 23 which concentrates the response onto the detector 29. This results from the fact that the respective field stops of the illumination and detection systems are conjugated to each other via the target volume element. In the embodiment shown in FIG. 2, both field stops are embodied within the same aperture (an optical shutter or a light valve 28 within the optical shutter array).

In some embodiments, the beam splitter 25 may be a dichroic mirror, particularly when the light source is a short wavelength (UV) exciting light source and the responses are fluorescence responses. In other embodiments, the beam splitter 25 may be a half silvered mirror which separates the optical path of responses from the sample from the optical path of the exciting beam, for instance, when the exciting beam is provided with a broad spectrum light source, and the responses involve back scattering and reflections from the sample (and thus mostly the extent of absorption of the exciting beam in the targeted volume element is examined).

The array of light valves, or optical shutters, may be implemented in a number of different ways. One may use liquid crystal sandwiched between two electrode arrays (deposited, as is in the prior art on transparent glass or plastic sheets in the form of transparent electrodes made of Indium Tin Oxide (ITO) or Tin Oxide (TO), usually doped with fluorine to provide good areal conductivity). One may also use films of PDLC (polymer dispersed liquid crystals) that might be easier to handle and have lower production costs. Another embodiment contemplated, when the required scanning is particularly fast, is an array of ferroelectric elements, each acting as a light valve. Yet another embodiment of the light valves may involve an array of PVDF (Polyvinyl-difluoride) bimorphs, each coated to be reflective (or opaque on both sides) on the side facing the light source and designed to bend out of the light path so as to create a light valve. The typical dimensions of the light valve range from a low of about 20 microns to as much as 1000 microns. The size is determined primarily by the application, the nature of the sample analyzed and the particular design of the specific array volume microprobe utilized. When using the general design of FIG. 2, with a single large objective lens serving as a common objective to all the field stops in the array, the space between adjacent light valves is usually kept as small as possible, so as to provide as closely spaced as possible scanned volume elements. It should be understood however that in some embodiments, the spacing is kept relatively large (as large as the field stop itself) when an image of the pathology consisting of well spaced discrete points is more appropriate.

In operation, the controller 18 keeps one of the light valves open and adjusts the position of the device so as to image the field stop at the desired volume element in the sample 27. Once the general position of the device relative to the sample has been optimized, the controller causes scanning of the surface of the specimen in the xy (the plane of the specimen) direction by sequentially closing an open light valve and opening an adjacent light valve. The time interval of each light valve in the open position is a strong function of the intensity of the light source and the efficiency of collection of the response from each volume element. In some embodiments, this time interval may be shorter than a millisecond, while in other embodiments tens to hundreds milliseconds are required.

The controller 18 also controls the position of the volume elements within the sample in the z direction, generally an axis perpendicular to the plane of the samples.

This may be achieved in a number of ways. For instance, the whole optical assembly may be moved back and forth in the z direction. In some embodiments, this translational movement of the image plane of the field stops in the sample may be achieved by moving the objective alone, or the array of light valves, or both of these elements simultaneously. The specific design depends on the particular embodiment of the device.

It should be appreciated that since the intensity of illumination is highest within the volume element probed by the excitation beam (relative to zones surrounding the volume element), and that the response detected by the sensor 29 is primarily from the same volume element (and contains very little illumination emanating from zones surrounding the volume element), that changing the position of the volume element within the sample in the z direction will provide responses from various depths of the sample. This, in essence allows for analysis, in vivo of tissues at various depths, as long as the overall absorption of the illuminating beam by the tissue and the responses to the beam are not excessive.

Figure 3:
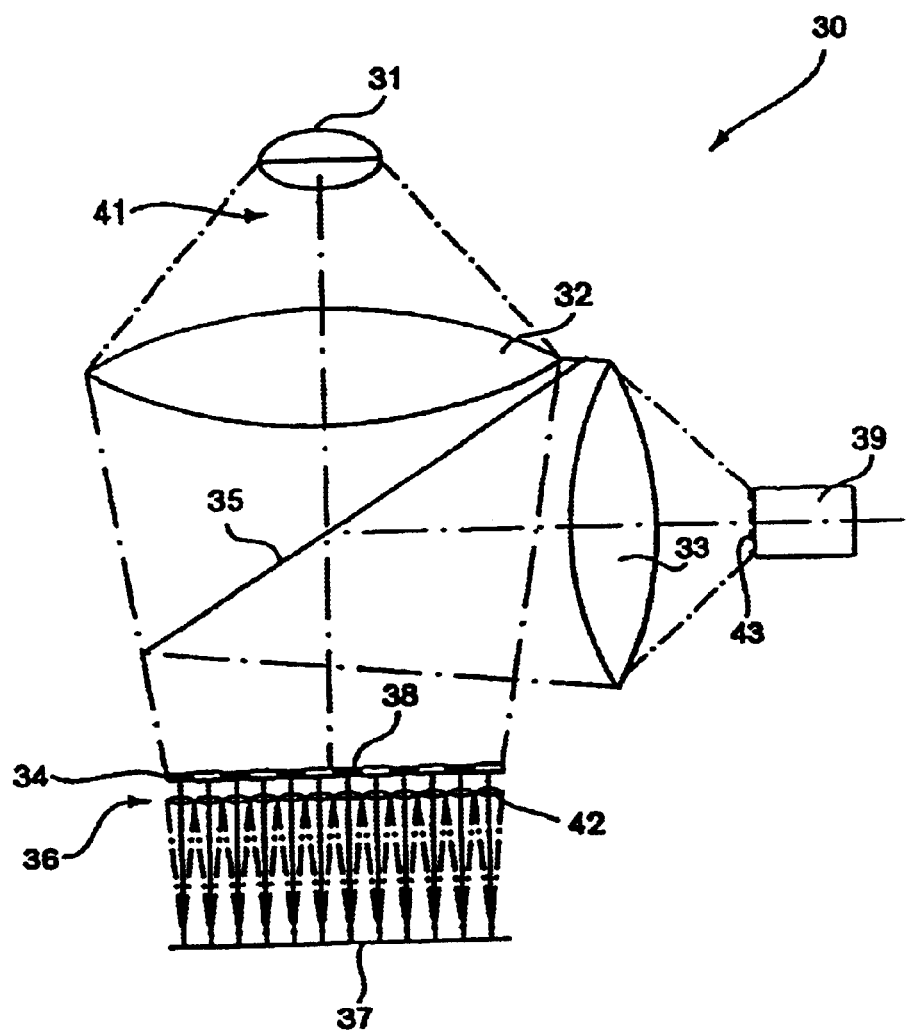
FIG. 3 illustrates an embodiment where an array of lenslets of the same periodicity as the array of light valves acts as an array of objective lens for both the illumination and detection beams.

In FIG. 3, a slightly different embodiment of an array volume microprobe 30 of the present invention is shown. The system includes a light source 31 with appropriate optics (not shown) to project a common field stop 41 through a condenser lens 32 onto an addressable shutter array 34. Each element in the addressable shutter array may be considered an aperture stop which serves to further limit the spatial distribution of the light impinging on a sample 37. In lieu of using a large singular objective (as used in the embodiment described in FIG. 2) to image the field stop on each volume element in the sample 37, a lens array 36 is interposed between the Ishutter array and the sample. The lens array 36 consists of a plurality of microlens 42. The periodicity of the lens array is exactly the same as that of the shutter array, and each lens 42 within the lens array 36 corresponds to a light valve 38 within the light shutter array 34. In most embodiments, the light impinging on the shutter array would be collimated, and the shutter array would be fixed in position relative to the lens array. The volume element probed would be at the focal point of the objective lens within the microlens array, and movement of the combination of the shutter and lens array in the z direction, may be used to probe different layers within the sample, as explained above when describing the array volume microprobe of FIG. 2. One can, however, conceive of other arrangements where the lens array and the shutter array are capable of moving independently, and probing the sample in the z direction is achieved by translation in the z direction of the lens array alone.

Light responses to the exciting radiation from the light source 31 from each of the sampled volume elements are collected through the same objective elements through which illumination is effected. The light responses are separated from the illuminating beam by the beam splitter 35. These responses are then imaged via a collecting lens 33 onto a collection field stop 43 that restricts the responses received by a sensor 39 to be essentially only from the probed volume element. In operation, the controller 18 opens a given shutter and allows the illumination of a single volume element. Furthermore, the same light shutter allows optical responses to the excitation to be recorded by the detector 39. This is followed by closing the light valve and opening another light valve, so that sequentially discrete volume elements within the sample are scanned to obtain optical responses thereof One may scan all the desired volume elements in the array in a given x,y plane and then rescan the array at a different depth (in the z axis), so as to obtain three dimensional information on the target sample. One may also choose to operate the array volume microprobe in such a way that for each pixel, the respective light valve 38 is kept open, while the controller causes the shutter array together with the lens array to move in the z direction, thus probing at the same x,y location volume elements at various depths of the specimen.

Figure 4:
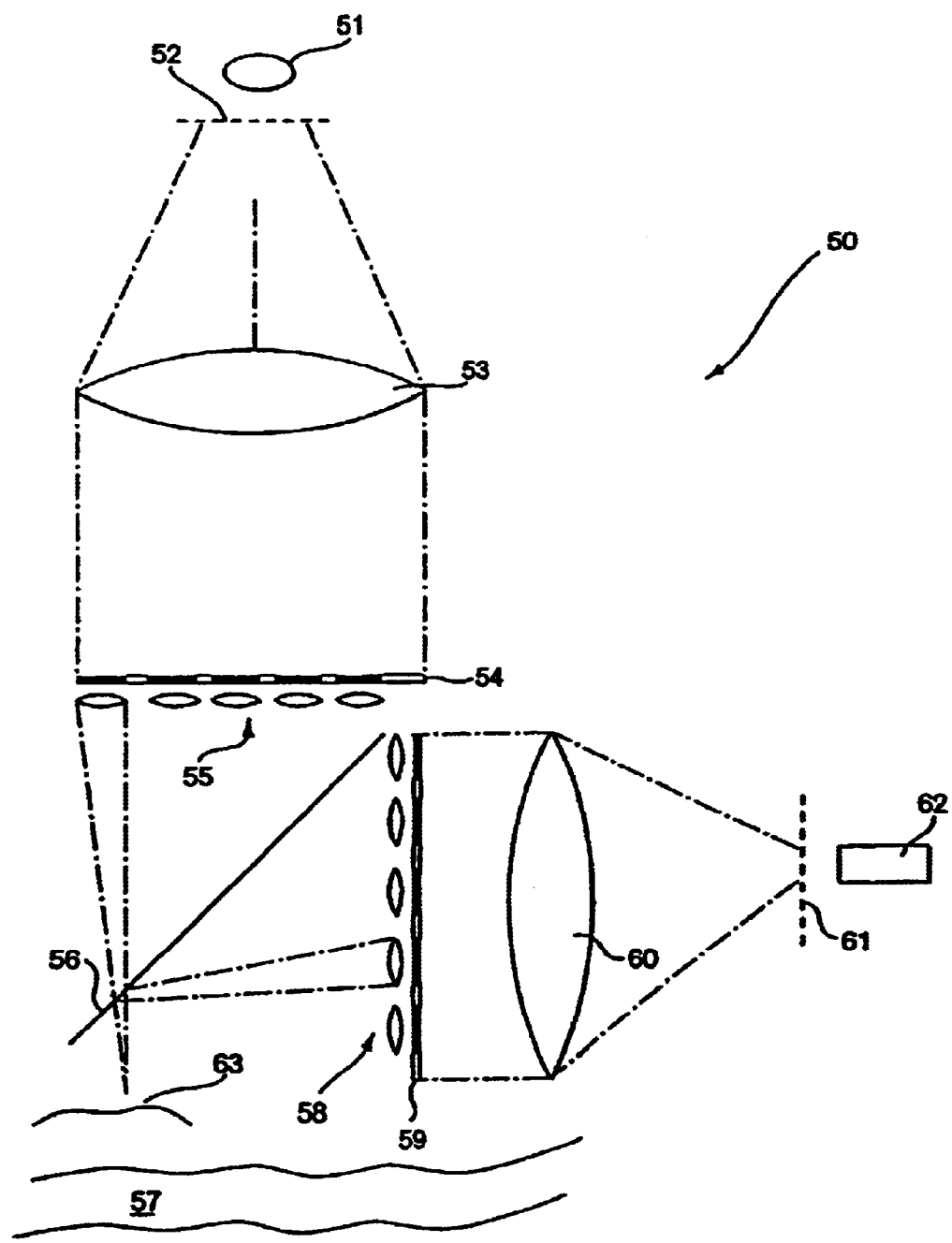
FIG. 4 and FIG. 4A illustrate embodiments of the invention in which separate illumination and detection light valves arrays create arrays of aperture stops, each in conjunction with lens arrays serving as objectives for the illumination and detection optics.

In yet another embodiment of the array volume microprobe, the illuminating and detecting optics are each provided with their own array of optical shutters. In FIG. 4, such an embodiment is shown schematically. Specifically, the array volume microprobe 50 includes a light source 51, a first field stop 52, a collimating lens 53, a first shutter array 54, a first objective lens array 55, beam splitting means 56, a second objective lens array 58, a second shutter array 59, a second collimating lens 60, a second field stop 61 and a detector 62. Not shown in FIG. 4 are appropriate means to image the light source 51 and detector 62 onto their respective field stops 52 and 61. In operation, the light source 51 is imaged onto the field stop 52, having dimensions that are greater than the diffraction resolution limits of the exciting radiation. The light emanating from the field stop 52 is collimated into an essentially parallel beam that impinges on the back side of the shutter array 54. At any given time, only one of the light valves in the light shutter array is opened and its corresponding light valve in the detector shutter array is open. The sequential illumination of an array of volume elements within the sample, in a manner similar to that described above, coupled with the synchronous opening of the appropriate light valve in the detector array, assures that at any given time, only responses from the probed volume element are detected. Similarly, scanning in the x,y direction is provided by controller 18 sequencing the opening and closing of the light valves in the two shutter arrays in synchronism. It should be understood that in this embodiment, the two field stops 52 and 61 are conjugated to each other via each of the volume elements 63 in the sample 57.

Figure 4A:
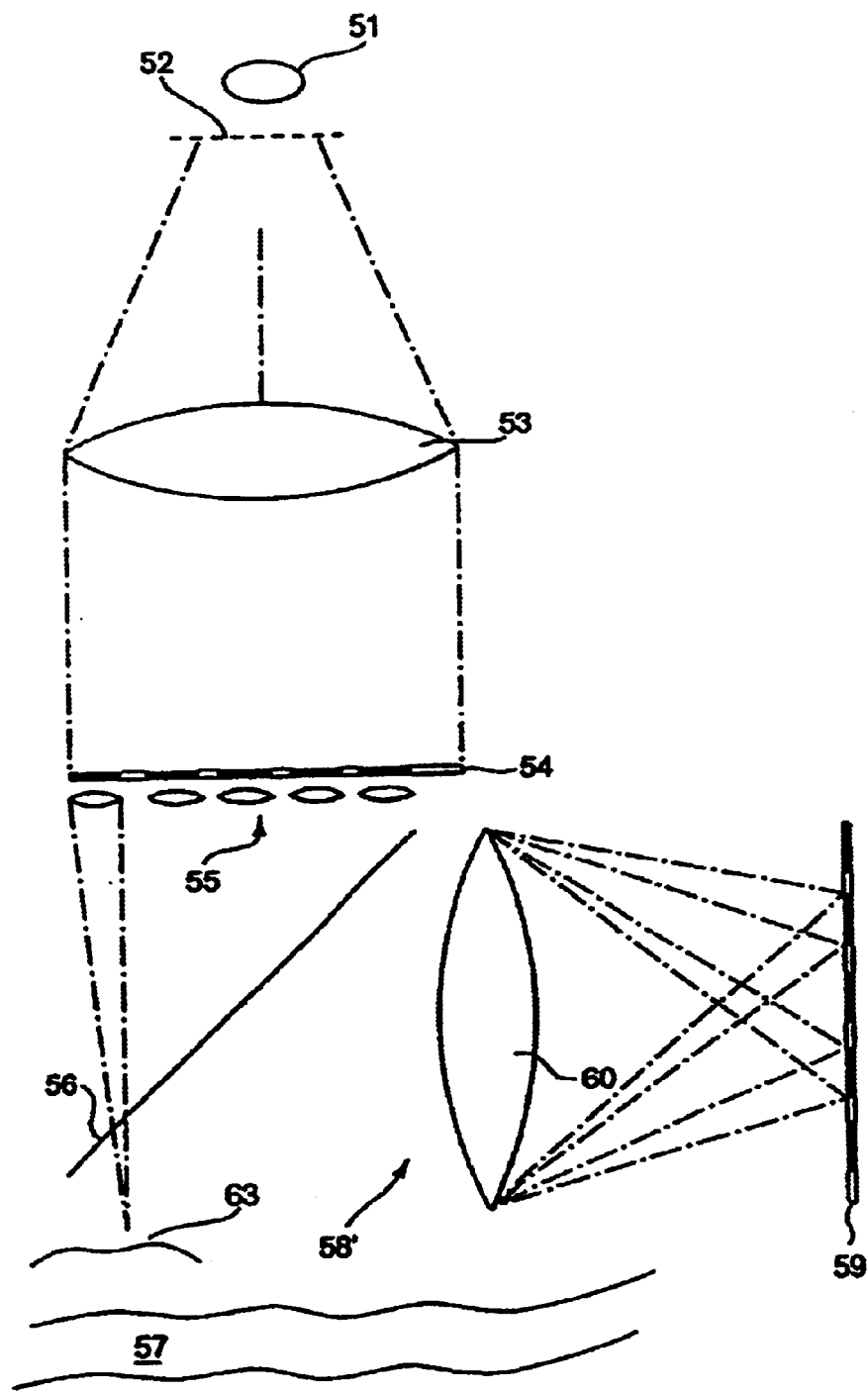

In FIG. 4A, an arrangement essentially identical to that described in FIG. 4 is shown, except that the array of microlens 58 is replaced with a single large lens 58'. Like elements in FIGS. 4 and 4A have the same reference numbers.

Figure 5:
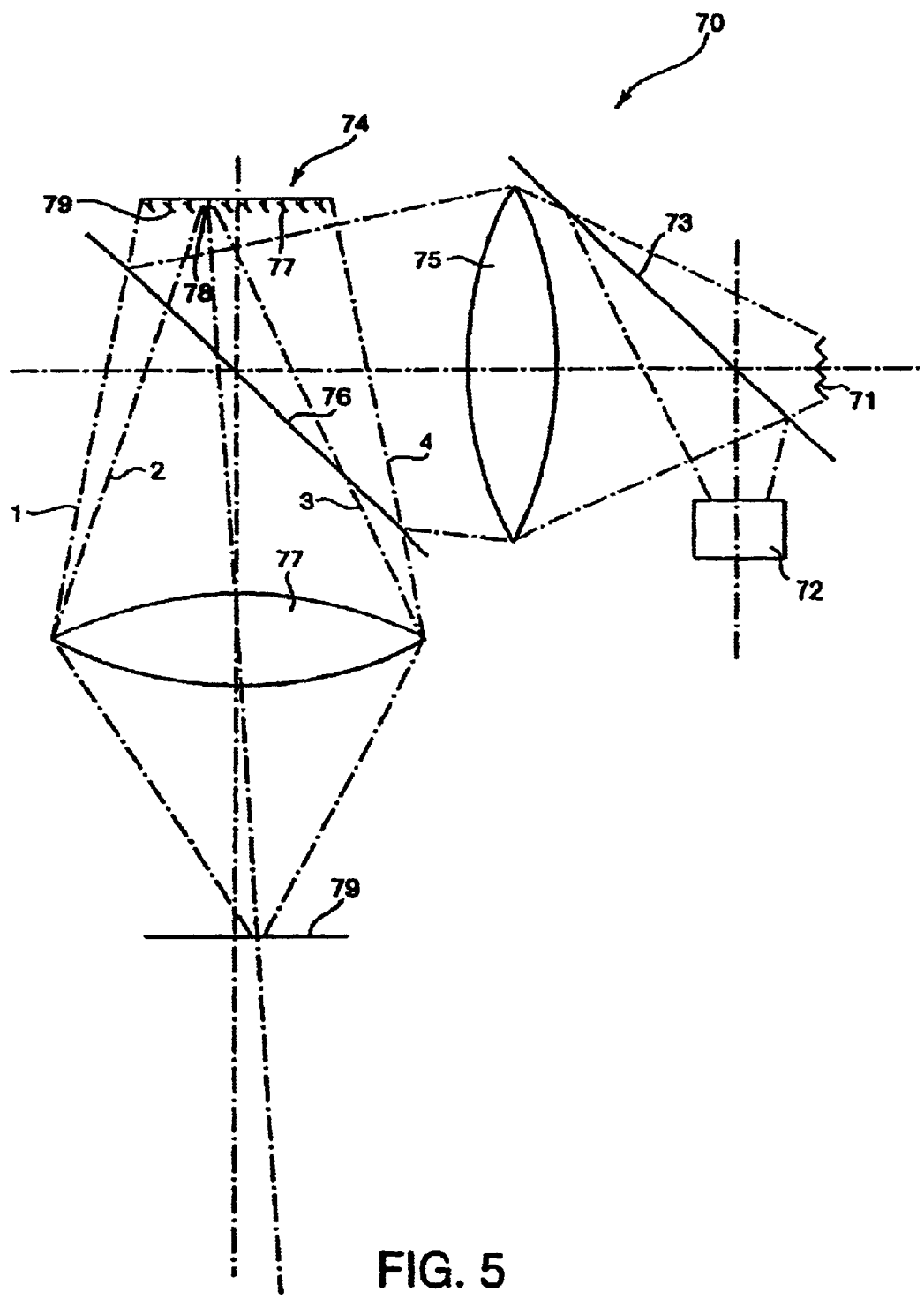
FIG. 5 illustrates an embodiment of the invention in which an array of (deformable) flat micromirrors is used as field stops and the sequential selection of micromirrors serves to sequentially illuminate volume elements in a sample.

Yet another embodiment of the invention is illustrated in FIG. 5, which shows an array volume microprobe 70. The system includes a light source 71 and a detector 72 having their optical axes orthogonal to each other and separated by a first beam splitter 73. The light emanating from the source is condensed onto an array of field stops 74 with a condenser lens 75 and a second beam splitter 76. The array of field stops 74 consists of an array of inicromirrors 77 that may be tilted in and out of a plane generally parallel to the plane of the array. Light reflected from any one of these mirrors, while in the untilted position, is reflected back through the second beam splitter 76 and is imaged onto a sample 79 with an objective lens 77. As shown in FIG. 5, only one micrornirror 78 at any given time is oriented to reflect light onto the sample. All other micromirrors in the array are tilted so that light impinging on them is reflected away from the sample. In FIG. 5, rays 1 and 4 are limiting rays for the total field, and rays 2 and 3 are limiting rays for a single micromirror. In operation, the micromirrors 77 are sequentially brought to the untilted position by the controller 18, and as a result of this sequential untilting of micromirrors, a sequence of responses from volume elements in the sample 79 is recorded in the detector 72. An artificial image from the responses may then be recorded and displayed. As in prior embodiments, probing of the sample with the volume microprobe array in the z direction (depth) may be achieved by either moving the objective lens 77 or the array 74 in the z direction.

The control of the tilting mirror is performed by controller 18, and the tilting mechanism may be implemented in a number of ways well known in the prior art. For instance, the mirrors may be micromachined in silicon, leaving a cantilever in the middle of the back of the mirrors. Two opposing electrodes cause the mirror to tilt about the cantilever due to charging one or the other electrode with a charge opposing the charge on the mirror itself Another method of obtaining tilting mirrors is well known in the art of deformable mirrors, whereby each micromirror is mounted on a bipolar piezoelectric element.

Figure 6:
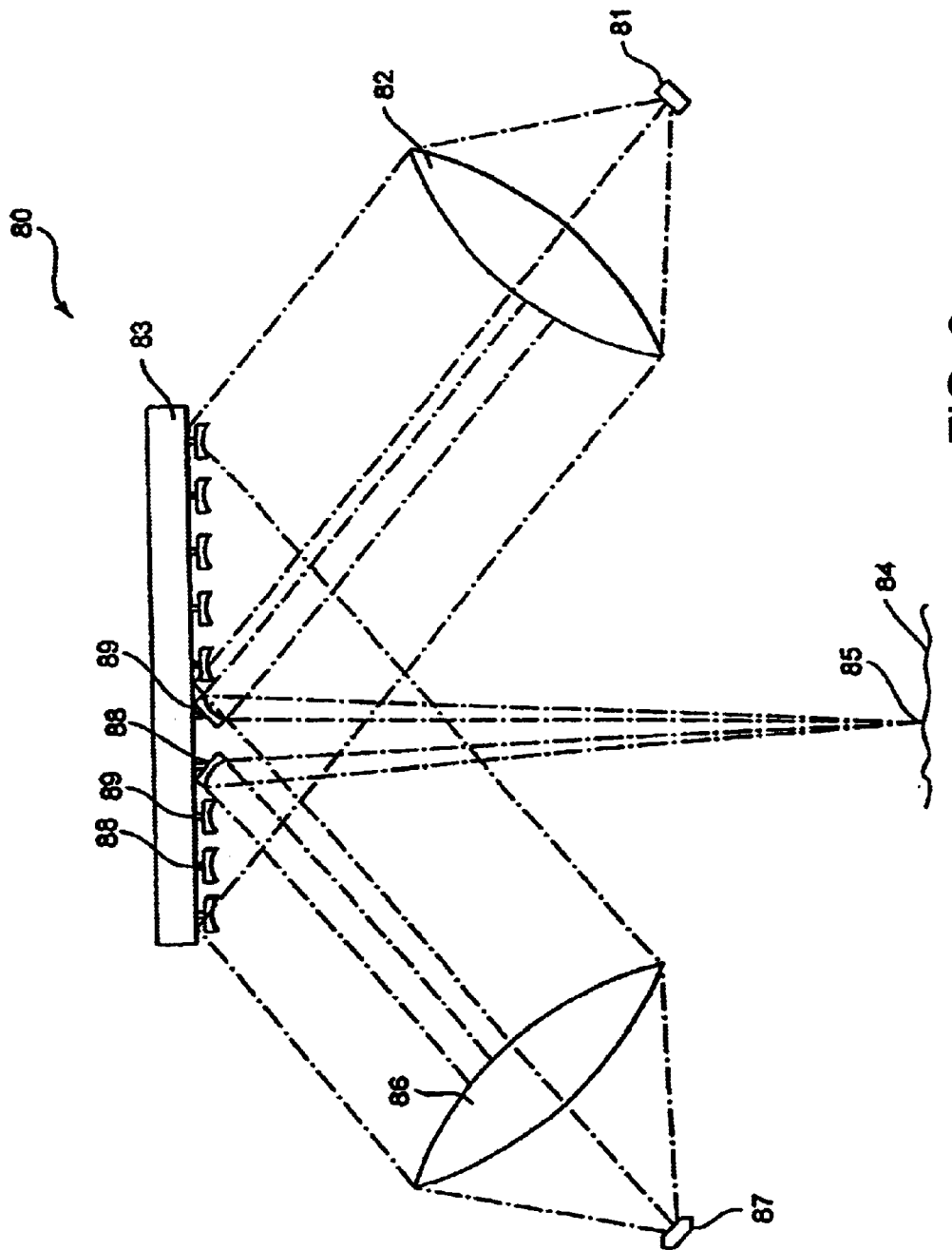
FIGS. 6 and 6A show embodiments of the invention in which an array of (deformable) off axis parabolic mirrors serve as selecting objectives to sequentially apply excitation beams to various volume elements and collect the responses from the volume elements.

Yet another embodiment of the invention, a variation of the embodiment shown in FIG. 5, is illustrated in FIG. 6. An array volume microprobe 80 includes a light source 81 from which light is conditioned to pass through a first field stop (not shown) and through a lens 82. The light is collimated onto an array of micromirrors 83. The micromirrors are tiltable as described above. However, each of the micromirrors is shaped to be an off axis segment of a paraboloid of revolution having its focal point tracing an arc of radius which is somewhat larger than the distance of the array from the sample. The geometry is such that when the mirrors are untilted (parallel to the plane of the array), the axis of the paraboloid of revolution (of which the specific mirror is an off axis segment) is perpendicular to the plane of the array. Thus a line between the focal point (of the paraboloid of revolution) and the micromirror is at a predetermined angle to the normal to the array. The micromirrors may be tilted through that angle so as to bring the focal point of the paraboloid onto the sample.

In one embodiment of the invention, the micromirrors are arranged in alternating right rows 89 and left rows 88 of off-axis segments of a paraboloid. The right mirrors may be termed the exciting mirrors and the left mirrors the detecting mirrors. The focal points of each segment of right rows 89, upon tilting at the above mentioned angle, resides within the sample at the volume element 85, and its respective paraboloid axis of revolution is parallel to the optics axis of the exciting beam, while the tilting in the opposing direction (at the same angle) of each mnicromirror in an adjacent left row causes the focal point of each micromirror to move to the same volume element (85) in the sample 84, and its respective paraboloid axis of revolution is parallel with the optics axis of the detector.

Thus, all mirrors in right rows 89 are used to excite volume element 85 in the sample 84 and all left rows 88 are used to collect responses from volume element 85. In operation, only one pair of mirrors is tilted at any given time and the axes of all other mirrors point down toward the sample. As a result, an exciting beam from the light source 81 is imaged onto the volume element 85, or more accurately, the first field stop is so imaged, while light impinging on all other mirrors is scattered away from the sample in all directions. Similarly, only responses emanating from the volume element 85 are imaged back onto the second field stop in front of the detector. As a result, a very high degree of discrimination is obtained, since the intensity of the exciting beam decreases very rapidly outside of volume element 85, and responses from outside volume element 85 are essentially blocked by the second field stop in front of the detector 87. The controller 18 controls the sequence of tilting each pair of mirrors to obtain an array of responses from different volume elements in the sample. The depth of the volume element in the sample is also controlled by the controller 18 by moving the total array 83 along the z axis toward or away from sample 84.

Figure 6A:
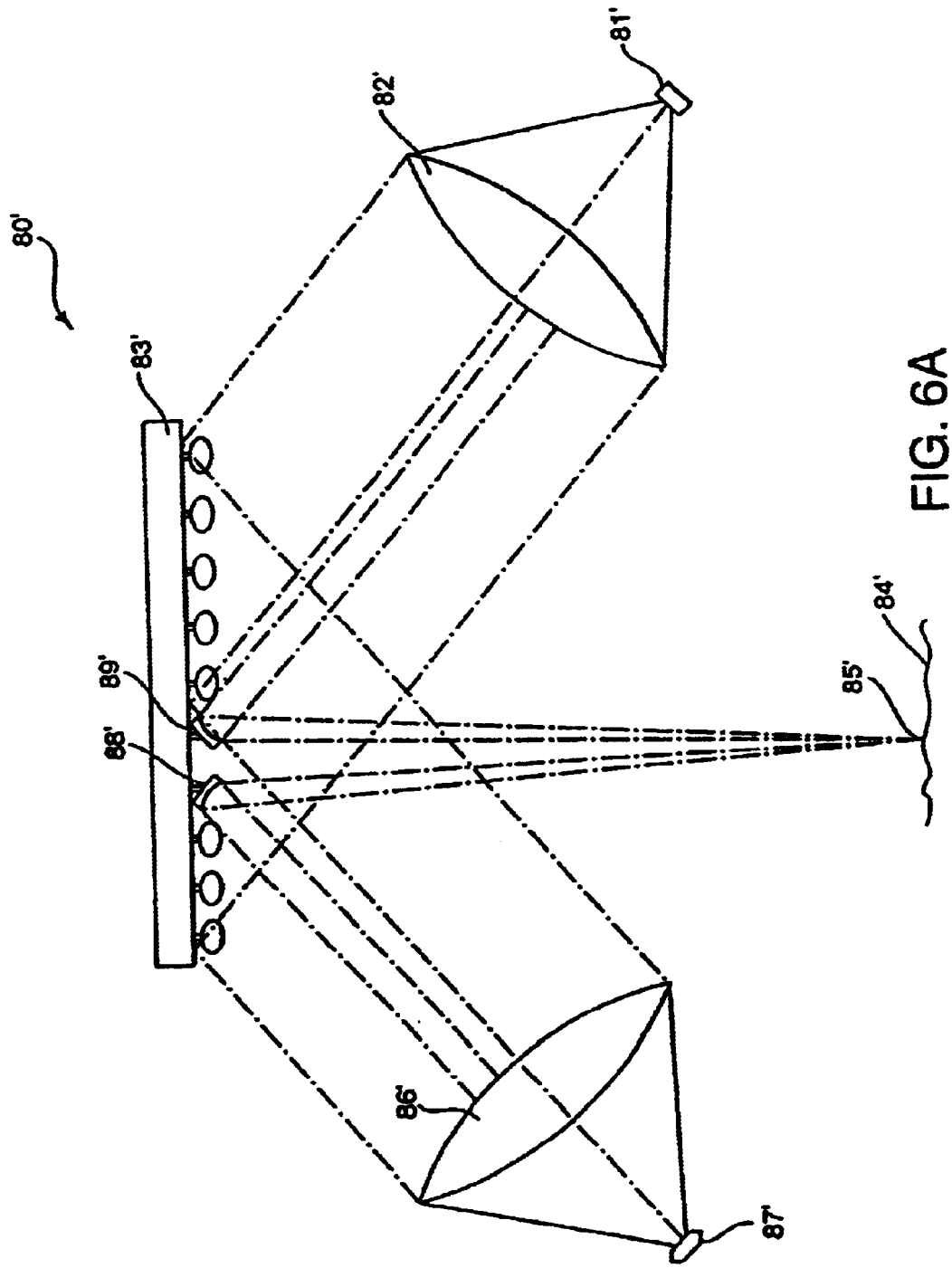

A slightly modified embodiment of the volume probe array shown in FIG. 6 is presented in FIG. 6A. This embodiment allows for using each off axis parabolic micromirror both as an excitation and detection mirror. The system is equivalent to that shown in FIG. 6 and described above, except that the micromirrors of array 83' of the volume probe array 80' are rotated by 90° to the right or the left. Thus, in the unrotated position, the axis of revolution (and thus the optical axis) of each mirror is at 90° to the optical axis of the exciting and detecting optics. However, when a mirror 89' is rotated by 90° to the right, its axis of revolution becomes parallel to the axis of the excitation, and the focal point of the off-axis parabolic micromirror is in volume element 85'. If an adjacent mirror 88' is simultaneously rotated 90° to the left, then its axis of revolution becomes parallel to the detection optics, and its focal point is in volume element 85'. The volume element 85' is determined by the overlap of the images of the two field stops, as explained in detail in U.S. Pat. No. 5,713,364. In this embodiment, as well as the one shown in FIG. 6, sheared conjugation of the excitation and detection optics field stops is used to provide for spatial discrimination of the excitation beam to the target volume element as well as the spatial discrimination of the detected responses to be essentially from each volume element. In operation, the controller 18 causes two adjacent micromirrors (89' and 88') to be rotated simultaneously as described above and thus provides excitation of essentially only the desired volume element 85' and responses which emanate essentially from the volume element 85'.

An advantage of the embodiment shown in FIG. 6A is that a higher resolution of volume elements is feasible for the same density of micromnirrors, since each mirror may be used to either excite a volume element or to collect responses from an adjacent volume element. This differs from the embodiment shown in FIG. 6, where all left mirrors may be used only to collect responses and all right mirrors may be used only to excite volume elements. In the embodiment of FIG. 6, the tilting of the off-axis paraboloids of each segment is in a plane perpendicular to the plane of the array, while in the embodiment of FIG. 6A, the plane of rotation is parallel to the plane of the array.

Figure 7:
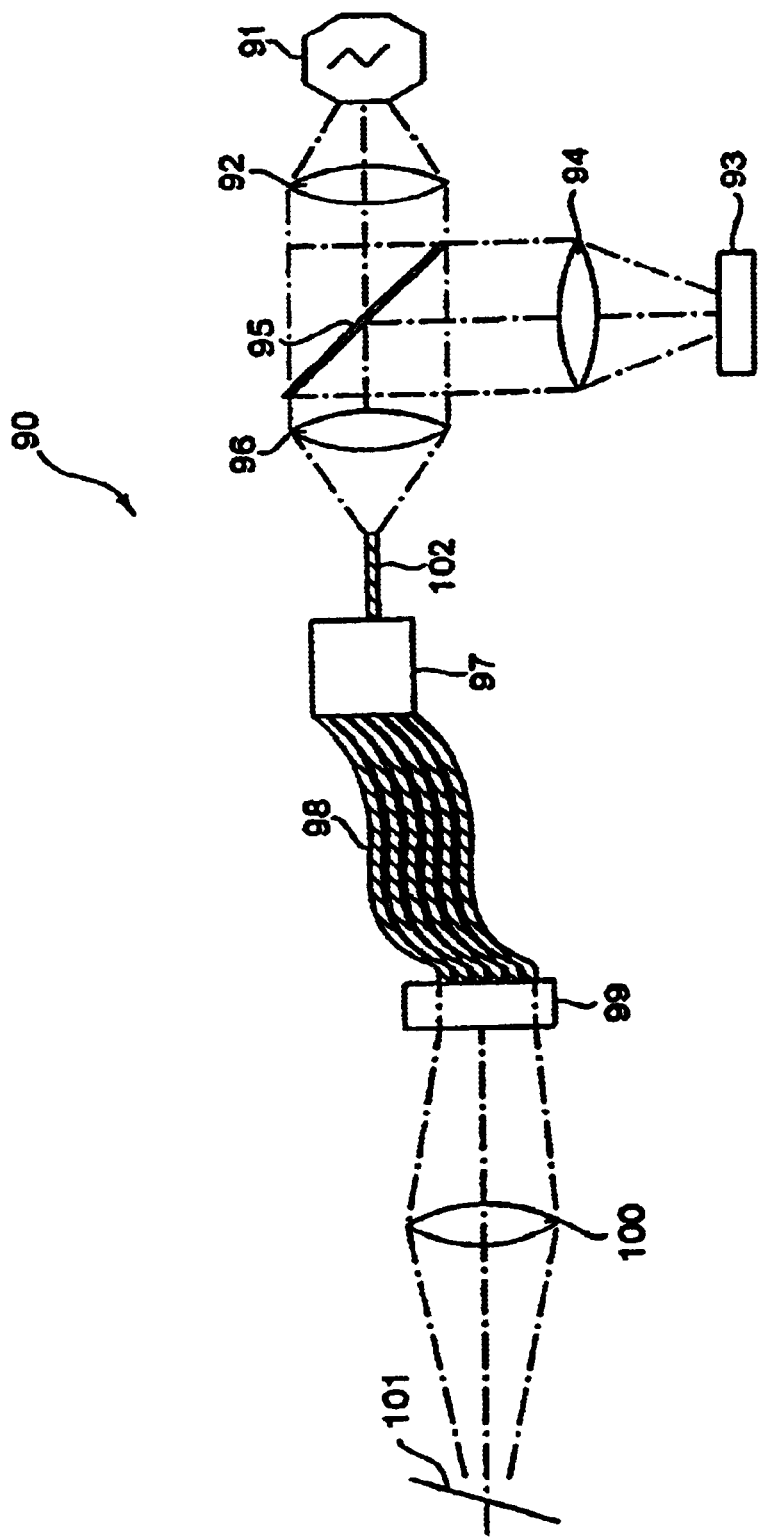
FIG. 7 shows an embodiment of the invention in which the light shutter array is replaced with a fiber switching device to sequentially illuminate (and obtain responses from) an array of volume elements in a target sample.

In FIG. 7, yet another embodiment of the invention is shown. An array microprobe 90 includes an illumination optical assembly with a light source 91 and a first collimating lens 92, and a response collection optical assembly having a detector 93 and a second collimating lens 94. The respective optical axes of the light source assembly and the detector assembly are at 90° to each other. A beam splitter 95 is positioned at the intersection of the exciting and detected beam so as to separate the detected signal from the excitation signal. A lens 96 is used to focus the exciting beam into an optical fiber 102 which is interfaced with a fiber switching element 97. The fiber switching element 97 is terminated on the opposing side with a plurality of fibers 98, and the switching element is capable of connecting optically and sequentially (under the control of the controller 18) the proximal fiber 102 to any of the fibers 98 in the distal bundle. The ends of the individual fibers in the bundle are then arranged in an array 99 (this array may be either a linear array or a two dimensional array). An objective lens 100 then images the respective ends of the fibers in the fiber bundle onto the specimen. Each individual fiber end (within the fiber holder) defines a field stop which is imaged onto the sample. This field stop serves as a field stop to both the exciting beam and the detected responses from the sample. As is described in more detail in U.S. Pat. No. 5,713,364, such an arrangement involves the conjugation of both the exciting and detected optics via the volume elements in which the field stop is imaged, and thus provides for spatial discrimination of both the excitation beam and the responses to be essentially from each volume element associated with each fiber in the array.

In operation, the fiber switching element 97 directs the exciting beam sequentially through all the fibers in the bundle 98. As a result, a plurality of volume elements in the sample 101 (having a distribution corresponding to the array of fibers in the bundle 98) are excited sequentially. Responses are collected through the same field stop (the natural aperture of each fiber end) and are separated from the exciting beam by the beam splitter 95 to be detected in detector 93. In this manner, one obtains responses from an array of volume elements that may then be displayed as an artificial image of the sample. This embodiment has the advantage that a higher intensity of excitation is feasible, since the light source is used sequentially by the different fibers in the bundle.

Figure 8:
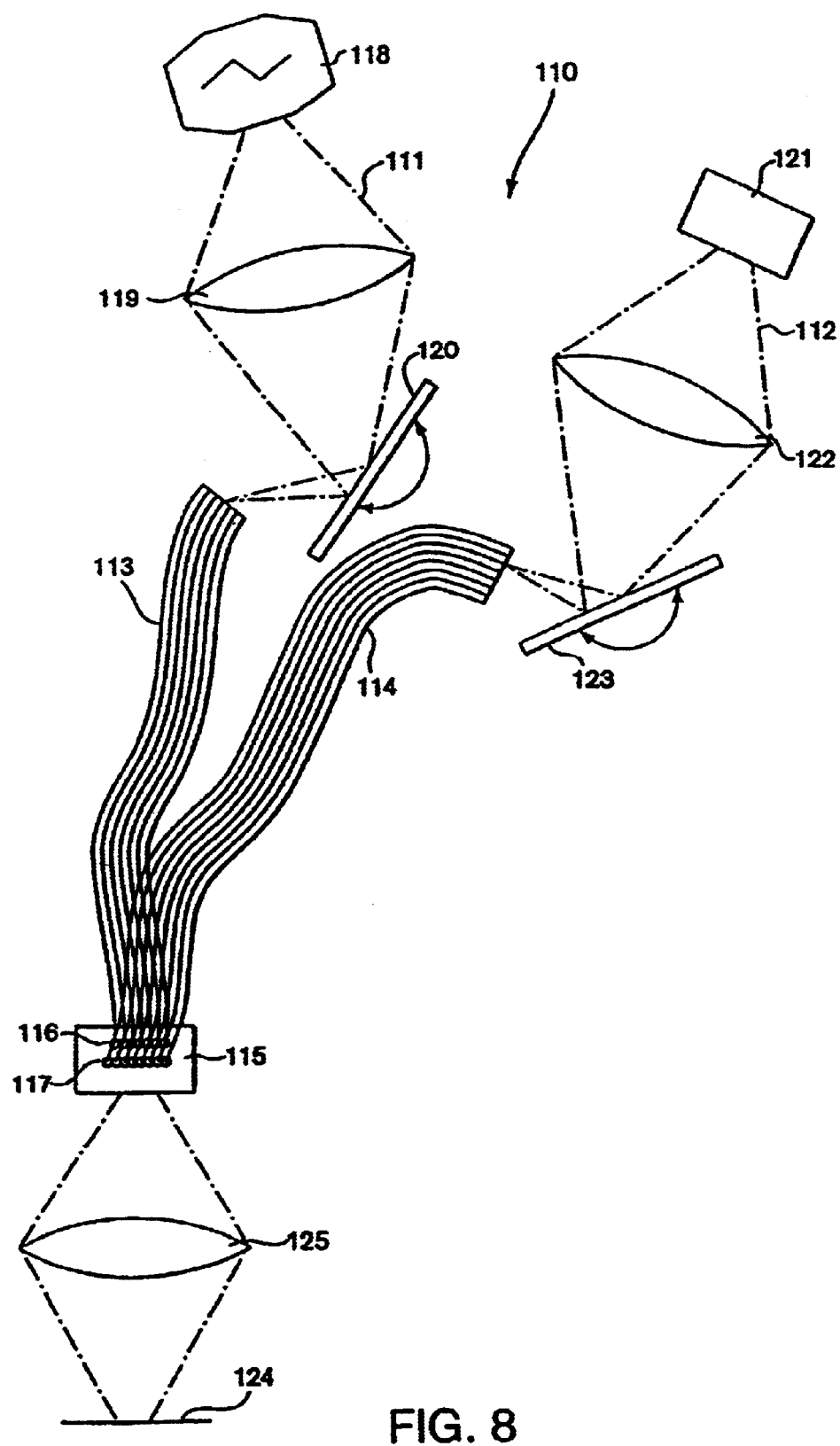
FIG. 8 illustrates an embodiment having two optical assemblies, each coupled to its own (excitation and detection) fiber bundles in which sequential illumination of fibers (and detection) is practiced to obtain data from an array of volume elements.

In FIG. 8, yet another embodiment of a volume microprobe array 110 is shown. The device includes two optical assemblies, an excitation or source assembly 111 and a detector assembly 112. Each of the assemblies is interfaced to its own individual fiber bundle 113 and 114, respectively. The individual fibers are organized, in one embodiment, in two rows 116 and 117, respectively, in a fiber holder 115. When a linear array is desired, the fibers are organized in two opposing rows, one row consisting of the excitation fibers in bundle 113 and the other row of detection fibers in bundle 114. When a two-dimensional array is desired, the fibers are organized in alternating rows of excitation fibers and detection fibers, with a small tilt of such rows relative to each other. The excitation optics 111 includes a light source 118 and focusing optics 119 that may focus the output of the light source on each fiber in the bundle 113 sequentially. A rotating mirror 120 is used to index the light source onto the opening apertures of the fibers in the bundle 113. One should appreciate that the input aperture of the excitation fibers may be terminated in an appropriate way to improve collection of the light from the rotating mirror. Such termination may include, but is not limited to, flaring of the input end of the fiber, or termination of each fiber with a small compound parabolic concentrator, as is well known in the prior art.

In operation, the controller 18 causes the incremental rotation of the mirror 120 so as to direct the excitation beam to fibers in bundle 113 sequentially. This light then emanates through an excitation field stop at each distal end of the fiber, the field stop being essentially the aperture of each fiber. These field stops are imaged onto a sample 124 with objective microlens at the end of each fiber. The distal ends of both excitation and detection fibers are terminated into microlenses that serve as objectives. The excitation and detection fibers may be at a slight angle to each other, and sheared conjugation of their respective field stops (fiber apertures) defines the volume elements probed. The volume elements in the sample will be a mirror image of the fiber arrangement, namely a row or an array of points, depending on the organization of the fibers in the fiber holder 115. The distance between the volume elements may be the same as that between the fibers in the fiber holder or may differ from the interspacing of the fibers in the fiber holder, and will depend on the magnification of a relay lens 125. In some embodiments, one may allow for movement of the relay lens relative to the fiber holder so as to provide magnification (or demagnification). However, the size of each volume element will also be modified somewhat.

This configuration allows for the sequential illumination of an array of volume elements in sample 124. An excited volume element will emit a response to the exciting beam. To ensure that responses that are essentially emanating only from the desired volume element are detected, the responses are collected with a dedicated fiber from bundle 114. The optics are configured such that the respective field stops of the response fibers (their natural aperture) are each conjugated to the respective the field stops of the associated exciting fiber. As a result of this conjugation (or, more accurately sheared conjugation, since the exciting and detecting field stops are slightly spaced apart), the excitation beam has its highest intensity within the sample within the zone of sheared conjugation (the probed volume element), and the intensity declines very rapidly outside the volume element. Furthermore, responses collected by each detection fiber emanate essentially only from the volume element, and any response collected from adjacent tissues is very small relative to the response obtained from the zone of sheared conjugation of the excitation and detection field stops.

Since the excitation of the array of volume elements is carried out sequentially, response will be transmitted through the fiber bundle 114 sequentially to the detecting optics 112. In a preferred embodiment of the invention, the response optics include a receiving rotating mirror 123 which directs (sequentially and in synchronism with the excitation mirror 120) the responses through a focusing lens 122 to a detector 121. This assures that stray responses (namely, responses emanating outside the zone of sheared conjugation and thus outside the target volume element) and collected by adjacent fibers, do not reach the detector. In this manner, as before, spatial discrimination is obtained, and sequential detection of responses from specific volume elements is achieved.

In this embodiment, the use of a beam splitter is avoided, and only very simple optics are used at the distal end of the device. Such a device is particularly suitable when a distance between the sample and the optics (source and detector) is required, such as in laparoscopic and endoscopic devices. This embodiment has the additional advantage that higher excitation energies are feasible, since the light source resources are not distributed simultaneously over a full array as in some embodiments described above, and in this respect is similar to the embodiment shown in FIG. 7 and described above.

Figure 9:
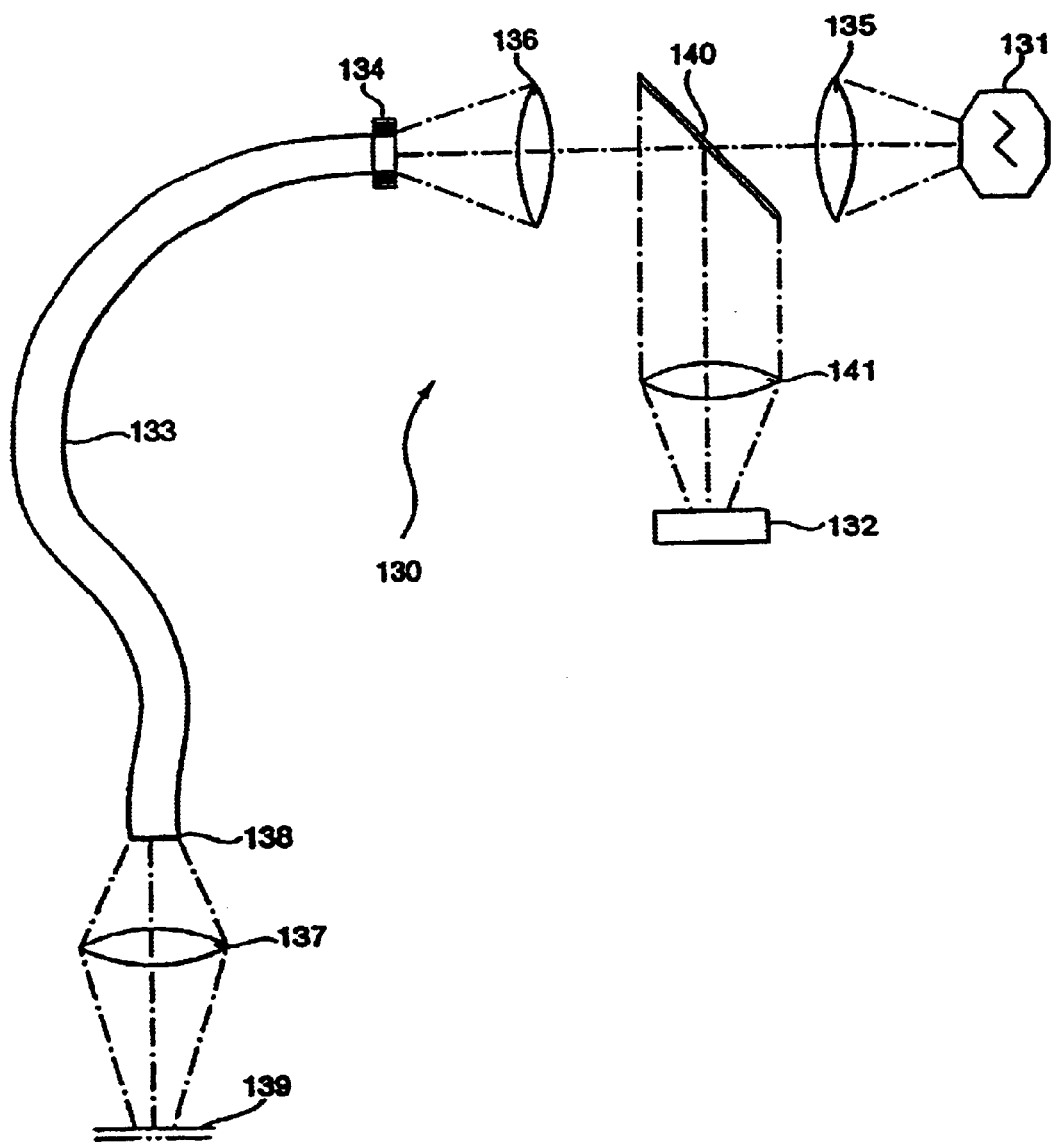
FIGS. 9 and 10 illustrate embodiments of the invention in which light shutter arrays are coupled to optical fiber bundles.
Figure 10:
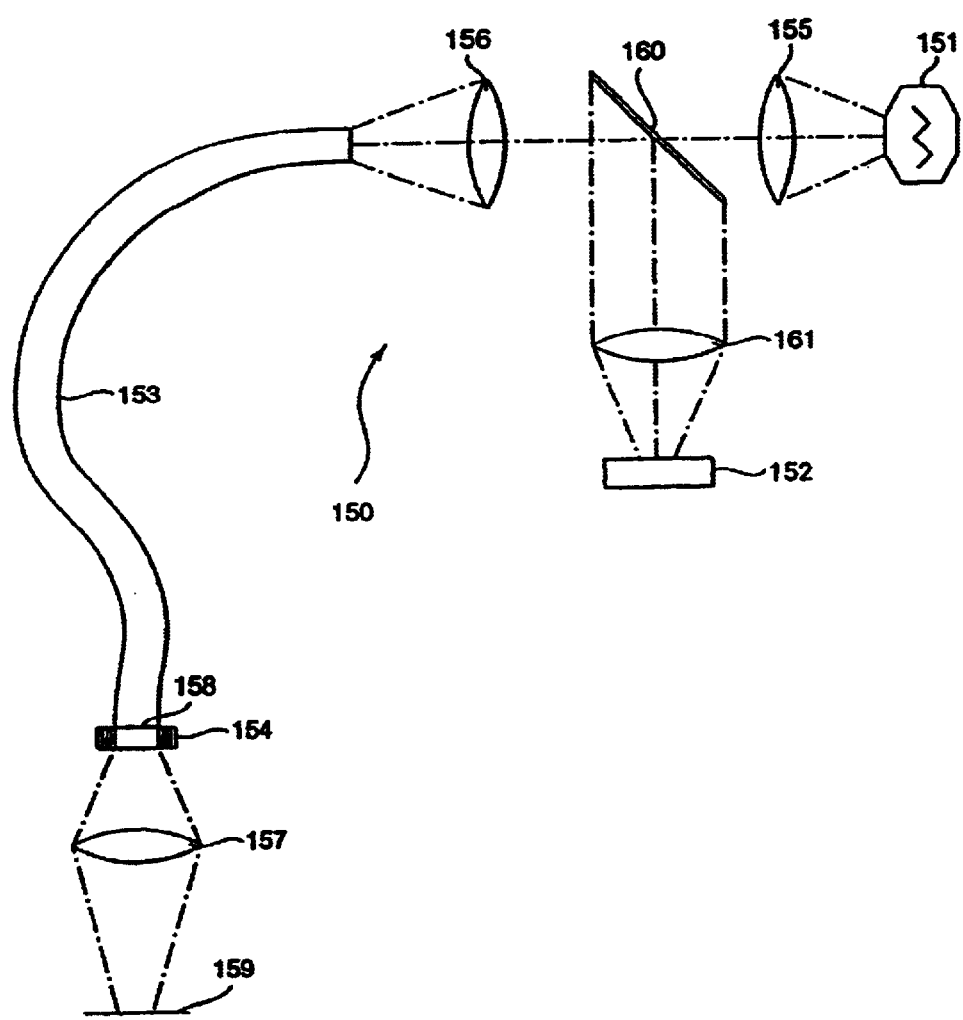

In FIGS. 9 and 10, two additional embodiments of the invention, which differ from each other only in the position in the system of the addressable light shutters, are shown. In FIG. 9, a volume microprobe array 130 that includes a light source 131, a detector 132, and an optical fiber bundle 133 is shown. The proximal end of the optical fiber bundle interfaces an addressable array of optical shutters 134. The optical shutters are under the control of the controller 18. Each fiber in the bundle 113 is positioned in an array arrangement that corresponds to the addressable light shutter jarray. The light source 131 is coupled to the light shutter array via a condenser lens 135 and a shutter array coupling lens 136. As a result, light from the light source is distributed over the light shutter array, and, when one of the shutters is in the open position, light is transmitted to the specific fiber coupled to that specific shutter. At the distal end of the fiber bundle, the device has objective optics 137 which essentially images each of the apertures 138 of the fibers on a sample 139. The distal apertures of the fibers are, in essence, acting as the excitation and detection field stops for each of the volume microprobes in the volume microprobe array 130 of this embodiment. Responses to the exciting signals emitted from volume elements in the sample are collected by the fibers through the same objective optics 137 and the same fibers through which excitation was carried.

Since the field stops of both the exciting and detecting optics are conjugated within the volume element probed, the excitations and responses are limited to the individual volume elements probed by each fiber. In operation, the light shutter array is controlled by the controller 18 to sequentially open the light shutters in front of the fiber bundle sequentially in such as way that only one fiber is powered at any given time. Thus, by the synchronous detection of responses from fibers that are coupled to an open shutter, a full artificial image of pathologies in the targeted sample may be constructed. As in some of the embodiments described above, the response is separated from the excitation by a beam splitter 140 positioned at 45° to the optical axis of the excitation optics and detection optics.

In FIG. 10, a similar volume microprobe array 150 is presented. The essential difference is that a shutter array 154 is positioned at the distal end of the fiber bundle. This allows for selecting an array of field stops determined by each of the apertures within the shutter array rather than by the individual apertures of the optical fibers.

In some embodiments of the volume microprobe arrays described above, a plurality of detectors corresponding to adjacent fu1ll regions of the shutter array are employed. Each detector accepts responses from a subarray of the light shutter array, and thus from the sample. In these embodiments, data collection is accelerated by the simultaneous opening of a light valve in each of the subarrays in the light shutter array and detecting the response in their respective detectors. When using this approach, care is taken to assure that interferences (or noise) from responses outside each specific region are smaller than a preset value of the expected response from the sample in each region.

In several embodiments described above, an array of light shutters is employed to sequence the excitation of an array of volume elements in the sample as well as collect responses from the volume elements. In some embodiments, each shutter serves as an excitation and detection field stop, while in other embodiments other optical elements in the system perform the function of the field stop. Such light shutters are well known in the prior art and have been used in a number of display devices, whereby the sequence of opening and closing sets of optical shutters that are back illuminated provide either a fixed or a time variable image.

The actual embodiments of such shutters in the prior art may take many forms. The most widely used light shutter array is an array of liquid crystal elements having two sheets of polarizer one each on the front and the back of the array.

On each element in the array, a voltage may be applied. When the voltage is sufficiently high, the liquid crystal causes rotation of the plane of polarization of light passing through it. The two polarizers are oriented in such a way that no light passes through an element when no voltage is applied. Thus, the polarizers are cross polarized (their relative orientation is 90°, thus the first polarizer removes all light polarized in one direction, while the second polarizer blocks the light passing through the then inactive liquid crystal element). When a sufficiently high voltage is applied, the plane of polarization of the light passing through the liquid crystal cell is rotated, so that the second polarizer is essentially transparent to the light passing through the active liquid crystal cell. The addressing may be carried out as in the prior art, either as row and columns, so that only the sum of voltages applied to both a row and column is sufficient to cause the desired rotation of polarized light. Since the dimensions of our light shutters are relatively large and the number of shutters small relative to the current practice in liquid crystal display, such addressing is quite sufficient, and cross talk is minimal and insignificant in view of the strong spatial discrimination due to the conjugation of the excitation and detection field stops.

When very large arrays are desired, approaches such as used in active matrix liquid crystals display (namely the activation of a pixel through the direct switching of an individual transistor at each pixel) may be practiced as well.

In yet another embodiment, the shutter array consists of ferroelectric elements activated in a manner similar to that of liquid crystal light shutter arrays. These shutter arrays are useful when the switching rate desired, namely, the rate of opening and closing a given light shutter in the array, is faster.

In yet another embodiment, the light switching medium is a polymer dispersed liquid crystal (PDLC). In such films, a dispersion of droplets of liquid crystal is embedded in a polymer having an index of refraction equal to the field oriented index of refraction of the liquid crystal dispersion. When no electrical field is applied, the droplets are randomly oriented and light is scattered in all directions. Thus the shutter may be considered as closed. When a sufficiently large electric field is applied to a PDLC element, the liquid crystal droplets orient themselves with the field and thus, in the direction of the field, the index of refraction is essentially constant and light passes through uninterrupted. Thus the shutter is open.

In yet another embodiment, essentially electromechanical shutters are used. Such may be easily implemented with piezoelectric bimorphs, which when actuated bend out of the path of the light and when inactive, assume a straight geometry which blocks light transmission through a given shutter.

Figure 13A:
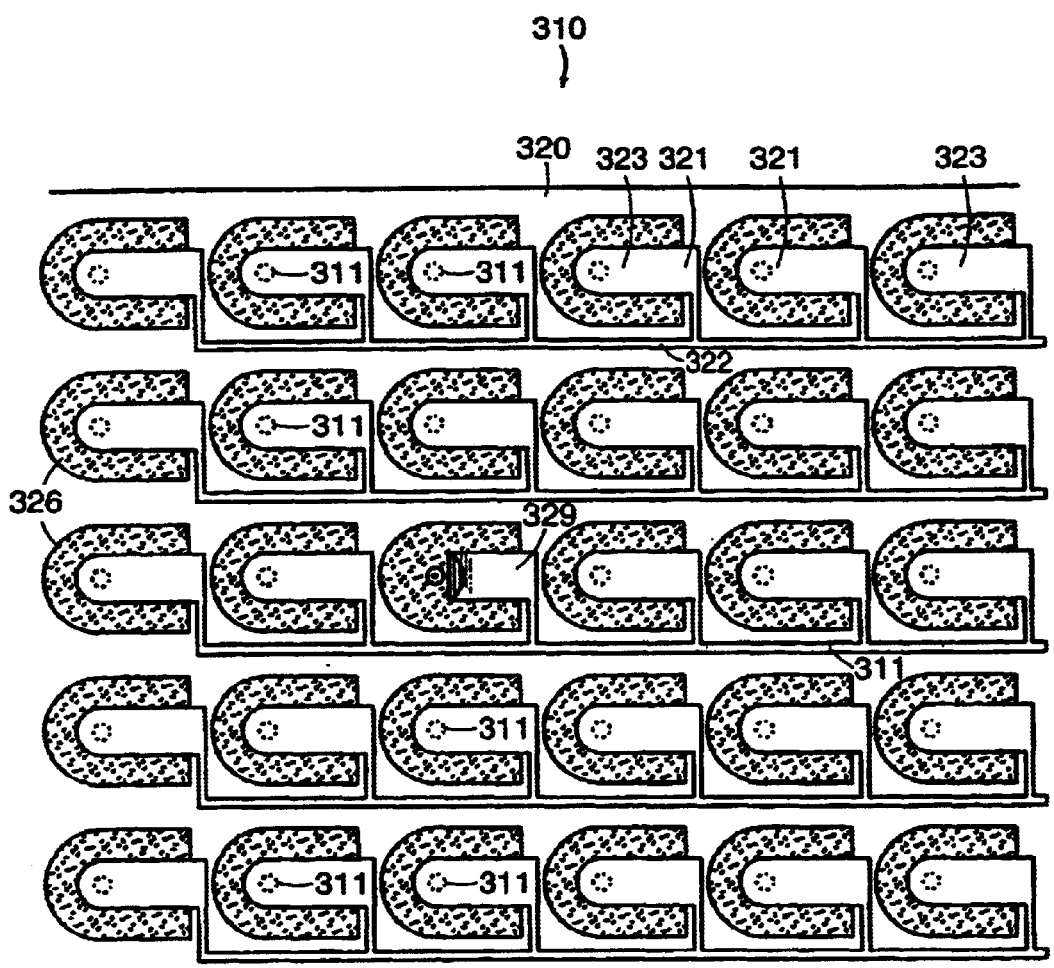
FIGS. 13A and 13B are bottom and top views, respectively, of a partial segment of a PVDF based optical shutter array.

In FIG. 13A a top view of a light shutter array 310 is shown. This shutter array consists of two main elements, a passive base element in which an array of perforations 311 and an array 320 of active flags 321 are provided. The passive base may be made of an appropriate plastic, metal or even silicon. In the present embodiment, the perforations 311 are about 0.1 mm in diameter and are spaced on a grid in which the interspace between the perforations is about 1.0 mm. It should be understood that other dimensions may be selected without deviating from the teachings of the invention. The perforations, which are preferentially slightly conical with their bases at the proximal end and their truncated apices at the distal end, serve as receptacles for optical fibers, each having an external diameter of 0.1 mm.

In production, such fibers may first be inserted and cemented in place, and then the surface of the passive base, with the fibers in place, is optically polished to ensure that the fibers are flush with the distal surface of the base and have an acceptable optical finish. The surface may then be treated with an antireflective coating so as to minimize optical reflections from the distal ends of the fibers, and thus improve both the illumination and signal collection efficiency.

Figure 13B:
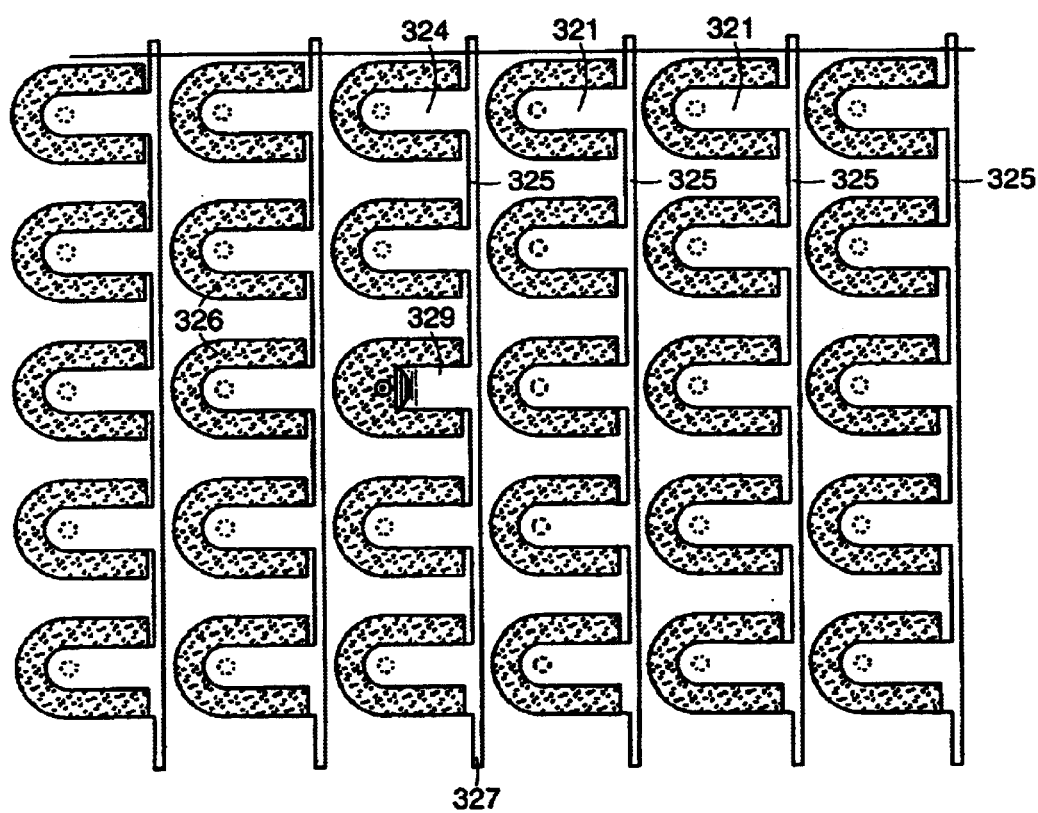

The array 320 of active flags 321 consists of two sheets of piezoelectric material, such as polyvinyl difluoride (PVDF) with metallization on both sides. The two sheets are first cemented together (for instance with an acrylonitrile compound). Then the metallization is etched, leaving a pattern of rows of electrodes 323 interconnected with common leads 322 (in rows) on the top side of the pair of PVDF sheets as shown in FIG. 13A. The electrodes 323 have the same geometry as the flags 321, or may be just a little smaller than the flags. In FIG. 13B, the bottom side of the array 320 of active flags 321 is shown. The metallization of the bottom side is etched to provide second electrodes 324 for each flag, which are interconnected with leads 325 in columns. After both sides of the paired PVDF sheets have been treated to leave rows of electrodes on one side and columns of electrodes on the opposite side, the flags are formed, the electrodes being congruent on both sides (overlapping but ispaced apart by the two sheets of PVDF). The array of flags 321 is created by punching or etching horseshoe-like perforations 326 around each of the metallized pairs of opposing electrodes in the array. It should be apparent to a person trained in the art that one may choose to first form the flags and then etch away the excess metallization between the rows and columns of electrodes.

In operation, the application of a voltage to a row of top electrodes 323 through the common lead 322 causes the top half (formed by the top PVDF sheet) of the flags 321 in that row to become shorter than in their respective unpowered state, while the application of a similar voltage (but of opposite polarity) on a column of bottom electrodes 324 via common lead 325, causes the bottom half (formed by the bottom PVDF sheet) of the flags 321 in that column to become elongated relative to their unpowered state. Assume that the appropriate voltages are applied to a specific row through conductor 328 and none other, and to a specific column through conductor 327 and none other. The flag 329, which is the only flag at that time having both its top and bottom electrodes powered, has on its top portion a voltage that causes its top half to shorten and has on its bottom portion a voltage that causes its bottom half to elongate. As result, flag 329 bends upward and exposes the perforation under it, allowing illumination to reach the sample and allowing responses from the sample to reach the aperture of the optical fiber and thus be transmitted to the sensor. All other flags in the row powered by the row conductor 328 are devoid of voltage on their respective bottom electrodes, and, similarly, all other flags powered by the column conductor 327 are devoid of voltage on their respective top electrodes. Thus, only the flag 329 powered simultaneously by the row conductor 328 and the column conductor 327 is forced to bend upward. One may therefore actuate the flags 321 in a PVDF optical shutter array by applying an appropriate voltage to a given column and sequentially apply voltage pulses to the rows, or one may randomly activate a flag by applying the appropriate voltages to its coordinate row and column.

Figure 14:
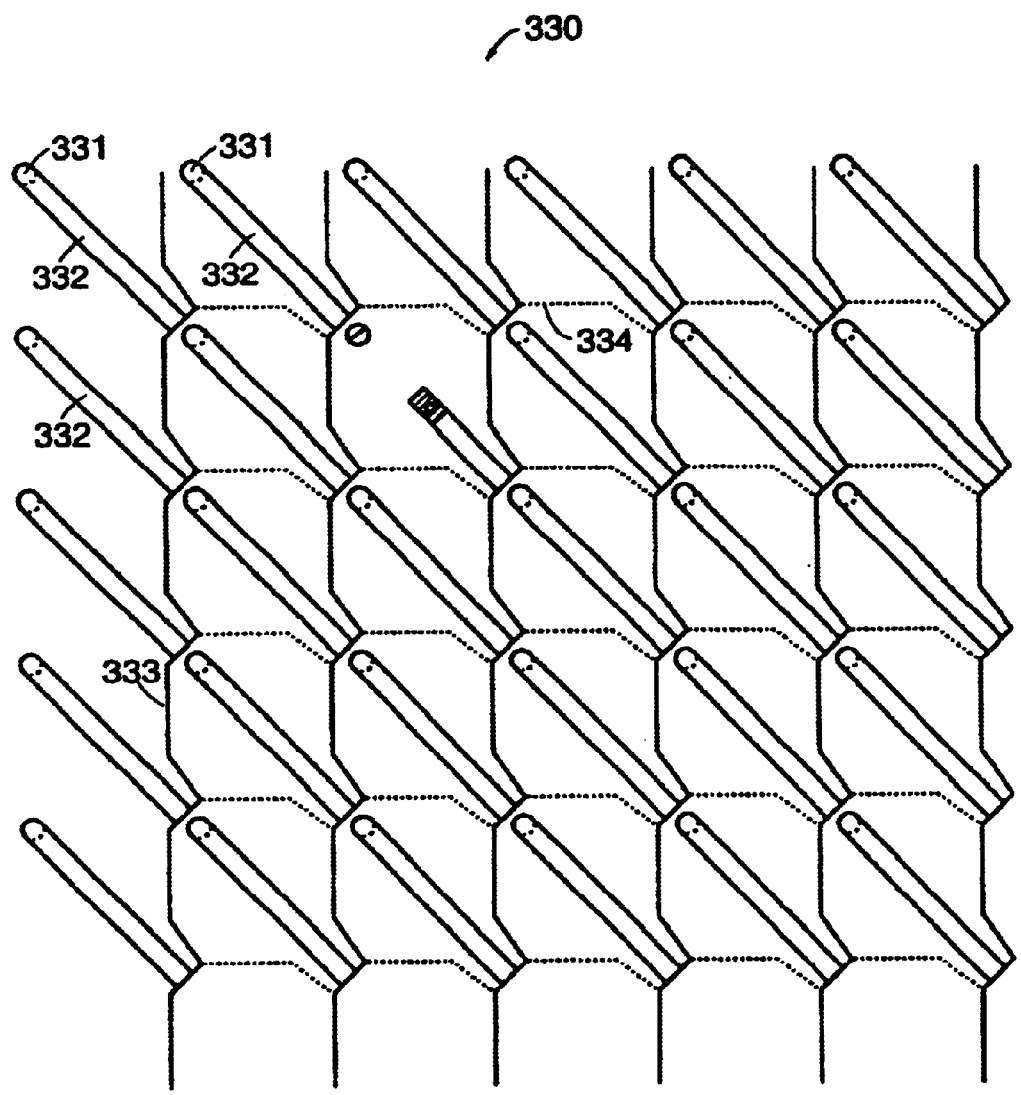
FIG. 14 shows another embodiment of a PVDF based optical shutter array.

In FIG. 14, a variation of a PVDF based optical shutter array 330 is shown. PVDF flags 332 are structured in a similar fashion to the system shown in FIGS. 13a and 13B and described above. Specifically, two sheets of PVDF are cemented back to back, and flags 332 are formed with electrodes on both sides connected on the top side in columns with leads 333 and connected on the bottom side in rows with leads 334. This assembly is overlayed on a plate having an array of perforations 331. The flags are oriented at 45° to the main lattice to allow for a greater movement of the flag. This is important when the fibers have very large numerical apertures and the beams emanating from the fibers. spread at a high angle, and the collection angles of responses from the sample are similarly large. The operation of this array follows the principles described above. In particular, the application of a driving voltage to a given column and a given row causes the actuation of the flag on that column and row.

These are just two examples of embodiments of an optical shutter array in which the actuation of the optical shutters is based on movement induced by piezoelectric bimorphs. In another arrangement, the bimorphs are arranged in rows perpendicular to the base surface of the array, and each bimorph has a flag (parallel to the plane of the array and thus perpendicular to the bimorph) covering its respective perforation in the array. The actuation of each bimorph causes movement parallel to the array surface rather than above the surface. This embodiment is somewhat more difficult to implement, but has the advantage that smaller bending of the bimorph is required, particularly when the optical fibers used in the array possess a large numerical aperture.

Figure 15:
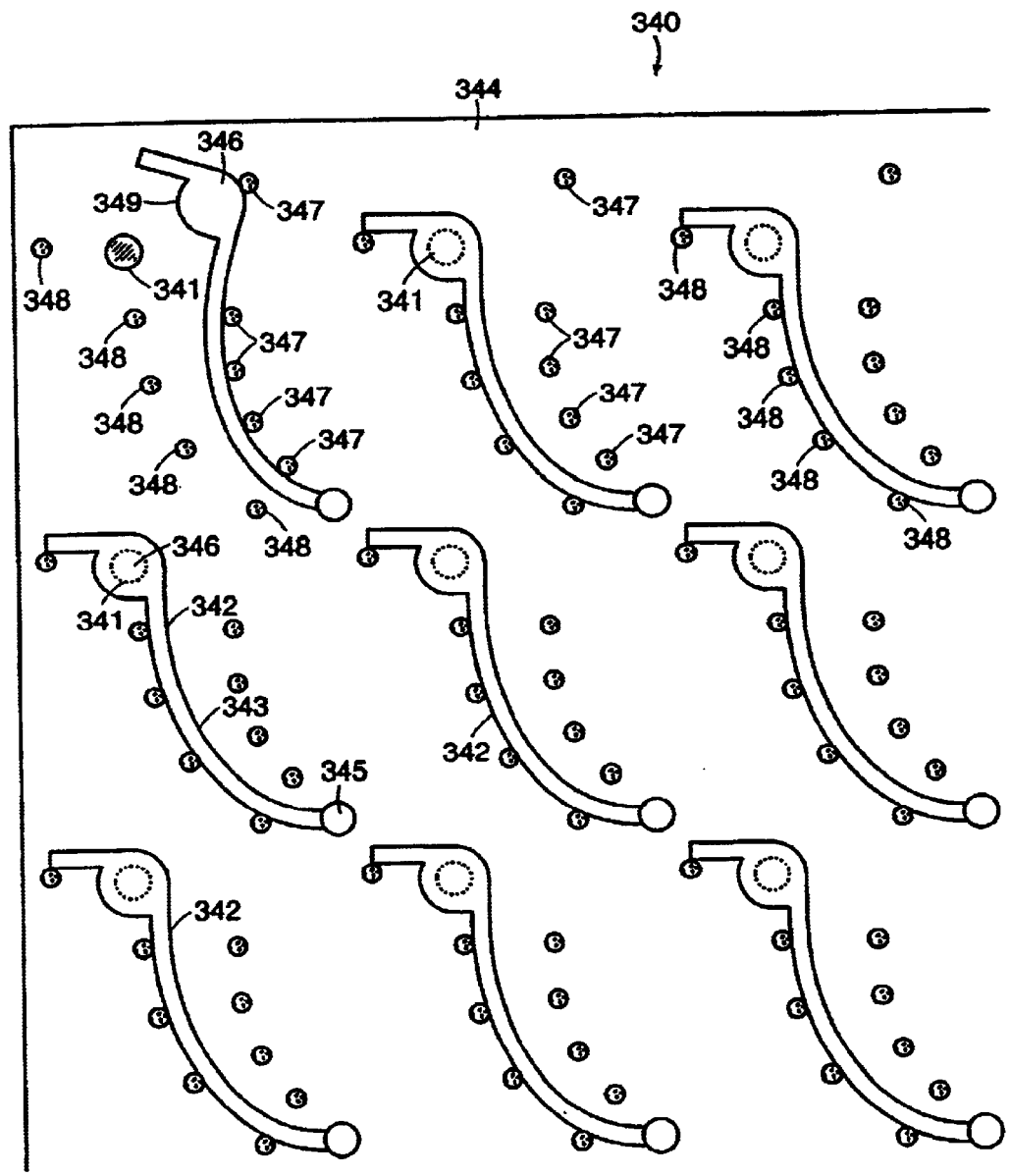
FIG. 15 is a top view of a micromachined optical shutter array.

In FIG. 15, yet another embodiment of an array of optical shutters is shown. In this embodiment, the array 340 is best produced by techniques of micromachining from silicon wafers. While a certain order of description of the various elements in the array is followed below, this order is not necessarily the order used in the micromachining process. Perforations 341, through which optical fibers are inserted, are provided in an array. In this embodiment, these perforations are about 0.1 mm in diameter and are spaced on a grid of 1.0 mm spacing. Each perforation is associated with its own shutter 342. The shutter 342 consists of a thin flexible arm 343 anchored on one side to the base plate 344 via an axis 345. On the opposing side of the arm, a flag 346 is provided. The flag is sufficiently large to cover its respective perforation 341 when the shutter is in the closed position. Two series of posts 347 and 348 positioned on opposite sides of the arm 343 are connected to appropriate electrical leads (not shown). Similarly, the shutter element is connected to its own electrical lead (not shown).

There a large number of possible variations of this embodiment, and a few of these variations are described here. In one embodiment, the total array of optical shutters is manufactured monolithically from a single wafer. In that case, the arm and flag are machined to be in the "open" position 349. Otherwise, it becomes impractical to etch the perforations. In other embodiments, the array is produced firom two pieces cemented together. One piece may contain the array of arms, and the other piece may contain the array of perforations. Then it is preferred to have the rest position of the arms in the closed position. The groups of posts 347 and 348 may be on either of the two wafers, but for practical reasons it is preferred to produce them on the array of arms. It is also possible to provide a single well-positioned post for the group of posts 347 and a single well-positioned post for the group of posts 348. The choice of the specific design depends on the dynamic response required from the light shutters in the array.

The operation of the arm as a light shutter is based on the electrostatic attraction and repulsion generated by the charging and discharging of various members of the assembly. In operation, the arm may be charged, for instance negatively, and the distal posts 347 may be charged positively to cause the arm to be attracted to this set of posts. To accelerate this action, the proximal posts 348 may be charged negatively to cause simultaneous repulsion of the arm. It should be understood that actual contact of the moving arm with either group of posts 348 or 347 is not required. It is preferred to actually avoid such contact and in order to accomplish this aim, the whole assembly may be treated to have a thin layer of silicon oxide as an insulation, thus avoiding such contact.

To facilitate the driving of the shutter array, it is preferred to apply the activating voltages in rows and columns, and only the simultaneous actuation of a given column and a given row causes opening of the shutter at the intersection of the selected row and column. This may be achieved in a number of ways. Consider the case where the device is made of two independent wafers, so that the rest position of the arm may be in the closed state. Thus, when no charges are present on the arm, the optical shutter is closed. Referring again to FIG. 15, apply a pulse charging all the arms in the first row negatively, and through the pair of leads for the first column, a positive charge is applied to the posts 347 and a negative charge is applied to the posts 348. The negatively charged arm in the first row and the first column is repulsed from the negatively charged posts 348 and is attracted to the positively charged posts 347, thus opening the optical shutter previously covered by the flag 346. The other arms in the first row are unaffected, since their respective posts 347 and 348 are uncharged. Similarly, all arms in the first column are uncharged and thus, despite the fact that the posts 347 and 348 are charged, the arms do not move, thus leaving the optical shutters closed. When scanning the whole array, all arms 343 in a given row may be kept charged and the posts in adjacent columns may be sequentially charged.

The return of the arm to its closed position may be achieved either through the spring forces in the arm or actively by reversing the charges on the posts 347 and 348. The selection of a passive return or an active return to the closed position is determined by the dynamics of the scanning process. When extremely rapid scanning is desired, reversal of the charges on the posts is preferred, but when the dynamic response may be slower, mechanical relaxation to the rest position may be practiced.

Figure 16:
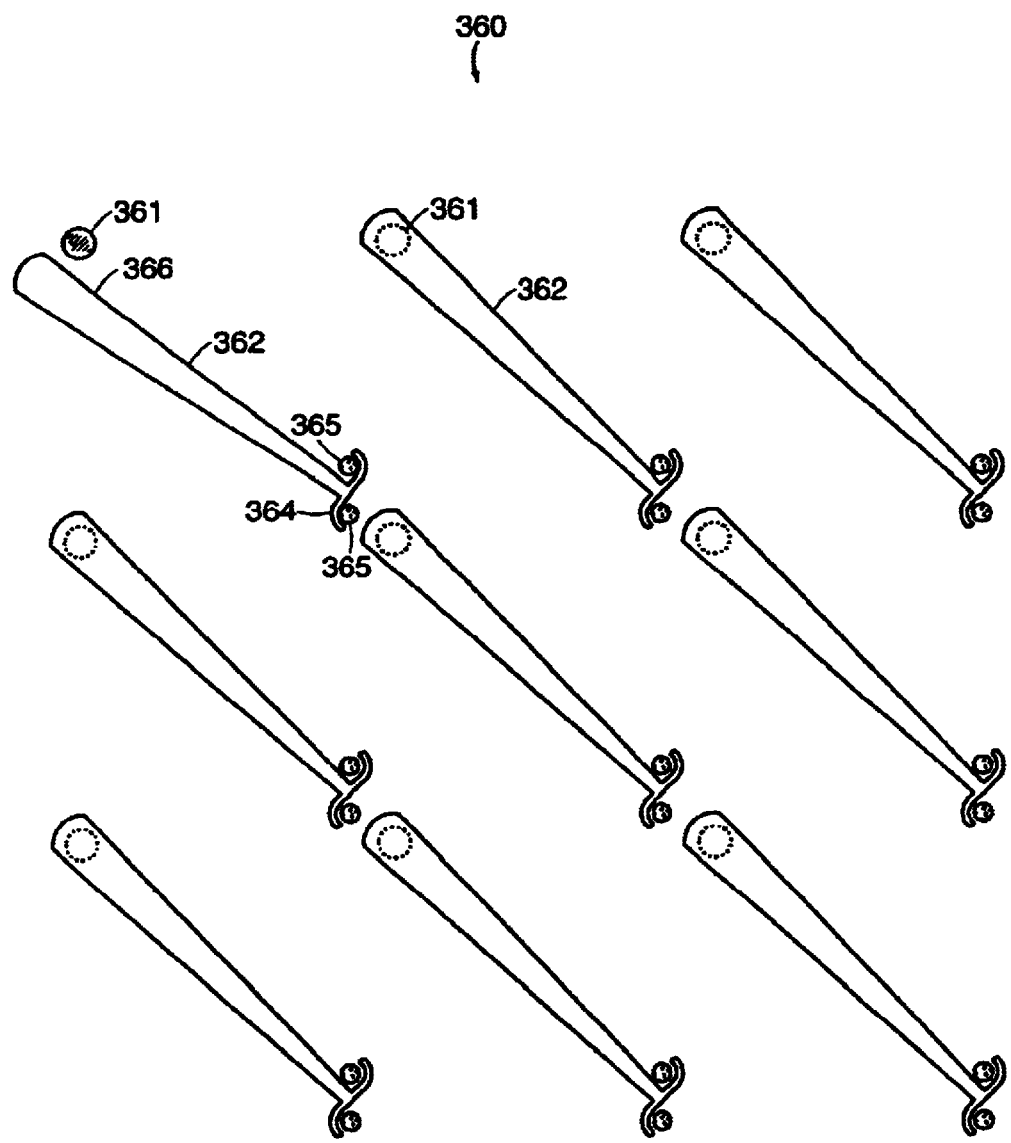
FIG. 16 shows another embodiment of a micromachined optical shutter array.

In FIG. 16, another embodiment of a micromachined optical shutter array is shown. Here, as in FIG. 15, the array may be monolithically produced or may be assembled from two sub structures. In the base plate, an array of perforations 361 having a diameter of about 0.1 mm spaced on a grid whose points have 1.0 mm spacing is provided. The active elements comprise flat arms 362 attached to the base plate with a twistable post around which the arm may rotate. The distal end of the arm is sufficiently broad to cover the perforations and thus block the optical path to the fibers that are mounted within the perforations. While in FIG. 16 arms having their width gradually expanding to cover the perforation 361 are shown, it should be understood that a narrow arm 362 terminated by a wide flag at its distal end, sufficient to cover the perforation, may be provided.

The proximal end of the arm is terminated with a structure 364 generally perpendicular to the axis of the arm. Two posts 365 protrude from the base plate, positioned somewhat apart from the structure 364. When the arm is, for instance, charged negatively, and the posts 365 are charged positively, the electrostatic attraction causes the arm to rotate and expose the perforation, thus opening the optical shutter as shown in position 366. Here as above, the array may be operated by maintaining a given row (charging the arms 362 in that row) negatively and scanning the column, which positively charges all pairs of posts 365, to obtain sequential opening and closing of the optical shutter array. As above, the elastic properties of silicon may be relied upon to return the arm to its rest position (through the twisting base 363 spring action), or the charge on the pairs of posts may be reversed before switching to the next column.

A variety of light sources may be used in conjunction with the array volume nmicroprobes of the present invention. For instance, when the desired responses are fluorescence responses, one would often use a laser source, such as a nitrogen laser having a wavelength in the ultraviolet part of the spectrum, such as 337 nanometers. When backscattering as well as absorption in a broader part of the spectrum is the desired response, the light source is usually a broad spectrum source such as, but not limited to, a xenon discharge lamp, a halogen incandescent lamp, or any other suitable broad spectrum light source. Furthermore, such a light source may be conditioned with an appropriate filter to homogenize or otherwise modify the light spectral distribution. The use of more than a single light source in a given system is also contemplated. Thus a volume microprobe array may include a UV laser source to perform fluorescence measurements, as well as a wide band light source to perform scattering and absorption measurements. A third light source particularly rich in near infrared radiation may be included as well. In operation, these light sources may be directed toward the excitation optical assembly in a predetermined sequence. For instance, a typical UV laser source would operate in a pulse mode having a relatively short duration pulse (for instance under a microsecond) and a slow repetition rate. Thus a lapse time between excitation of milliseconds or fractions thereof (often done to avoid overheating of the laser source) is available between measurements of fluorescence responses. During this lapse time, a broadband light source may be directed at the excitation optics, and measurements of the response of the target sample to that second light source may be detected.

Furthermore, to obtain additional diagnostic and analytical information from the volume elements probed, one may obtain Raman scattering data which provide molecular structural information on the material probed. The light source or excitation beam may then be a laser within the visible range of the spectrum. When it is desired to reduce the fluorescence signal generated with an intense beam in the visible part of the spectrum (which masks the much weaker Raman scattering responses), one may use a laser in the far red or the near infrared part of the spectrum. Such light sources may be a HeNe laser at 633 nm, or a GaAIAs diode or laser diode at 783 nm or even a Nd:YAG laser at 1064 nm, as well as other near infrared diodes or laser diodes. In some embodiments of the invention, when multiple light sources are used, multiple detectors may be used as well. Each is designed to be optimized for the spectral response and response intensity anticipated. In such cases, the timing of the excitation from the plurality of sources and the responses from their associated detectors is controlled by the controller 18.

Figure 11:
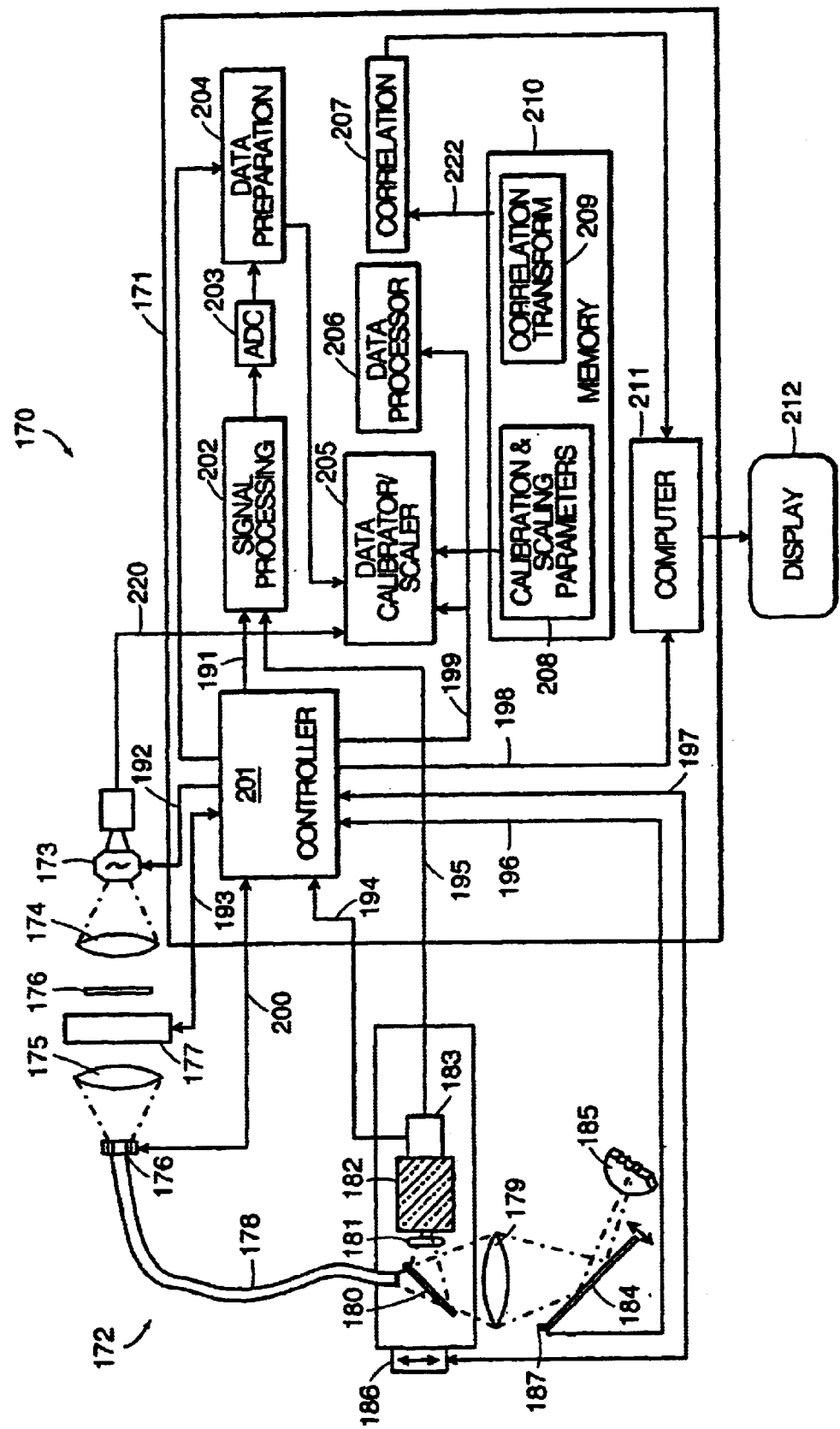
FIG. 11 is a schematic representation of one of the embodiments of the invention, including a block diagram of the control and data processing elements of the system.

In FIG. 11, a typical volume microprobe array 170 with its associated electronic modules and computing modules is shown. The optical system is similar to that shown in FIGS. 9 and 10 and described above, except that the beam splitter is positioned at the distal end of the optical fiber assembly, and in lieu of using the light shutter array for both the excitation and detection optics, an array of detectors is used for the spatial discrimination of the responses, rather than an array of light shutters. Specifically, the volume microprobe 170 includes a data processing and system control unit 171 and an optical system 172. The optical system includes at least one light source 173. Lenses 174 and 175 are interposed between the light source and a light shutters array 176 so as to image the light source onto the array. Interposed between lens 174 and 175, a device 176 may be included to condition the spectral distribution of the light source. Such a device may be a filter that is designed to modify the normal spectral distribution of the light source, which may include parts of the spectrum at intensities that are greater than other parts, and thus normalize the spectral distribution of the exciting beam. The element 176 may be a plurality of filters mounted on a rotating filter wheel, so as to interpose different type of filters (or no filter) in the exciting beam path.

Also interposed between the two lens 174 and 175, a second device 177 may be included to modulate the exciting beam in time and in intensity. Such a scheme may be used to improve the signal-to-noise ratio of the detection system by synchronizing the modulation and detection through an appropriate phase locked amplifier (not shown), which is part of the electronics system 171 (indicated as control arrows 191 and 193). Similarly the timing of the light source 173, including the sequencing of a plurality of light source or the pulse rate and pulse width of a UV laser source, is also under the control of the controller 201 as indicated by the control arrow 192. The light shutter array 176 is coupled to an optical fiber bundle 178 in such a manner that each fiber within the bundle is coupled to a given light shutter in the array. The distal ends of the fibers within the bundle 178 are arranged in the same array configuration as the proximal ends so as to maintain the same array geometry. The aperture of the individual optical fiber determines the field stop of the excitation optics in this embodiment. The light shutters within the array 176 are under the control of the controller 201 via a control line 200, and in operation, the controller sequentially opens light shutters so as to provide an excitation beam sequentially to all fibers in the array.

Light emanating from the distal ends of the fibers in the bundle is imaged onto a sample 185 with objective optics 179. In the embodiment shown in FIG. 11, a beam driving mirror 184 is provided, the function of which is to select, within the sample, the desired area from which an array of volume elements is to be analyzed. The tilt of the directing mirror 184 is controlled by a joy stick 187, which may be operated manually, or be under the control of the controller 201 via control line 196.

Responses from the target array of volume elements within the sample 185 are redirected by the directing mirror 184 to the objective optics 179, and a beam splitter 180 is utilized to separate the excitation beam from the responses. Since the illumination of volume elements within the target array is sequential, at any time, only responses from a given volume element are received by the detector assembly. The detector assembly contains an array of detectors 183, and the respective apertures of each detector element within the array also serve as the field stops of the detection optics. Since both the excitation optics and the field stops of the detection optics are conjugated within the target volume element in the sample, we ensure that detection of responses emanating essentially only from each volume element are recorded for each volume element in the sample.

The detector assembly also contains additional traditional optical elements, such as a spectral filter 181, whose function is to eliminate from the responses undesired parts of the spectrum. For instance, when the excitation beam is a nitrogen laser and the desired responses are fluorescence emissions, the filter blocks any reflections of the excitation beam and prevents their registration as responses. A spectral analyzer 182 is also included to determine the spectral distribution of the responses. The detector array is under the control of the controller 201 via a control line 194 so as to ensure the synchronization of excitation and response detection from each volume element in the target sample.

The detector assembly, or in some embodiments a specific element of the assembly such as an objective lens, may be caused to move in a direction parallel to the optical axis of the assembly with a driving mechanism 186 under the control of controller 201 (through control line 197), so as to adjust the z position, or depth, of the volume elements probed by the array microprobe system, in a manner similar to that described above.

Signals from the detector, representing optical responses, are directed to a signal processing unit 202, which then transfers the data to an analog to digital converter 203 for further data conditioning in a data preparation module 204. The data representing responses (and tagged to assure that the processor recognizes data from various volume elements, which is achieved with a control line 199 from the controller 201) are then treated in a calibrator/scaler 205 to normalize the data. This is achieved by monitoring the output of the light source and renormalizing data for variations in the output of the source via line 220.

The control and data processing unit 171 contains a memory unit 210 in which calibration and scaling constants 208 are stored as well as correlation transform matrices 209, as further described below. Data from the system are converted to diagnostic information by a computer 211 and displayed, either as diagnostic values or as artificial maps on a display station 212. The computer has memory (resident or removable) in which data may be stored and retrieved for future analysis off line.

In general, the invention is intended to operate, at least partially, to record and generally also compile and analyze the responses it collects. In some low cost embodiments of the instant invention, only diagnostic prediction of pathologies is provided. In this case, the system is equipped with a library of correlation transform vectors or matrices for specific diagnostics, and the system only registers the signals $I_{ij}$ (response intensities at a specific wavelength, i, for a specific volume element j) and calculates fuinctions $F(I_{ij})$ required to provide a diagnostic score $C_j$, for an array of volume element j, as is further described below.

The output from detector 183 is fed to a data processor 206 after preprocessing in signal processor 202, analog to digital converter 203 and data preparation module 204. Data processor 206 may process the output from detector 183 or it may store the data in memory unit 210 for processing at a later time. The computer 211 may also provide the ability to compare a first data set obtained from detector 183 with a second data set obtained from memory unit 210, or to perform comparative studies of various volume elements within an array of volume elements measured at any given time, thus providing for spatial correlation of volume elements within a given sample. For example, data processor 206 may calculate correlations between a first data set representative of the material being probed and a second data set in memory unit 210. In accordance with a preferred embodiment of this aspect of the invention, the second data set may be a library of optical response data or a mathematical model abstracted from such a library, as is more fully described below.

Memory unit 210 may be used to store a large body of data about particular materials. For example, memory unit 210 may store data concerning the characteristics of light which has interacted with a particular type of biological tissue, or memory unit 210 may store data concerning the characteristics of light emitted, particularly fluorescence, by particular types of biological tissues in response to excitation by each of a set of wavelengths of light, or may store such spectra indexed by tissue depth, or other complex multidimensional spectra derived from a prior set of observations.

Memory unit 210 may further store information associating particular characteristics of light obtained from a biological tissue sample with a particular diagnosis. For example, the ratio of light reflected at one wavelength to light reflected at a second reference wavelength may be associated with cancerous tissue growth as in certain known observations, or may be associated with a clinically relevant condition such as a thickening of one layer of tissue, a precancerous metabolic change, or a malignancy, based on correlation with the spectral library and previous clinical characterizations. Thus, correlation with annotated or stored digitized spectra may provide a diagnostic judgment, even without the identification of any specific individual spectral features, such as peaks or absorbance bands, that have been required for diagnosis in the past.

While in the embodiments shown herein, for example in FIG. 11, the detector 183 is shown accepting responses from the specimen after being treated trough a spectral analyzer 182, it should be clear that the spectral analyzer may be replaced with either a temporal interferometer (such as a Michelson interferometer) or a spatial interferometer (such as a Sagnac interferometer). The resulting interferogram may then provide the Fourier transform of the optical responses obtained from each volume element probed for subsequent data analysis as described elsewhere in this application.

Similarly, when performing Raman spectroscopy, particularly when selecting for an excitation beam a source in the near infrared, where the intensity of the Raman scattering is greatly reduced, one may impose in the response path, in lieu of an interferometer, a Hadamard encodement mask consisting of a multi-slit array, in order to obtain via Hadamard transform of the data the Raman spectral response of the probed volume elements.

In the prior art, spectral and chemical analysis of complex and heterogeneous matrices with good localization of such analysis was hindered by the inability to limit the response obtained from such matrices from regions with a high degree of homogeneity. A large group of microprobes was thus developed to handle this problem, and indeed, electron microscopes and ion microprobes and various other devices capable of providing analytical information exist, both morphological and to some extent chemical (mostly elemental) on a point by point or even through sections (such as in the ion microprobe) of a specimen. Unfortunately, these methods all require the placement of the sample in vacuum and the eventual destruction of the specimen, and furthermore these methods are not conducive to the analysis of organic materials. In vivo microprobe analysis of biological tissue has requirements that are somewhat different from those of classical microprobes. Particularly, it is not desired to have a resolution greater than the typical dimensions of differentiated tissues, but it is required to have analytical tools that may be operated by personnel without specific training in the analytical arts, such as physicians, process control personnel and other professionals. The use of the present invention allows for microprobing of samples and biological tissues in vivo, and enables the spatial delineation of compositional, morphological and pathological features of such specimens. There are numerous approaches by which the data from such array volume microprobe may be used, and without limiting the scope of the instant invention, we describe herein some of these approaches.

In one embodiment of the present invention, responses from an array of volume elements, which represent the interactions of the material within each of said volume elements with the exciting radiation, or at least contain specific signatures of such interactions, are presented in terms of received light intensities for various wavelengths, or as is known in the art, as a spectrum of the response. A researcher trained in the specific analytical art may then use these spectra to deduce important information about each of the volume elements in the array from his knowledge of the exciting radiation and the modes of interactions of the radiation with his target material. A variety of analytical tools, such as software programs designed to conduct spectral peak fitting, or spectral deconvolution, may be used to further increase the researcher's basic understanding of such interactions and to provide the researcher with information on the chemical, morphological and physiological nature of the target volume elements in the array, since the responses correspond each to a specific volume element in the array probed. This in accordance with basic principles known in the art, except that the data provided to the researcher are derived from a well-defined volume element and thus interferences and response weakening due to parasitic responses and interferences originating outside the target volume elements no longer hinder the researcher's ability to differentiate specific features within a largely heterogeneous sample. Thus, the array volume microprobe of the present invention may be used to perform classical spectroscopical analysis, fluorescence analysis, Raman scattering and other parametric or characterizing analysis which involves the measurement of the responses of each volume element in the array to a localized radiation while limiting the observed responses to essentially each of the volume elements in the array only at any given time.

In another embodiment of the present invention, directed to users that do not possess the technical skills to derive meaningful conclusions from raw responses observed, the system is equipped with a library of correlation transforms dedicated to the user's special needs, so that the system is essentially pre-calibrated for specific analytical tasks. The method of calibrating the array volume microprobe is further detailed herein. In many of these diagnostic situations, a physician who is not a trained spectroscopist views the suspected tissues, and when discoloration or other morphological abnormalities are present, samples from such areas are excised and sent to a pathological laboratory for microscopic examination of the tissues to determine the presence or lack thereof, as well as the stage, of possible cancer. It would be extremely useful if, during the visual examination, a diagnostic scoring to determine the nature of the suspected pathology of the suspicious target tissue was available, so that immediate action may be taken, if necessary, and to avoid unnecessary excision of tissue for biopsies. When calibrated as described below, the array volume microprobe of the instant invention will enable the automated diagnostics of such viewed tissues by a physician, provide an artificial image of the pathology and its extent, without the need to examine such tissues under the microscope by another professional pathologist.

Figure 12:
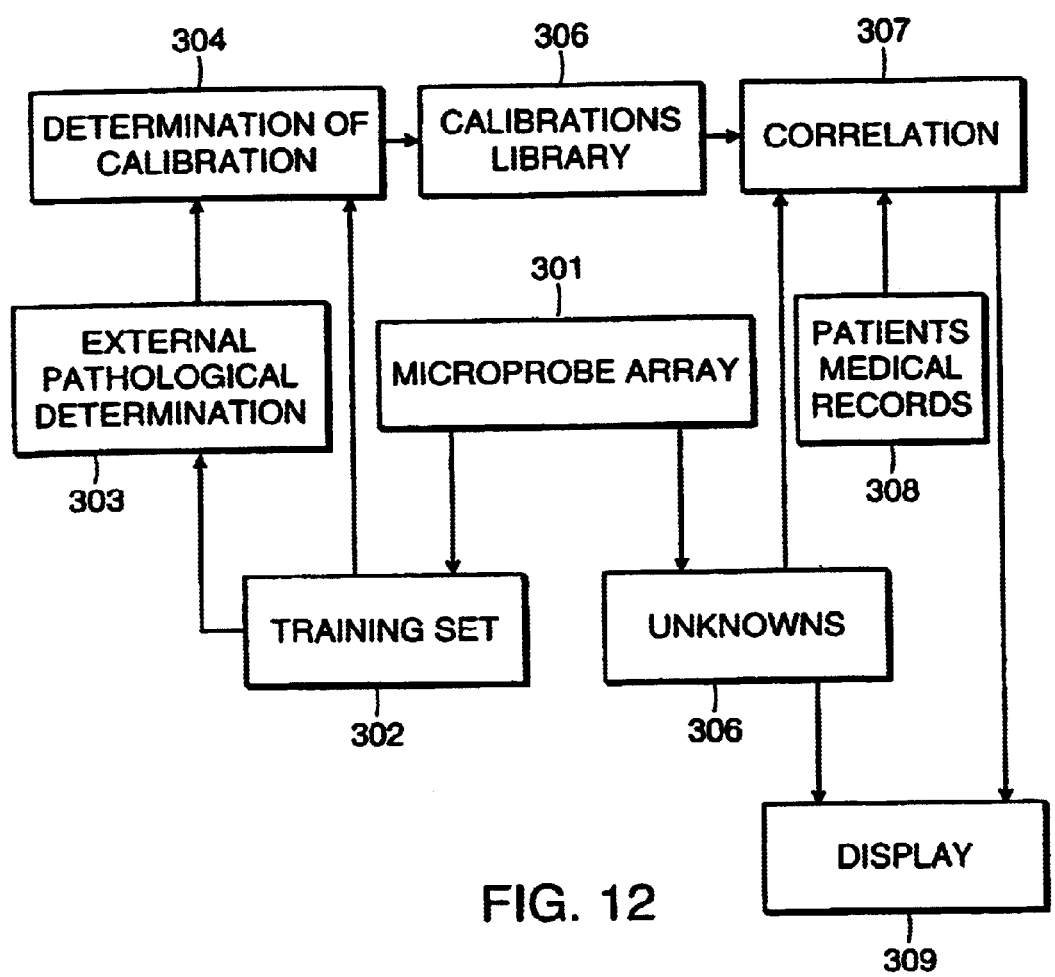
FIG. 12 is a block diagram that illustrates methods of using volume probe arrays of the invention, particularly in the diagnostic of various pathologies.

FIG. 12 is a diagram 300 showing the various steps undertaken in the calibration and then the use of the array volume microprobe. In order to calibrate an array volume microprobe 301 for a specific pathology, a training set 302 of specimens for the specific pathology is first selected. The term training set will be used herein to denote a group of tissue specimens on which very exacting cytological and pathological determination of the state of each specimen was conducted in a pathological laboratory, denoted by the step 303. Furthermore, prior to excision for such biopsies, each specimen in the training set was subjected, in vivo, to an exacting study with the microprobe array 301 of the present invention. For the purpose of this description, let us assume that the target volume elements in the training set (those tissues that are later subjected to a pathological laboratory determination of their respective pathological states) are excited with both a laser UV source and a broad band white light source. To assure good spatial correlation between the excised tissues and the volume elements examined, during calibration, the array is used with only a single shutter open, or a special single channel non imaging volume microprobe may be used. Let the intensities of the responses to the UV and white light excitations of the targeted volume element within the specimen j be $J_{uj}$ and $I_{ij}$ respectively, where u and i are central wavelengths within spectral bands of the spectral responses to the UV and to the white light excitations, respectively. These data are stored in memory (for instance memory unit 210 in FIG. 11) for future analysis and determination of the master calibration at step 304. The volume elements in the training set are excised after recording the responses obtained with the non imaging volume microprobe, and pathological determinations of the state of each specimen are recorded in the form of scores $C_j$, where j is the identity of the specimen and $C_j$ is a number selected according to the specimen state on a monotonic scoring scale, for instance 0 to 10, where zero denotes normal tissues and 10 fully entrenched and deep cancerous tissues. Since this training set will calibrate non imaging volume microprobes for future determinations of the presence or lack thereof of such pathologies, it is important that great care is taken at arriving at an objective determination of the pathological state of the training set. In such cases, the same samples are examined microscopically by a number of independent pathologists in a blind experiment, and only those specimens for which a minimum agreement between the various pathological results exists, are included in the training set.

Once the scores $C_j$ of the specimen in the training set have been carefully determined, and the medical records of the patients associated with samples (volume element) in the training set are recorded (more than one volume element per patient may be included in the training set, however, it is best to include a variety of patients in a training set for a given pathology), the values of $I_{ij}$ and $J_{uj}$ previously stored in memory unit 210 are used to set up a set of n correlation equations (n would be the number of volume elements in the training set):

$$Ea_iF(I_{ij})+Eb_uF(J_{uj})+Ec_sG(M_{sj})=C_j \qquad (1)$$

The bandwidths around the wavelengths i and u of the responses to white light and UV light, respectively, are usually between 5 and 50 nm, depending on the spectral resolution achievable or desirable in the system's detection monochromator or spectrograph (element 182 in FIG. 11).

The selection of the functions F depends to some extent on the nature of responses received. When almost featureless spectral responses (namely a spectral response which is relatively smooth and changes slowly with the wavelength) are received, then one often selects the intensities, or normalized intensities, of the responses namely, $F(I_{ij})=I_{ij}$ or $F(I_{ij})=I_{ij}/K$, respectively, where K is either the maximum response in the received spectrum or the response at a predetermined wavelength (in biological tissues, often a response associated with the presence of water or hemoglobin). When the spectrum expected contains a number of sharper features, one often may use $F(I_{ij})=(dI_{ij}/d8)I_{ij}$, where 8 is the wavelength. Of course, it is best to use the same function F for the responses to both UV excitation $J_{uj}$ and white light excitation $I_{ij}$.

The functions $G(M_{sj})$ are included to allow for the impact on the observed responses of the patient's specific "medical history", and usually includes parameter such as sex, age, race, and presence or lack thereof of systemic pathologies such as hypertension, diabetes etc. In many situations, part or all the coefficient $c_s$ are nil, and these factors have no impact on the calibration, but in special cases, these factors play a role and are included here for completeness.

A computer is now used at step 304 to perform a regression analysis to minimize the number of wavelengths i and u (and s which are "artificial wavelengths" representing medical history) used to obtain a valid correlation and to solve the set of minimized equations (1) for the correlation constants $a_i$, $b_u$ (and $c_s$). This regression analysis is performed using the n equations obtained experimentally, using in essence the correlation constants as unknowns, for which a solution having the best correlation is sought. The minimization is carried out to extract those wavelengths at which the responses contain independent relevant information that correlates the responses $I_{ij}$ and $J_{uj}$ to the scores $C_j$. It should be appreciated that during the calibration process, a greater amount of data is collected than absolutely necessary, and much of these data are interrelated. To obtain a sufficiently good correlation, only responses that are independent from each other are necessary, and thus the process of minimization of spectral responses in equations (1) is carried out. This minimization will also allow, during actual diagnostic use of the non imaging volume microprobe, the taking of a minimal set of responses and thus will accelerate the procedure.

The methods used for obtaining the minimal set of wavelengths and the associated correlation coefficients $a_i$ and $b_u$ are well known in the prior art and include multivariant linear regression analysis and univariant linear regression analysis. Other statistical tools, such as neural networks analysis, are also available and may be used for this purpose.

In general, we may term the values $I_{ij}$ and $J_{uj}$ the responses of the volume element to white light and UV excitation, respectively. As we have mentioned, other responses may be used to characterize a volume element in a sample. We therefore term all responses which are responses from volume elements that correlates with certain pathologies as responses $R_{ij}$. As mentioned above, we found that it is sometimes advantageous to include as part of the responses $R_{ij}$ other information about a volume element (or the volume element's host) which was not determined with the help of the non imaging volume microprobe but still contributes to improvement in the correlation between the observed responses and the pathologies diagnosed. Such information may include general classification of the subject in which the volume element resides, such as, but not limited to sex, age, race, other systemic pathologies and weight. Such information, when its inclusion in the regression improves the confidence level of the regression, may be included as additional artificial responses $R_{ij}$ (in lieu of the functions $G(M_{sj})$). The index i therefore represents the type of response obtained, whether it is obtained with the non imaging microprobe (one or more types of responses as well as the spectral band from which the response is registered) or by other means.

The set of equations (1) from which the correlation coefficients are derived may thus be simplified to be:

$$Ea_i F(R_{ij})=C_j \qquad (2)$$

For simplicity, the ordered values $a_i$ may be termed the correlation vector (a) for pathology C, and the ordered responses $R_{ij}$ may be termed the response vector $(R_j)$ for volume element j in the training set. The functional response vector $(F(R_j))$ is similarly defined as the ordered functions of the elements of the responses in the response vectors $(R_j)$. Similarly, the ordered scores $C_j$ may be termed the pathology score vector (C) for the training set. The process of calibrating the array microprobe for a given pathology C consists therefore of obtaining all the response vectors $(R_j)$ and their corresponding pathology score vector (C) and from these data, after generating the functional response vector $(F(R_j))$, obtaining a minimal correlation vector (a), which is the calibration vector of the non imaging volume microprobe. As may be seen, the calibration is identical to the calibration designed for the non imaging volume microprobe of U.S. Pat. No. 5,713,364. The calibration for a number of different pathologies may be stored in a calibration library 305 for future use on unknown specimens. Each microprobe array includes a correlation engine 307 which may take calibration vectors from the calibration library 305 and response vectors obtained from the microprobe array and other sources such as medical records 308 and reconstruct for the response vector a value C of the observed pathology. Since in the various embodiments of the invention the different optical channels representing excitation and responses from given volume elements are equivalent, a single calibration (for a given pathology) suffices.

When we now want to determine the nature and distribution of a pathology in a target specimen, which is outside the training set, or an unknown specimen 306, and for simplicity let us term each such volume element in the array k(x,y,z), delineating its x, y and z coordinates. The response vectors $(R_k(x,y,z))$ are registered by the instrument on the volume element k(x,y,z), and to the extent that some of the responses $R_{ik}$ are artificial responses (such as sex or race as mentioned above), these are entered into the correlation engine part of the microprobe array and the score for the pathology for volume element k(x,y,z), $C_k(x,y,z)$, is predicted by obtaining the product of the correlation vector (a) found earlier with the functional response vector $(F(R_k(x,y,z)))$, namely: $C_k(x,y,z)=Ea_i F(R_{ik}(x,y,z))$. Thus the use of the calibrated microprobe array on an array of volume elements k(x,y,z), whose pathological state $C_k(x,y,z)$ is unknown, allows for the immediate and automatic diagnosis of the pathology in volume element k(x,y,z). This procedure is repeated for all volume elements in the array, and the set of values $C_k(x,y,z)$ for all volume elements in the array may now be presented on a display 309, either as numerical values or as artificial images of the array examined. Normal methods of three-dimensional image handling and manipulation may thus provide the physician with an insight as to the nature, extent, severity and penetration depth of suspected pathologies. This reduces the number of unnecessary biopsies required and provides the physician with immediate information on which he may act during the examination.

It should be appreciated that the functions $F(R_{ik}(x,y,z))$ may be derived from the Fourier Transforms obtained from the responses, either with a temporal interferometer such as a Michelson interferometer or with a spatial interferometer such as a Sagnac interferometer. It is even possible to use the interferograms themselves in lieu of the Fourier transform generated from them. Similarly, when probing for molecular structural information on the probed elements, one uses for the functions $F(R_{ik}(x,y,z)$ the values at various wavelengths obtained from the Hadamard transform of the Raman spectral response.

It should be appreciated by persons trained in the art that microprobe arrays of the invention may be calibrated to diagnose a plurality of pathologies $P_m$, where m denotes a specific pathology. When used in this fashion, the task of calibrating the instrument for this plurality of pathologies consists as before of obtaining for a training set j, responses $R_{ij}$ and pathological scores $P_{mj}$, where i is the bandwidth of the response or the type of artificial response, j is the volume element or the specimen in the training set and $P_{mj}$ is the score for pathology m on specimen j. During calibration, we obtain a number of correlation vectors $(a_m)$, each for the specific pathology m. In operation of the calibrated non imaging volume microprobe, the correlation vector (a) mentioned above is now replaced with a correlation matrix $\{a\}$ whose elements are $a_{im}$, the functional response vector $(F(R_k))$ for an uncharacterized specimen, k, is replaced with the matrix $\{F(R_k)\}$ whose elements are $F(R_{imk})$ and the diagnostic results are given as a vector $(P)_k$ whose elements are $P_{mk}$ by obtaining the product of the correlation matrix $\{a\}$ with the functional response matrix $\{F(R_k)\}$.

It should also be appreciated that in the practical embodiment of this method of analysis, the correlation created will use the same responses (if not all of them at least some of them) for different pathologies. Thus only a response vector $(R_k)$ (having elements $R_{ik}$) is required, which includes the minimal set of responses from volume element k to obtain diagnostic scores $P_{mk}$. The matrix $\{a\}$ may also be termed the correlation transform matrix, since it transforms one set of measurable (or observable) values, to another set of numbers or values, which are the desired pathological scores. This is achieved by multiplying the correlation transform matrix, $\{a\}$, with the vector $(F(R_k))$, the functional response vector, to obtain a transformation of the response vector $(R_k)$ to a diagnostic score vector $(P)_k$.

The correlation transform method exploited herein, of predicting diagnostic or analytic information on an unknown specimen by correlating optical responses of a training set to independent determination of the diagnostic or analytic data on the training set has been shown by Rosenthal to work well on artificially homogenized samples that are large enough to provide a set of responses possessing a large signal-to-noise ratio. It is surprising that the expanded method of the instant invention yields good correlation on very minuscule volume elements in vivo. In classical spectroscopy, for instance, as practiced by Alfano, spectra or optical responses of diseased tissues are compared to similar spectra or responses of healthy tissues to attempt a diagnostic reading on the target tissue. This method fails to work because of the large variations encountered between subjects and the nature of the tissue examined. When using our correlation transform approach, we purposefilly avoid using comparison of spectral responses in a target tissue to the responses of any existing (healthy or pathological) tissue, since no one specific tissue may represent all the variations encountered between subjects. Such subject-to-subject variations cause spectral distortions that invariably weaken the ability of the prior art to obtain robust diagnostic determination of pathologies. Furthermore, our inclusion of non optical responses together with optical responses, as part of the correlation transform algorithm, in essence builds a completely artificial model (based on the training set) of the pathology, which by itself is never reproduced in any one subject or tissue. Finally, this novel approach, coupled with the spatial filtering of the optical responses to a small, volume element, thus avoiding response integration over heterogeneous tissues, makes it possible to obtain valuable artificial imaas of pathologies heretofore not feasible.

For simplicity of the descriptions provided herein, we assume that a goal of the method is to calibrate an array volume microprobe for the diagnosis of the presence or lack thereof of tissues that are affected by certain pathologies including cancer and that are accessible to optical visualization, either on the external skin, or in a body orifice such as the mouth or the vagina, or in other cavities that are accessible via endoscopes or laparoscopes, such as the various segments of the gastrointestinal tract or various organs in the body cavities, such as the thoracic cage and the peritoneal cavity. In situations where body cavities are being accessed by endoscopes or laparoscopes, it is important to provide a system and a method that is adapted for these medical uses. It is furthermore important to provide systems and methods adapted for those other medical uses where the hardware probe is being used for in vivo diagnosis of biological tissues. Since the hardware probe is able to be placed into contact with.biological tissues, contamination of the optical hardware probe must be avoided. A disposable probe or a disposable covering for the optical hardware probe may be particularly advantageous in these circumstances.

In one embodiment, an apparatus according to the present invention may be used to determine a characteristic of a sample of a biological material in an in vivo situation. In the in vivo situation, the sample of biological material may exist in continuity with an in vivo body tissue of a patient. In this embodiment, a barrier or a disposable sheath may be provided to prevent the probe from contacting the biological material and from contacting the in vivo body tissue of the patient in juxtaposition to which or in proximity to which the sample of biological material is found. Furthermore, in an embodiment of the apparatus disclosed herein, a barrier or disposable sheath may prevent the probe from contacting those tissues that surround the in vivo body tissue wherein the sample of biological material being examined may be found. In one embodiment, a barrier or disposable sheath may entirely cover the probe; in another embodiment, a barrier or disposable sheath may cover those parts of the probe adapted for contact with a body tissue of a patient. The term sheath as used herein is understood to encompass any device that fits over part or all of the optical hardware probe and that is thereby interposed between the probe and sample being studied or between the probe and an in vivo body tissue.

A disposable device may be designed for a particular anatomic application. Procedures involving the gastrointestinal tract, the urinary tract, the peritoneal cavity, the thorax, and the female reproductive tract are examples of where a disposable device may be used. It will be especially advantageous to provide the hardware of the present invention with a disposable cover or sheath that may be adapted for use on a single patient. Furthermore, in one embodiment, the probe is constructed so that a sheath must be in place for the probe to be operable. Certain mechanisms are described in more detail below for ensuring single use of a sheath or to ensure that the probe cannot be operated without a sheath properly positioned to cover it. Other mechanisms will be readily apparent to those of ordinary skill in these arts.

Figure 17:
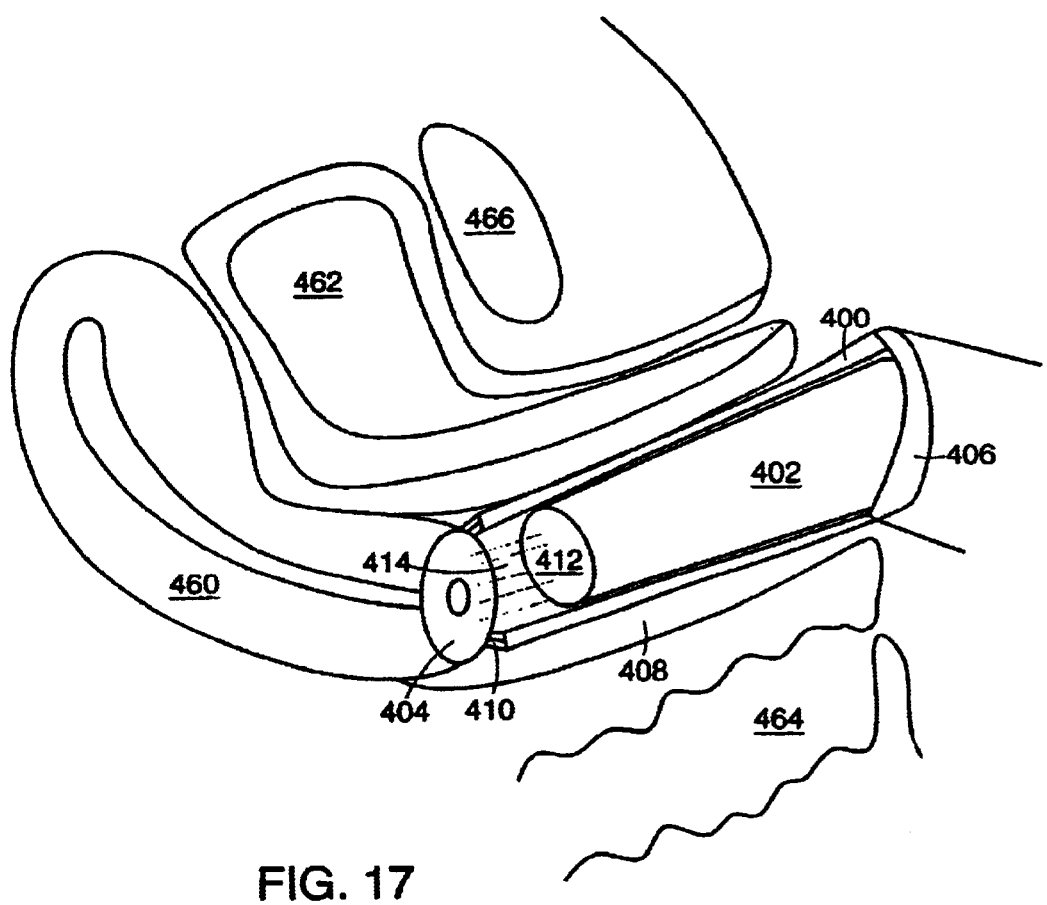
FIG. 17 is an anatomic cross-sectional view showing an embodiment of the invention positioned within a body cavity within the female perineum.

FIG. 17 shows an embodiment of the apparatus of the present invention adapted for use in examining a tissue of the cervix uteri. An embodiment of the present invention may be used to examine either the external cervix or the internal cervical os. Embodiments of the present invention may be adapted for colposcopic use. FIG. 17 shows an anatomic partial cross-sectional view of the female perineum depicting an embodiment of a disposable sheath 400, here shown in cross-section, positioned within the vagina 408. Adjacent structures including the bladder 462, the uterus 460, the rectum 464 and the symphysis pubis 466 are shown here to facilitate orientation. This figure shows an embodiment in which a disposable sheath 400 may be provided for an optical hardware probe 402 to illuminate the cervix 404. Configurations for the sheath 400 may be adapted to the anatomy of the cervix 404 and vagina 408. The white light illumination 410 of the cervix 404 for video illumination may be provided circumferentially. The distance from the distal end 412 of the probe 402 to the cervix 404 may be about 100 mm. The probing beam 414 of the optical hardware probe 402 may be transmitted through the disposable protective sheath 400 to strike the cervix 404.

A simple cylindrical structure may provide an interface between the distal end of the light transmitting fibers and the disposable sheath 400 so that light is transmitted to illuminate the cervix 404. In one embodiment, an end plate (not shown) applied to the distal end 412 of the hardware probe 402 may be fabricated of a material designed to minimize the fluorescence emitted from the plate when the UV excitation beam is applied. An example of a substance for fabricating the plate is polymethyl methacrylate (PMMA), although other optical plastics that will nnimize fluorescence may be envisioned by practitioners of ordinary skill in these arts. The interface between the ring on the optical hardware probe 402 bearing the optical fiber ends and the disposable sheath 400 may be made from a silastic transparent material in the form of a segment of a toroid.

In an alternative embodiment of a disposable sheath 400, a light source ring (not shown) is positioned distally just at the distal end 412 of the hardware probe 402. This embodiment may include a transparent silastic ring with a 20 degree slanted toroidal lens. The toroidal structure may have a retracted snap-on mechanism that fastens the lens to the steel ring of the probe. The toroidal silastic element may be part of a highly flexible thin plastic sleeve that has a frontal membrane as its optical window. The thin plastic sleeve may extend proximally to wrap the hardware probe. Flexible plastic materials may include thin polyethylene films shaped conically to facilitate initial wrapping and tensioning of the frontal film. Other appropriate plastics may be envisioned by those skilled in these arts.

A disposable sheath 400 may be attached or fastened to the hardware optical probe 402. A variety of fastening mechanisms 406 may be envisioned by those skilled in these arts. A fastening mechanism 406 is understood to comprise those mechanisms and systems that may affix the disposable sheath 400 to the hardware optical probe 402. As one example, a simple band latching mechanism may be employed. Alternatively, a latching mechanism may be employed that uses a unidirectional latch. As another example, a plurality of pins or posts may be placed on the hardware probe 402. These pins or posts are positioned to align the light transmission fibers in the hardware probe 402 with the corresponding regions in the disposable sheath 400. A fork-like latch on the proximal part of the disposable sheath 400 may articulate with the posts so that once a post is latched into place, it may only be released by breaking the latch. The disposable sheath 400, according to this embodiment, cannot be removed from the optical probe 402 and subsequently replaced on the probe 402 to be used for another patient. Other embodiments may be envisioned wherein the disposable probe is adapted for single patient use only. Fastening mechanisms may be envisioned by those skilled in the art that will confine the disposable probe to use on a single occasion. A number of other affixation mechanisms may be devised by those of ordinary skill in these arts whereby the sheath or barrier may be detachably attached to the probe and whereby detaching the sheath or barrier prevents a subsequent use of these devices, thereby ensuring that a sheath or barrier be used only once. Certain of these affixation mechanisms are described below, but these descriptions are not intended to limit the scope of the invention as claimed herein.

In certain embodiments, the disposable sheath 400 provides a frontal window of adequate optical quality so as not to alter the optical signals passing to and from the hardware optical probe 402. These features furthermore adapt the device for use in a plurality of medical situations. These features render the device more useful for medical personnel in a variety of circumstances. The embodiments disclosed herein are not intended to be limiting, however. Other embodiments may be envisioned by those of ordinary skill in the relevant arts.

Figure 18:
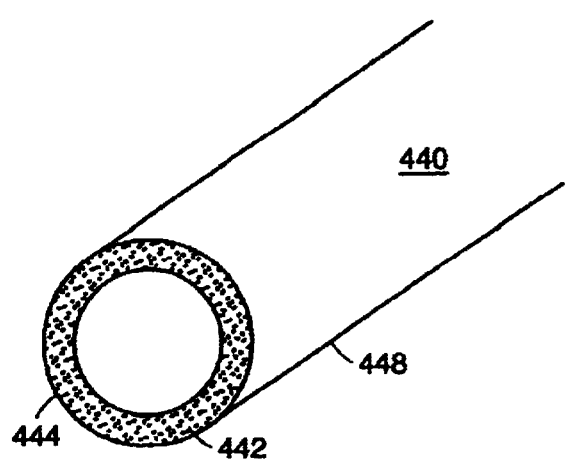
FIG. 18 shows an embodiment of a disposable sheath illustrating optical fibers therein.

FIG. 18 depicts the distal end 448 of one embodiment of a disposable sheath 440 according to the present invention. In the depicted embodiment, a bundle of optical fibers 442 may be arranged in a ring 444 within a disposable sheath 440. The distal end 448 of the disposable sheath 440 may be designed according to the selection of the topology of fiber 442 arrangement. As an example, a ring 444 may be constructed in the sheath 440 with an inner diameter of 25 mm and an outer diameter of 28 mm. This configuration may permit a number of optical fibers 442 to be placed within the ring 444, each fiber 442 having a diameter of 1 mm. In one embodiment, 78 optical fibers 442 may be placed within the ring 444 arranged according to this configuration. Alternatively, spaces may be left between the optical fibers 442 in an arrangement, or optical fibers 442 may be bundled. Furthermore, the thickness of the ring 444 of optical fibers 442 may be varied to accommodate more or fewer fibers 442. In one embodiment, the distal end 448 of the sheath 440 may be modular and alignable with the optics of the probe. Other arrangements of the optical fibers 442 in the sheath 440 will be apparent to practitioners of ordinary skill in the art. For example, a plurality of concentric rings may be constructed to contain certain of the optical fibers 442 in each ring 444.

It is understood that the disposable sheath depicted in these figures is shown for illustrative purposes only. A plurality of sheath configurations will be apparent to practitioners in the art whereby the sheath configuration will be suitable to the medical use envisioned for the probe. Moreover, sheath configurations may be designed by artisans of ordinary skill that will be adapted to the optical specifications of the hardware probes disclosed herein. These sheaths, in their various embodiments, will combine advantageously with the optical probe systems and methods of the present invention to permit application in a variety of clinical situations, as will be readily understood by practitioners in these arts.

In one embodiment, a protective sheath of the instant invention consists of two major elements, a frontal optical window, made for instance from cast or molded polymethylmetacrylate (PMMA), and a generally cylindrical sleeve extending from the frontal optical window to cover the optical probe, made of a thin flexible plastic such as polyethylene, the two elements are fastened at the proximal rim of the frontal optical window. The sleeve component of a protective sheath may be of any shape appropriate for the anatomic area, or it may be shaped to fit a particular probe. The sleeve may be tightly applied or loosely applied to the underlying probe. The sleeve may be provided with gathers or folds that arrange for a particular ordering of the sleeve around the probe. A sleeve may be made in part from of a shrink-fitting material so as to conform more closely to the configuration of the probe. The shrinkage may be achieved either externally or by passing a small current in an embedded heating element prior to using the probe. A sleeve may be made of a single piece of material, or may be made of a plurality of components. A variety of sleeve arrangements will be readily envisioned by ordinary skilled artisans in this field.

The frontal optical window may include a hollow cylindrical section mating with the optical distal end of the probe in a unique manner so that only one relative orientation between the probe and sheath is possible. Other shapes for the frontal optical window may be envisioned, based on the configuration of the targeted anatomic area or based on the shape of the underlying probe. An orientation mechanism on the sheath or on the probe may facilitate the proper positioning of the sheath on the probe, so that such positioning is easy and accurate. This orientation mechanism may further permit the reading of a marker on the sheath bearing identifying or other data by an appropriate detector, sensor or reader on the probe.

The selection of the optical polymer used in the rigid frontal optical window may be related to the sort of diagnostic evaluation being performed. It is understood that certain materials have optical characteristics adapted for particular situations. For instance, in the colposcopic examination using an embodiment of the probe according to the present invention, excitation of target tissues with a UV beam is carried out and the fluorescence responses from the tissues are collected to determine potential pathologies. In this situation, the optical window of the sheath may comprise PMMA since this material has no significant fluorescent response to the excitation beam. For the purposes of this specification, a fluorescence response is termed significant when such a response interferes with the accuracy of interpreting those fluorescence responses collected from and emitted by the tissues upon being stimulated with the exciting beam.

Under other circumstances, obtaining an image, for example by way of an embedded CCD in the optical probe, may not be as important as obtaining a very high signal to noise ratio from fluorescence response. Under these circumstances, the end piece transmitting the UV excitation beam may be made of a very thin teflon, or may comprise other fluoroplastics such as THV-200P (a TFE/HPF/VDF terfluoropolymer from the 3M corporation). These plastics do not demonstrate a significant fluorescence response when irradiated with UV.

The optical window may be combined with other optical elements, such as an optical lens, an optical filter, or an optical polarizer. In certain embodiments, the additional optical elements may be made of materials capable of transmitting electromagnetic radiation without generating a significant fluorescent response.

In some embodiments of the invention, a segment of the sheath may be provided with a marker that indicates an unused state of the barrier, and the probe may be equipped with a sensor or a reader that may detect the marker. In certain embodiments, the sensor or reader may generate a signal capable of activating the probe. Under these circumstances, the probe may only be activated in the presence of a sheath that has not been previously used. In an alternate embodiment, a segment of the sheath may be provided with a marker that indicates that the sheath has been previously used. In this embodiment, the probe is provided with a sensor or reader that may detect the marker. In certain embodiments, the sensor or reader may generate a signal capable of activating the probe. Other arrangements will be apparent to practitioners in these arts whereby the needs of the medical community to protect the probe assembly from contamination or cross-contamination may be met. A system can be arranged to prevent the use of a probe and a sheath for more than one diagnostic test cycle. A system can be arranged to prevent the use of the probe and sheath on more than a single patient, while permitting multiple diagnostic test cycles to be executed upon the one patient being examined. Arrangements to confine the use of the probe and sheath may include mechanical, electronic, computer hardware or computer software systems or combinations thereof, which will can be readily devised by ordinary skilled artisans without undue experimentation.

A plurality of arrangements may be envisioned whereby the sensor may detect the marker. In one embodiment, the marker may be placed on an area of the optical window. However, the marker may be located on any convenient part of the sheath, with the sensor on the probe located to permit reading it. In one embodiment, the marker may comprise a serial number of the specific sheath, either in the form of an actual alpha numeric marking, or in bar code form. This serial number may be "read" by a special element in the optical probe and stored in the probe's electronic system. The serial number may be correlated with other data identifying the patient being examined. Each time the probe is used to examine a patient, data is entered to identify the particular patient. In this embodiment, the serial number of a particular sheath is associated with a specific patient. Upon detecting the serial number located on the sheath, the probe may query a database to determine if the detected serial number is already associated with a particular patient, an association that indicates a previous use of the sheath. If previous use of a sheath is discerned, the probe may be rendered inoperable. If use of the sheath on another patient is discerned, the probe may be rendered inoperable. Alternatively, the probe may be rendered operable if no previous use of the sheath is discerned, or if no previous use of the sheath on another patient is discerned. The data on the marker may be compared to any data within a database to determine prior use of the sheath or an unused state of the sheath. The reader on the probe may alter the marker to indicate that the sheath bearing it has been used, or may add data to the marker indicating that the sheath has been used. In one embodiment, the sensor may alter or deface the data on the marker after reading it so it cannot be read again by a probe sensor. A variety of other permutations will be apparent to practitioners in these arts wherein a sensor on the probe may interact with a marker on the sheath to determine or to indicate the used or unused state of the sheath, and furthermore to affect the activation of the probe depending upon the used or unused state of the sheath. These features, providing assurance that the same sheath is not used on different patients, thus avoid the potential problems of cross contamination.

Systems and methods of the present invention may include the detection of various conditions of the sheath. The condition of the sheath may be its used or unused state. The condition of the sheath may be its appropriateness for a particular type of diagnostic test. For example, a different type of sheath may be useful for screening evaluations of the cervix than would be useful for more detailed diagnostic evaluations. The presence of a particular type of sheath could enable the probe system to perform a specific set of diagnostic tests. The condition of the sheath may be its physical integrity, detected through a system incorporated in the sheath itself. The sheath may permit a self-testing for physical integrity, the result of which produces a signal that regulates the activation of the probe. Self-testing may include mechanical, hydraulic, pneumatic, electronic or any other type of test produced by the sheath itself or administered to the sheath by a separate system. The condition of the sheath may be its proper positioning on the probe or in the desired anatomic region. The positioning of the sheath relative to the target tissue may be validated by an orienting system, for example, that produces a signal that must be received as a precondition for activation of the probe for diagnostic examination. Other conditions of the sheath may be determined by an appropriate sensor, with the generation of an appropriate signal to the probe. Furthermore, the systems of the present invention may permit the transmission of a number of signals relating to the condition of the sheath, each one of said signals having an effect on the regulation of the activation of the probe.

The systems described herein to prevent the operation of the probe without the sheath in place represent embodiments of an interlock system. In one embodiment, the sheath and the probe may bear components of an interlock system whereby the proper positioning of the sheath on the probe is needed for the probe to be used. An interlock system may incorporate a marker bearing data pertaining to the particular sheath and a reader incorporated in the probe assembly so that the reader may read the data pertaining to the particular sheath and convey a signal to the probe rendering it operational or inoperative based upon the data the marker bears. An interlock system according to these systems and methods may comprise hardware or software circuits preventing the probe from being used unless a previously unused sheath is properly positioned upon said probe. An electrical or electronic circuit may be included in the optical probe system whereby the presence of a properly positioned probe is needed in order to complete the circuit and permit activation of the probe assembly. In one embodiment, the proper positioning of the sheath upon the probe may release an electrically conductive fluid that would enable the activation of the probe by, for example, permitting an activation circuit to be completed or by allowing a signal to be transmitted to the probe to activate it or to deactivate a system preventing use of the probe. Proper positioning of the sheath upon the probe may release an electrically insulating fluid that may block an inactivation system on the probe, thereby activating it. In another embodiment, the proper positioning of the sheath upon the probe includes the positioning of a latch mechanism whereby a fastening component on the sheath interdigitates with a fastening component on the probe, thereby completing a circuit or transmitting an electrical signal that activates the probe. A plurality of other interlock devices may be envisioned that are adaptable to the positioning of a sheath on a probe and further adaptable to any positioning of two components of a device relative to each other.

In one embodiment of the systems and methods of the present invention, at least a portion of the sleeve is made to mate with a feature of the optical probe. A feature may be disposed upon the external aspect of the probe, to correspond with an element of the sleeve. As an example, a recessed groove may be positioned on the external aspect of the probe, into which a longitudinal bar of plastic material on the inner surface of the sleeve is pressed fit.

In some embodiments of the invention, we also provide for mechanical prevention of reuse of the disposable sheath. This is accomplished, for instance by providing physical breakage of at least a critical part of the sheath upon its removal from the probe. The element on the sheath that mates with its counterpart on the probe may be constructed so it will break when detachment of the sheath takes place, preventing a subsequent attachment of the sheath to a probe. In certain embodiments, the sleeve material may be weakened around the mating structure on the sleeve, so that it tears away at the weakened area when it is detached from the probe. In yet another embodiment, an index-matching liquid that improves the interface between the probe's distal end and the sheath's end optical element, is provided, but may be used only once, thus creating another safeguard against multiple uses of the same sheath on a plurality of subjects.

While the embodiments illustrated herein pertain to a probe suitable for use in a biological environment, the interlock mechanisms disclosed in the present specification may be applied to any system where the mating of a first component with a second component must be properly performed in order for the first component to be activated. Furthermore, the systems and methods disclosed herein may be applied to any disposable sheath that is applied to a probe to provide a barrier between the probe and a feature of the environment in proximity to the probe. For example, a disposable sheath according to these systems and methods may prevent contact between the probe and a body fluid in a biological environment. A disposable sheath according to these systems and methods may prevent contact between the probe and any substance making up the probe's environment. For example, a probe may be used to diagnose a tissue immersed in a fixation solution which may have a damaging effect on the probe if it were to contact the probe. A disposable sheath may be used to prevent contact between the probe and the inimical environment. A probe used in industrial settings may be placed in various environments where contact between the probe and a feature of the environment might be damaging to the probe or might interfere with the probe's accuracy. A disposable sheath as disclosed herein may be used to protect the probe from such contact. Furthermore, such a disposable sheath may also comprise a single-use mechanism whereby the single use of the disposable sheath is assured. A single-use mechanism may include an affixation mechanism whereby the barrier may be attached to the probe and whereby, upon detachment, the barrier is prevented from being re-used. The single-use mechanism may include an interlock system that recognizes the proper position of the barrier on the probe and that prevents the probe from being used without the barrier in the proper position. Other embodiments of the single-use mechanism may be envisioned by practitioners of ordinary skill in the relevant arts.

Figures 19A, 19B:
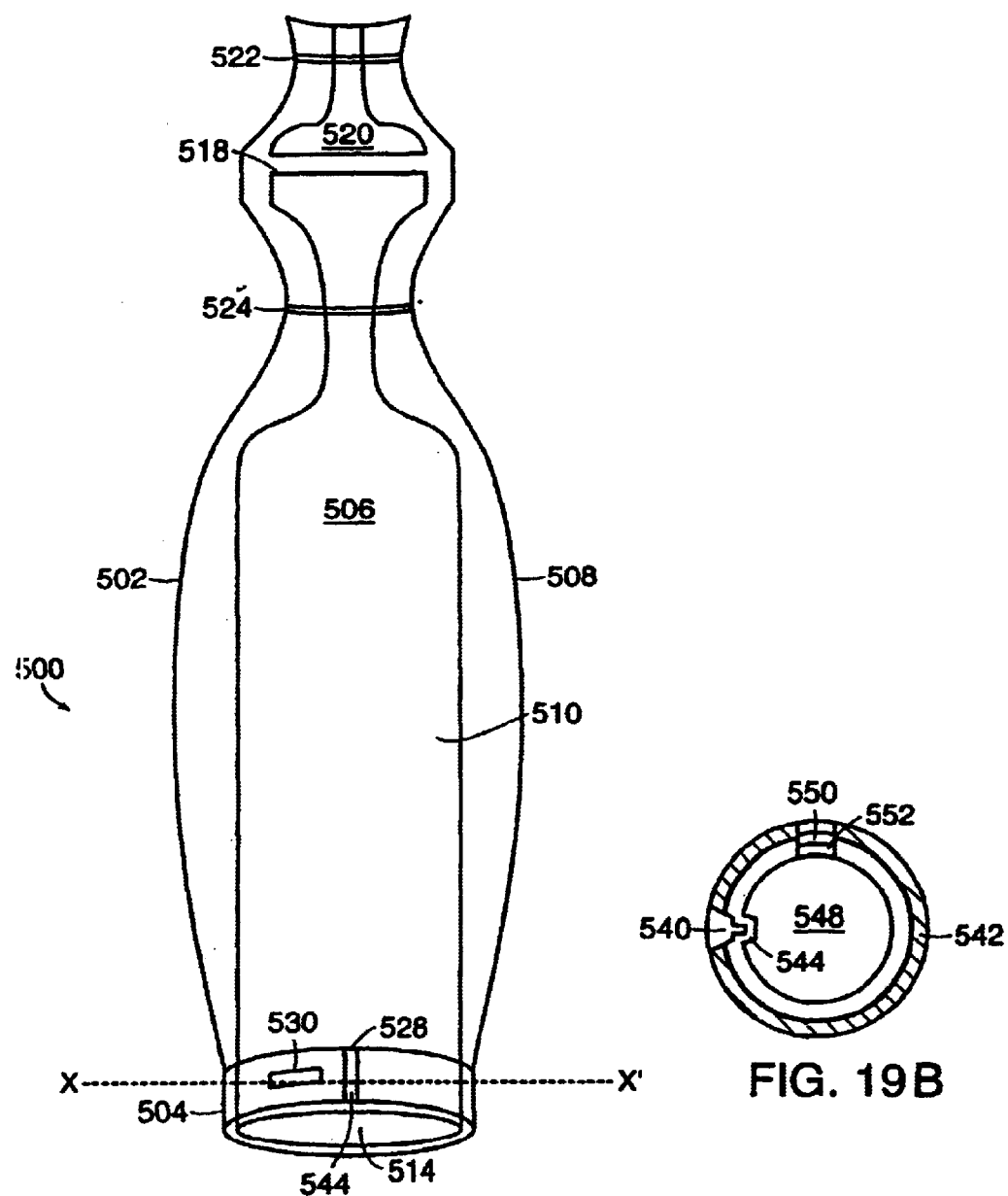
FIG. 19A and B show an embodiment of an optical probe bearing a protective sheath.

FIG. 19A shows a perspective view and FIG. 19B shows a cross-sectional view of an embodiment of an optical probe covered with a biological isolation barrier or disposable sheath. FIG. 19A shows generally an embodiment of an optical probe system 500 comprising an optical probe 506 covered with a disposable sheath 502. The sheath 502 is shown here as including two elements, a rigid distal optical element 504 and a flexible thin sleeve 508 that may be gathered or wrapped at different locations on the probe 506.

The term distal, as applied herein to a medical device, is understood to refer to that aspect of a device closest to the target tissue being examined; the distal aspect of the device is generally also furthest away from the operator. That aspect of the medical device furthest from the target tissue is termed proximal; the proximal portion of the device is generally also that aspect closest to the operator. The probe 506 may consist of a cylindrical body 510 containing certain optical elements, for example a CCD (not shown) for imaging, or optical wave guides (not shown) to facilitate transmission of excitation beams to target tissues and the transmission back of responses from a target tissue to the main console. Other shapes for the probe and its body may be readily envisioned by those of ordinary skill in the art. In the depicted embodiment, diagnostic signals are emitted and received through the distalmost portion of the disposable sheath 502, here shown as comprising the rigid distal optical element 504. The rigid distal optical element 504 itself may be a hollow cylindrical structure designed to mate with the distal end of the probe 506. The rigid distal optical element 504 may have at its distal end an optical window 514. As described further herein, the optical window 514 may be fabricated in a plurality of shapes and may be provided with additional optical properties.

The probe 506 may terminate proximally with a connector 518 that facilitates attachment of the probe 506 with a coupling 520 that provides an electromagnetic connection between the probe 506 and the main instrument console (not shown) of the diagnostic system. In one embodiment, the connector 518 and the coupling 520 may have both optical and electrical signal terminations and interconnections allowing for a remote data processing unit to be used to analyze the raw data generated and accumulated by the optical probe 506. The remote data processing and analysis units may also be provided with appropriate displays to present graphically the results of diagnostic tests carried out on a patient, and further may be provided with input mechanisms whereby additional data may be entered into the system pertaining, for example, to the unique identification of the particular patient being examined. The data processing facilities of the present invention may furthermore be in communication with remote data sources or databases to provide additional information or data sets to be compared to the data entered into the diagnostic system in real time or with time delay.

The sheath 502 may be provided with a proximal fastener 522 and a distal fastener 524 deployed on each side of the coupling 520 and the connector 518. The fasteners may be elastic bands, or strings within the sheaths, or hook and loop type fasteners (e.g., Velcro™), adhesive tapes or glues, or other mechanisms familiar to ordinary practitioners in the relevant arts.

The rigid distal optical element 504 may be provided with an internal ridge 528 that mates with an appropriate groove 544 channeled on the outer aspect of the distal portion of the probe 506. Mating the internal ridge 528 with the corresponding groove may assure that the sheath 502 is affixed to the probe 506 in a unique direction, thereby aligning an identifying marker 530 on the sheath 502 with a reader (not shown) on the probe. FIG. 19B shows a cross-section of the embodiment depicted in FIG. 19A taken at the level indicated by the line X–X'. In FIG. 19B, an arrangement of the optical probe 548 to the rigid optical distal element 542 of the sheath is shown. In this figure, a tongue 540 is borne on the inner aspect of the rigid optical distal element 542. A groove 544 is borne on the outer aspect of the probe 548. The insertion of the tongue 540 in the groove 544 may align a marker 550 disposed on the inner aspect of the rigid optical distal element 542 with a reader 552 disposed on the outer aspect of the optical probe 548. Other types of aligning arrangements will be readily apparent to those ordinary skilled practitioners in these arts, arrangements whereby a particular alignment of sheath and probe is urged, thereby permitting the alignment of other elements on the sheath with corresponding elements on the probe.

In the depicted embodiment, a marker 530 is shown disposed on the inner aspect of the rigid distal optical element 504 of the sheath 506. It is understood that a variety of markers may be contemplated without departing from the spirit and scope of the claimed invention, and that a variety of sensors or receptors may be disposed upon the probe that are adapted for recognizing the data borne by the marker. In the illustrated embodiment, the marker 530 or the marker 550 is disposed on the edge of the optical window. The markers 530 and 550 may be a serial number or any other marker uniquely identifying the specific sheath used with a unique patient. It is further understood that the markers 530 and 550 and the reader may be disposed upon any convenient segment of the sheath and the probe. In one embodiment, the marker may be placed upon the sleeve so that its data are read into the optical system prior to inserting the optical probe within the sleeve. In another embodiment, the marker and the reader may each be positioned on the lateral aspect of the sheath and the probe respectively. In another embodiment, the side of the probe may be equipped with an infrared light emitting diode and an infrared sensor and reflection from a series of lines printed on the side of the sleeve (such as a bar code system of marking), which are read by the sensor to identify the specific sleeve's serial number. A variety of bar code based markers and reader systems may be used, as will be appreciated by artisans of ordinary skill in the relevant arts.

In operation, the markers 530 and 550 may be used to identify the patient on whom the measurement was taken. This specific identification number may be permanently stored in the optical system main console as a number which if seen again by the probe, will prohibit, or lock out the probe functions. Alternatively, the data on the marker may be associated in a database with data identifying the unique patient, so that the probe bearing that marker may only be used with that particular patient. In another embodiment, the reader may affect the state of the data encoded on the marker so that the data are not readable subsequently. If a probe reads a set of data from a sheath marker before the probe may be used, the probe may then each time be placed in contact with a fresh sheath whose data are available for reading. The marker 530 on the sheath 508 may be read before the use of the optical probe 508 and before the probe system 500 may be positioned in contact with a patient's tissue. This may be accomplished, for instance by requiring the probe to be armed as "ready" for use in the patient prior to each measurement. In order to arm the probe and make the probe ready for use, the operator mounts the sheath upon the probe in the correct position and the probe then interrogates the marker on the probe to compare the identifying data contained therein with a database consisting of all previously used identity numbers, to verify that the number is indeed an unused number. If the probe system 500 determines that the marker 530 on the sheath 506 bears previously unread data, corresponding to a previously unused state, the probe may be armed and be thereupon made ready for use. This ready state of the probe may also depend upon the readiness of other system parameters as well. A display integral with the controls of the system may then show the cause for "unreadiness" of the probe. Conditions causing unreadiness of the probe may include previous use of a sheath, absence of a sheath, malposition of a sheath, mechanical problems with a sheath or any other condition of the probe system 500 deemed to interfere with its safe and effective use in the diagnosis of a patient. The probe system 500 may include conventional circuits to permit self-testing and self-diagnosing to ascertain the readiness of various components and functions necessary for safe and effective accomplishment of the diagnostic intervention. In another embodiment, in lieu of markings that are optically read as described above, an RFID (radio frequency identification device) chip may embedded in each disposable sheath, to be read by an appropriate transponder in the optical head. It should be clear that other active semiconductor devices (typically powered by the probing or querying beam from the transponder) may be used in this manner as well. Furthermore, passive electromagnetically read patterns providing coding are feasible as well and are included within the scope of the present invention.

A marker on a sheath may also convey information to the probe about the kind of use for which the sheath is intended. The kind of sheath employed may be varied depending upon the type of diagnostic information that is desired. For example, the colposcopic probe may operate in three independent modalities, and for each modality, a unique type of disposable sheath is best suited for that function. The term "colposcopic probe" as used herein refers to an optical probe system according to the present invention used for the evaluation of the tissues of the cervix. In a highly precise modality of use, a colposcopic probe may be used by highly trained physicians as a device aiding in standard colposcopy. A sheath employed with the probe as an aid to colposcopy may be adapted for transmitting both natural images of the relevant anatomy and signals according to these systems and methods indicating the presence or absence of particular cervical pathologies. The sheath may be adapted to the optimal performance of these functions. The marker on the sheath may convey to the probe information about the nature of the particular intended use of the probe. Upon receiving this information, the probe may adjust for performing the necessary functions.

In a different modality of use, a colposcopic probe may be used to carry out "ASCUS Triage." ASCUS is an acronym understood in the art to stand for "Atypical Squamous Cells of Undetermined Significance". In performing ASCUS triage, image generation of the cervix is a less important function for the probe and thus another type of disposable sheath would be used. The marker on the sheath may inform the probe of the type of test, here ASCUS triage, to be carried out so that the probe may be adjusted or calibrated (typically automatically) for this specific function.

In a different modality of use, the probe may be employed as a adjunct to the current "Pap Smear" test, intended to examine the patient's cervix for cellular abnormalities that may require subsequent detailed analysis, but not intended to provide a diagnosis of the abnormalities detected. This use for the probe may be a binary "pass/no pass" test, or a "yes/no" test, typically carried on by personnel with relatively little medical training. This use modality of the colposcopic probe may allow for screening large populations of subjects; only those returning a result of "yes" or "no pass" are directed to subsequent more detailed examination by highly trained personnel. Here as well, a sheath adapted for this screening function may bear a marker with data "informing" the colposcopic probe of the specific function ("screening") that is going to be carried out, so that the probe may be adjusted for that specific purpose.

In this example, the coding marker of the sheath may identify the test for which the sheath is intended and may communicate with the probe to ensure that its settings are compatible with the intended function. If the sheath is used for an unintended purpose, the interaction of the marker and the reader may interfere with the activation of the probe, as described above. A marker may simultaneously bear additional information about the specific sheath, so that a single use for the sheath may be ensured, as previously described.

Figure 20A:
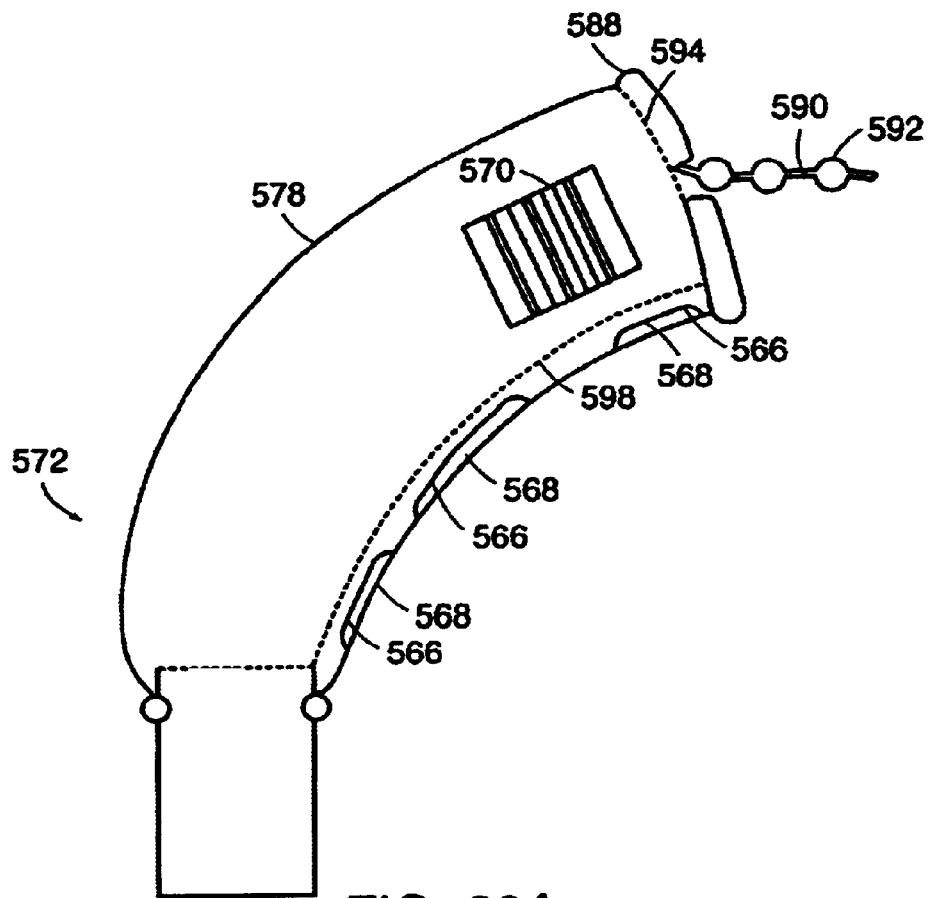
FIG. 20A shows an embodiment of a disposable sheath disposed to cover an optical probe.

FIG. 20A shows a lateral view of an embodiment of a disposable sheath illustrating certain features. In this illustration a coded area 570 is shown as part of a sheath apparatus 572. In certain embodiments, the coded area may be a bar code borne on the inner aspect of the flexible sheath. Other arrangements may be envisioned whereby the coded area 570 would be incorporated in the structure of a sheath 578 itself, or displayed in any other way to make it accessible to a sensor apparatus (not shown) of the probe. In yet another embodiment, only a sensor is used and the reading is accomplished by detecting changes in ambient light reaching the sensor as the sleeve is passed over the side of the probe, and the coded area 570 imparts such light modulation then translated into a unique identifier of the specific sheath used.

Figure 20B:
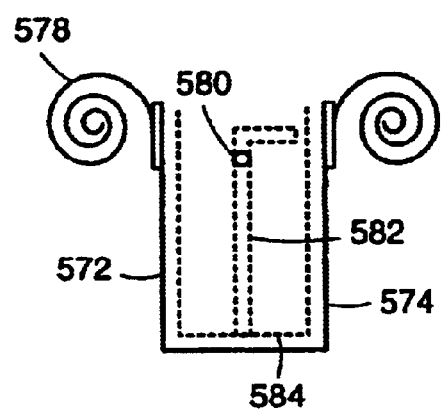
FIG. 20B shows an embodiment of a disposable sheath in a furled position.

FIG. 20B depicts an embodiment where the sheath apparatus 572 includes a flexible sheath 578 to which a residual stress curl has been imparted, so that the flexible sheath 578 may be packaged in the form of a toroid. FIG. 20B further illustrates an embodiment where the rigid distal element 574 is attached to the flexible sheath 578, and the flexible sheath 578 may be uncurled to cover the probe (not shown). In this embodiment, the rigid distal element 574 is first adjusted on the distal end 584 of the optical probe, using, for instance, two or more indexing pins 580 which fit into grooves 582 shown with dashed lines in the illustration. The grooves 582 may also serve to fasten the rigid distal element 574 to the distal end 584 of the optical probe in a bayonet like fashion. After the elements are secured, the curled sleeve 578 may be rolled back over the probe. At the conclusion of the procedure, the sleeve 578 may be rolled back to its original toroidal shape, assuring that no external surface of the sleeve comes in contact with the surface of the probe. The indexing grooves 582 and mating pins 580 also ensure the alignment of the optical path of the sheath with that of the probe. This arrangement may further align the optical path of the sheath with that of the probe, and may serve to align a marker on the sheath with a sensor on the probe as previously described.

In another embodiment, shown in FIG. 20A, the flexible sheath 578, initially packaged in a rolled-up state to be unrolled over the probe, may be provided at its proximal end with a hollow termination 588 within which a string 590 is positioned. After deployment of the sheath 578 onto the optical probe, the string 590 may be pulled tight, to close the proximal end of the sheath and thereby to ensure that the sheath apparatus 572 does not become detached from the optical probe during the procedure. In a variant of this embodiment, the string 590 may be provided with periodic protrusions or beads 592 that act as ratchets or locks that hold the cinched purse-string in position. In another variant of this embodiment, the distal edge of the hollow termination 588 may be either perforated or weakened along a line of weakness 594. According to this embodiment, the string 590 is pulled in the direction of its axis to close the proximal end of the sheath 578, but after the procedure is completed the string 590 is pulled strongly in a direction perpendicular to its axis, thus causing breakage and release of the proximal hollow termination, permitting the sheath 578 to be rolled distally over the probe. In this embodiment, the string 590 may be fastened to one end of the hollow termination 588 so that pulling and breaking the string 590 through the hollow termination 588 both breaks the hollow termination 588 and provides a point from which the sheath 578 may be pulled off the probe without contaminating the probe's external surface.

FIG. 20A further shows that the disposable sheath apparatus 572 is suitable for an optical colposcopic probe wherein the sheath 578 may be attached to the probe by one or more mating elements 568 that may fit within one or more grooves 566 on the probe. According to one embodiment of these systems and methods, the sheath may be pulled over the probe in a manner whereby one or more mating elements 568 disposed on the inner aspect of the sheath 578 may be aligned over a matching set of grooves 566 on the outer aspect of the probe. The user thereupon exerts external pressure upon the mating element 568 to press fit it into the corresponding groove 566. At the end of the procedure, the mating element 568 is disengaged so that the sheath may be removed and discarded. In some embodiments, the cross section of the mating element 568 may be made asymmetric so that pulling it out of its groove causes the sheath 578 to tear on the weaker side of the mating element along a tear line 598. This would permit easier removal of the sheath and would further ensure that no reuse of the disposable sheath would occur.

In FIG. 21A–F are shown various projections of a an embodiment of an optical probe, 600, and in particular, an embodiment adapted for use in examining the cervix uteri. Features of an embodiment of an optical probe adapted for this use have been disclosed elsewhere herein.

Specifically, FIG. 21 A is a posterior view of an optical probe system 600 showing the probe handle 604 with a switch 610 visible distally along the handle 604 and with a connector assembly 608 deployed at the proximal end of the handle. It is understood that the handle 604 may be designed ergonomically to permit secure grasping by the operator, and it may further be adapted for the anatomic region being examined. The handle 604 may also bear within it or on its surface components of the optical probe system 600 related to the specific diagnostic functions of the probe system 600 itself.

FIG. 21 B shows a lateral view of the optical probe system 600 showing the angulation 624 of the device distal to the handle 604 to facilitate anatomic access of the distal optical head 602 to the cervix. In this figure, the optical probe itself is covered by a tightly adherent sheath 618 shown to be cut away before providing coverage for the distal optical head 602 of the probe 600. In the illustrated embodiment, an affixation mechanism 612 is shown on the probe, comprising a protrusion and a groove into which the protrusion may be inserted. In one embodiment, the protrusion may be provided on the inner aspect of the sheath 618 while the groove is provided on the outer aspect of the probe; the opposite arrangement is also possible. Either arrangement of groove and protrusion may comprise an affixation mechanism 612 that permits the alignment of the sheath 618 on the probe in a particular predetermined orientation.

FIG. 21C shows in more detail a switch 610 here shown to be located on the posterior aspect of the optical probe system 600 at the angulation of the device. The position of the switch 610 is selected for ease of use by the operator and may assume any appropriate position on the device. The presence of a switch 610 is optional, and other mechanisms for operating the optical probe system 600 may be envisioned by those of ordinary skill in these arts. Without being limiting, examples for such a switching mechanism may include a floor switch or a voice activation system.

FIG. 21D shows a cross section of the probe handle 604 taken along the line X–X', illustrating the oval shape 620 of the handle 604 in the depicted embodiment. This oval shape 620 has the advantage of facilitating handling of the device and rendering more consistent the orientation of the probe with respect to the cervix.

FIG. 21E shows a top view of an embodiment of an optical probe system 600. This figure depicts the body 622 of the probe distal to the angulation (not shown), with the distal optical head 602 located distal thereto. A switch 610 is positioned on the body 622 for convenient operator access.

FIG. 21F shows an anterior view of an embodiment of an optical probe system 600, providing an anterior view of the distal optical head 602. From this perspective, a ring of optical fibers 628 may be seen disposed along the circumference of the distal optical head. The ring of optical fibers 628 is operably connected in certain embodiments to structures of the disposable sheath (not shown) to permit the transmission of light from the ring of optical fibers 628 through the disposable sheath to reach the tissues of the patient being examined. This figure further depicts an affixation system 614 here shown as a linear arrangement disposed along the anterior aspect of the probe handle 604. It is understood that a plurality of other affixation systems are encompassed as embodiments of the claimed invention, and certain of these systems may be readily envisioned by those of ordinary skill in the art.

Figure 22:
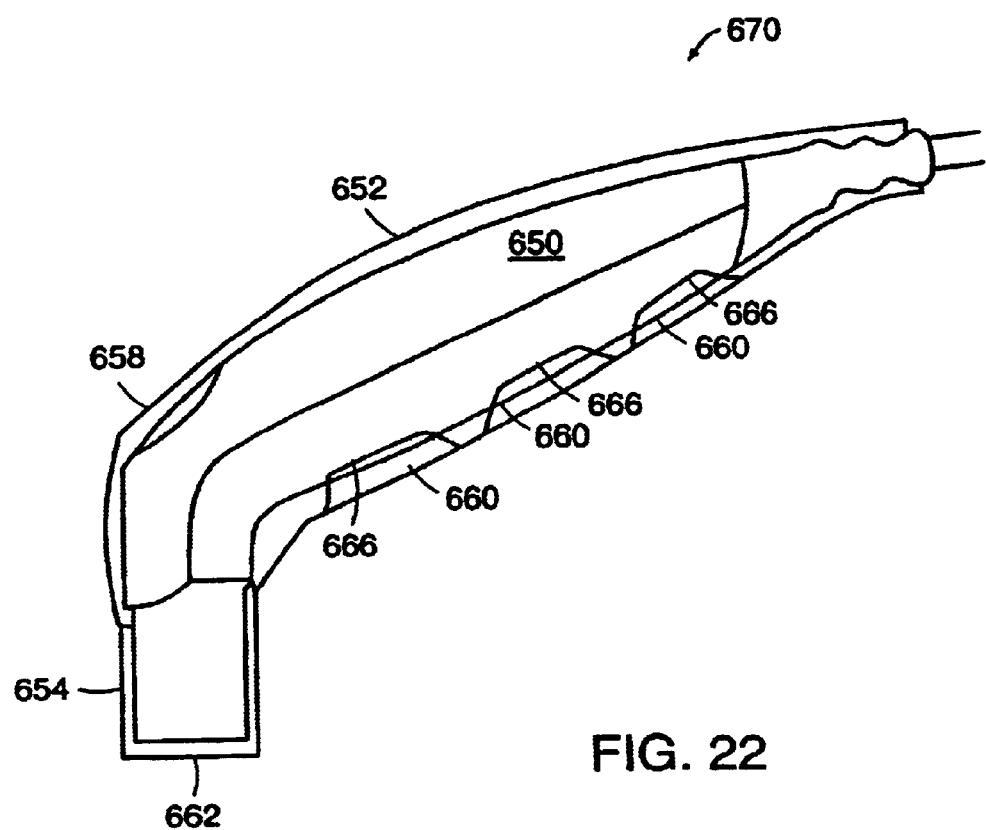
FIG. 22 shows schematically an embodiment of an optical probe covered with a disposable sheath.

In FIG. 22, an embodiment of an optical probe system 670 is shown schematically. The system includes an optical probe 650 and a protective sheath 652. In the depicted embodiment, the protective sheath 652 may be formed as a composite of two elements, a frontal optical quality element 654 and a thin flexible sleeve 658. In certain embodiments, the protective sheath 652 is disposable and is intended for a single use. Various mechanisms of attachment between the sheath 652 and the probe 650 are contemplated by the systems and methods disclosed herein. For example, in one embodiment, the flexible sleeve 658 may be provided with a series of internal protrusions 660 that may be press fit into corresponding slots 666 on the probe 650. Other mechanisms of attachment may be envisioned by practitioners of ordinary skill in the relevant arts. The optical quality element 654 may bear at its distal end a window 662. The optical quality element 654 may bear an affixation mechanism for securing it relative to the distal end of the probe 650. In certain embodiments the window 662 may be flat. In other embodiments, the window 662 may be shaped to act as an active optical component integral to the optics of the optical probe system 670. In yet other embodiments, the window 662 or the optical quality element 654 may be segmented so that a portion of the structure is flat (and thus optically passive) while other portions may be curved, forming, for example, lens segments. Such embodiments may permit various segments to perform different optical functions as part of an overall optical probe system 670. In certain embodiments, the distal optical quality element 654 may be shaped as a hollow cylinder that mates with a comparably structured optical head of the probe. It is desirable for the distal part of the probe and the optical quality element 654 of the sheath 652 to be similarly shaped so that a close fit between the two may be achieved. The shape of these structures in cross-section may be cylindrical, oval or any shape adapted to carrying out the functions of the optical probe system 670 or adapted to carrying out a diagnostic evaluation of a particular anatomic site. The optical quality element 652 may be molded or cast from an optical plastic, such as PMMA, polystyrene or polycarbonate. These materials may be used to form the window 662 while other materials are used to form the optical quality element 652. PMMA is a particularly advantageous material for these constructions because it has minimal fluorescence response when illuminated with the UW excitation beam.

FIG. 23A–D show cross-sectional diagrams of embodiments of attachments by which a flexible part of a protective sheath may be affixed to a rigid distal part.

Figure 23A:
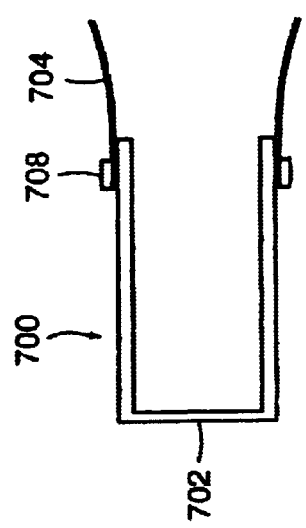
FIG. 23A–D show embodiments of attachment mechanisms affixing a flexible portion of a protective sheath to a distal rigid portion.

FIG. 23A shows an end piece 700 of a protective sheath configured as a hollow structure closed at its distal end with a distal optical window 702. A thin flexible sheath 704 is shown fastened to the external part of the proximal end of the end piece 700 by a fastening ring 708 that is disposed circumferentially around the end piece 700. This fastening ring.708 may be "press fit" onto the proximal end locking the flexible sheath 704 between it and the end piece 700. Other arrangements may also be envisioned. For example, a thin threaded area may be provided on the inner side of the fastening ring 708 that mates with an opposing thread on the end piece 700, locking an edge of the flexible sheath 704 therebetween.

Figure 23B:
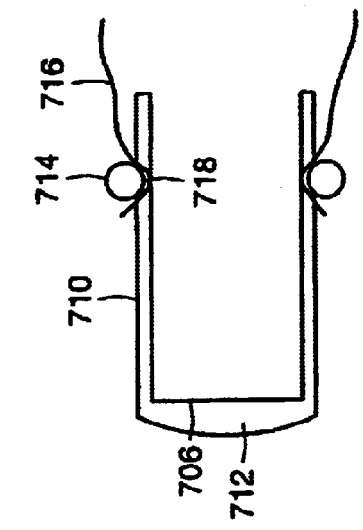

FIG. 23B shows another embodiment of an optical end piece 710 terminated with a lens structure 712 bearing an inner flat surface 706. The illustrated optical end piece 710 is configured as a hollow structure shaped to mate with the distal end of the optical probe. In this embodiment the fastening of the of the flexible sheath 716 to the optical end piece 710 is achieved with a toroidal ring 714 that is adapted to fit within a circular concavity 718 around the circumference of the exterior aspect of the optical end piece 710, capturing the edge of the flexible sheath 716 therebetween.

Figure 23C:
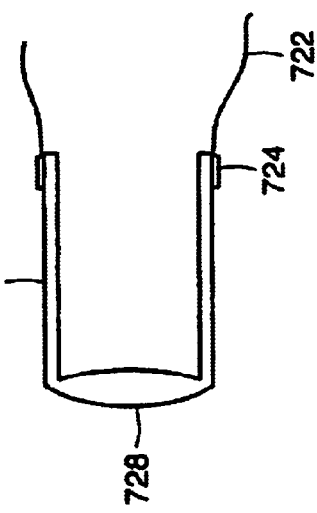

FIG. 23C shows an embodiment of the sheath system in which a rigid optical element 720 is fastened to a flexible sheath 722 with an appropriate adhesive 724. An appropriate adhesive may comprise various chemical compositions, for example, any of a variety of cyano-acrylate compounds that are biocompatible. Other adhesive compounds may be envisioned by practitioners in the relevant arts. This figure further shows a lens 728 that may serve as the objective for the optical probe.

Figure 23D:
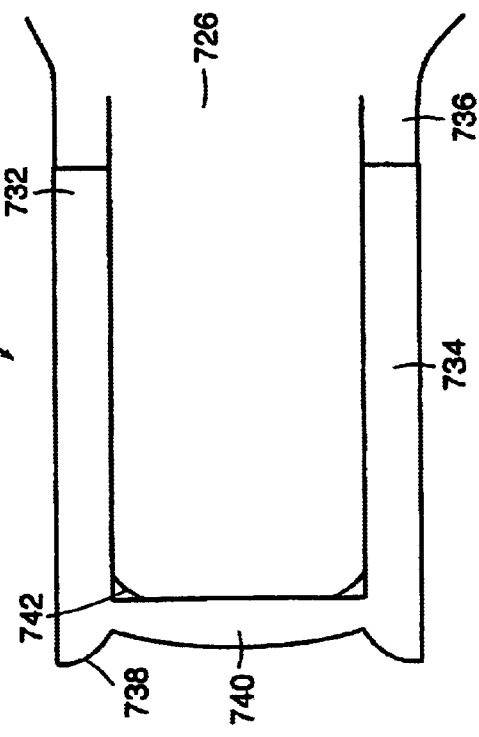

FIG. 23D shows a cross-sectional view of another embodiment of the distal end of the disposable sheath of the present invention. In this embodiment, the optical probe 726 is provided with illuminating fibers 736 arranged circumferentially and abutting the circular proximal end 732 of the distal optical element 730 of the disposable sheath system. The bundle of illuminating fibers 736 may be arranged in a ring within the optical probe 726 to emerge and terminate at a correlative area of the optical element 730 of the disposable sheath system. In one embodiment, the illuminating fibers 736 may terminate at a circumferential structure on the distal optical element 730 where the proximal flexible portion (not shown) of the disposable sheath system is affixed to the distal optical element 730. In one embodiment, the wall thickness of the distal optical element 730 may be fairly thick (between 0.5 mm and 2.0 mm), so that a wall 734 is formed that may act as an optical waveguide to transmit light emitted from the illuminating fibers 736 to the distal end of the distal optical element 730. The wall 734 of the distal optical element 730 ends as a toroidal segment 738 of an optical waveguide which acts to direct the light onto the target tissues for better visualization. FIG. 23D shows a configuration adapted for the evaluation of the cervix, although other shapes may be envisioned that would usefully conform to various other anatomical regions. The end piece 740 of the distal optical element 730 may be shaped to achieve various optical purposes, for example, acting as an objective for the probe's optical assembly. In the depicted embodiment, a space 742 is shown that may contain a bead or other delivery apparatus for dispensing a fluid. The fluid is released by the mating of the distal part of the probe with the distal optical element 730 of the sheath system. The fluid may flow between the distal part of the probe and the inner aspect of the distal optical element 730. In one embodiment, the fluid may have an index of refraction matching that of the elements in the probe and the end piece 740. In one embodiment, this space 742 may occupy the top half of the inner distal circumference of the distal optical element 730. A bead or other container residing in the space 742 may be caused to to break and discharge its fluid, which then spread downward by capillary forces to fill the space between the inner aspect of the end piece 740 and the distal end of the optical probe. Other dispensation systems for a fluid may be readily envisioned. The presence of a fluid between these two components may serve a variety of optical functions, for example, reducing sharply any reflections from the surfaces of the end piece 740. Other functions for the fluid may be envisioned by ordinary practitioners in these arts. One advantage of delivering a fluid to flow between the optical prove and the distal optical element is the prevention of reuse of the disposable sheath, because the fluid necessary for the proper functioning of the optical probe system is discharged from its reservoir upon the mating of a probe with a sheath, and the fluid may therefore only be used once, with the mating of a specific sheath with the probe.

Figure 24:
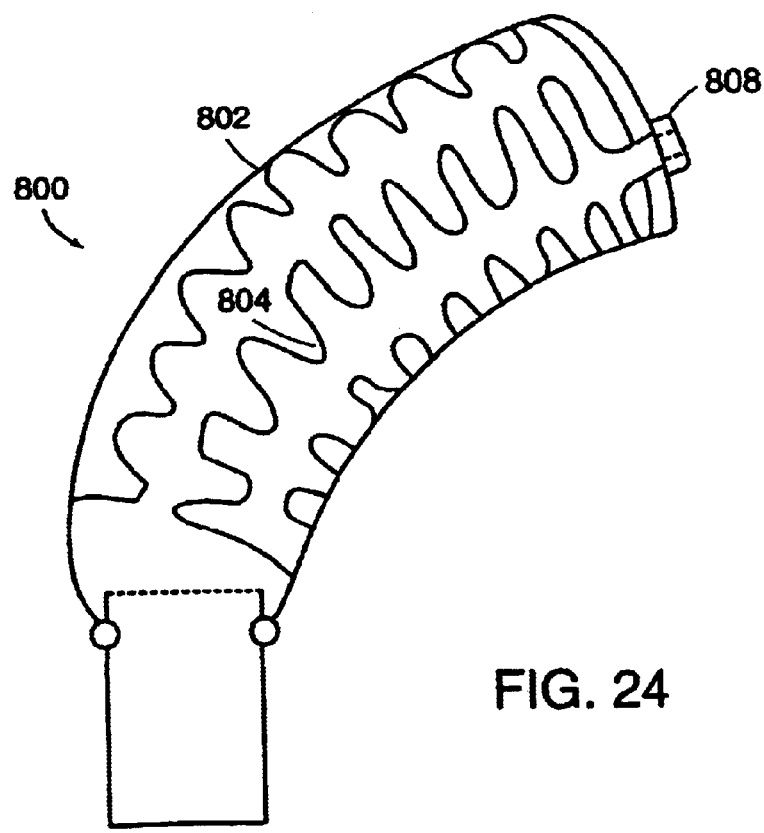
FIG. 24 shows an embodiment of a protective sheath adapted for application by heat shrinking.

FIG. 24 depicts an embodiment of a disposable sheath 800 provided with a flexible heat shrinkable sleeve 802. In one embodiment, the shrinkable sleeve 802 may be treated with a heat source such as a hair drier after being placed upon an optical probe, thereby to shrink it. In another embodiment, a resistor pattern 804 may be placed on the disposable sheath 800, for example by silk screening. With a resistor pattern in place, the sheath 800 may be treated by passing a current into a connector 808 for a short period of time, thereby heating the sheath 800 and causing its shrinkage. Shrink-fitting the sheath 800 to the probe after positioning it thereupon may stabilize the sheath with respect to the underlying probe. In this way, any necessary alignments between the sheath 800 and the probe may be established and maintained. Shrink-fitting may also require a tearing or other destruction of the sheath 800 to remove it from the probe at the end of a procedure. A sheath 800 destructively removed may subsequently be unusable.

Figure 25A:
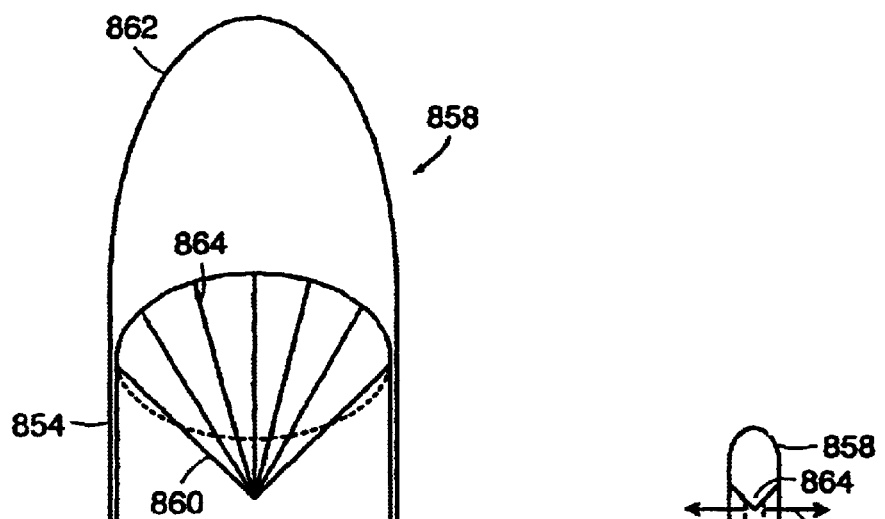
FIG. 25 A and B show, respectively, an embodiment of a tip of a probe system adapted for examination of the endocervix, and an embodiment of a probe system adapted for examination of the endocervix.
Figure 25B:
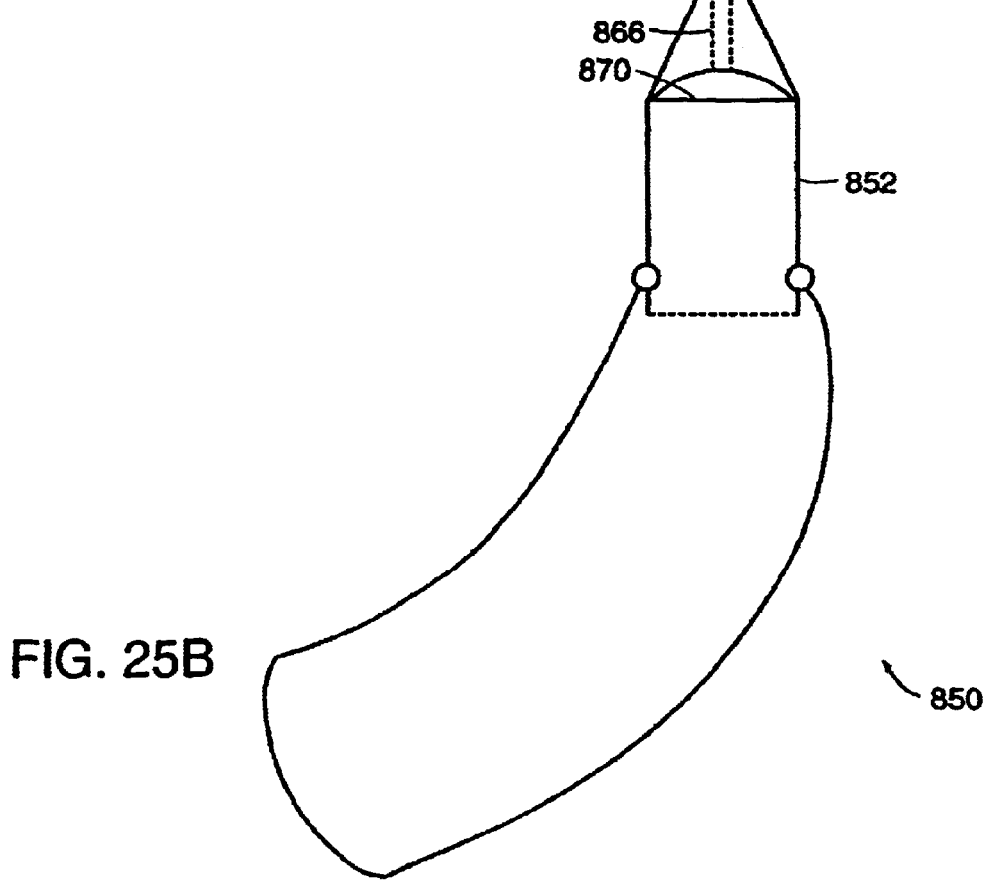

In FIG. 25A is shown yet another embodiment of a disposable sheath 850 according to the present invention. This embodiment provides a configuration of its distal optical element 852 adapted for evaluating pathologies of the endocervix. It is understood that, since the cervical os is typically closed, examination of its inner wall is not possible with direct surface viewing. The illustrated embodiment provides an optical extension 854 for the distal optical element 852, said optical extension being adapted for penetrating into the endocervix to permit the acquisition of diagnostic data for the tissues lining the endocervix. The optical extension 854 terminates in a distal tip 858 comprising a tapered end capable of penetrating the usually closed cervical os and further comprising an optical system adapted for visualization of the lateral endocervical walls. Certain structures in the optical extension 854 are shown in more detail in FIG. 25B. FIG. 25B shows the distal tip 858 of the optical extension with its distalmost tapered end 862. An optical system 860 within the distal tip 858 comprises a faceted and mirrored cone 864. The cone 864 has a half angle of 45 degrees. Thus a light beam 866, as shown in FIG. 25A, impinging on one of the facets of the cone 864 is reflected at a 90 degree angle to the incident light and is thus emitted laterally from the distal tip 858, as shown by the arrows at 868. In one embodiment, the number of facets on the faceted cone 864 corresponds to the number of excitation fibers used for the procedure, a number that typically is less than the number of fibers used for examining the entire surface of the cervix. It may be desirable to add an additional objective 870 to focus the excitation light beams 866 appropriately on the optical system 860 of the optical extension 854. Furthermore, without departing from the scope of the disclosed invention, skilled practitioners in the relevant arts may readily envision other optical systems for directing the illuminating light to the endocervical tissues and for collecting the light emanating therefrom.

In one method of operation according to these systems and methods, the disposable sheath 850 may be mounted on an optical probe adapted for examination of the cervix uteri. If a disposable sheath 850 is selected that is adapted for endocervical examinations, a marker (not shown) on that sheath 850 may be read by the optical probe. Data from that marker may be input into the probe system, operating to activate a selected number of excitation fibers (not shown). In one embodiment, the activated fibers may provide UV light for excitation. In one embodiment, the excitation fibers may be activated sequentially, or may be activated as "opposing pairs" to assure that fluorescence responses from different spots on the wall of the endocervix are not interfering with each other. Optical responses from the illuminated tissues may be collected along the same optical path traced by the excitation beams, except that the responses are much broader (in essence lambertian in nature). In this embodiment, the collection optics for the response may be separate from the excitation optics, or may be part of the same apparatus as the excitation optics. When spatial discrimination of an endocervical lesion is less important, the mirrored cone 864 may be a simple conical structure without facets.

Those skilled in the art will know or be able to ascertain using no more than routine experimentation, many equivalents to the embodiments and practices described herein. For example, the systems and methods described herein may be employed with probes being disposed in body canals, blood vessels, ducts and other body passages. Additionally, both the probe and sheath may have shapes other than those shown in the depicted embodiments, and may be made of any suitable materials. Further, other embodiments may be realized, wherein the sheath may be formed from one or more than one components adapted to the optical functions of the probe and the anatomic location where it will be used. Other shapes of the sheath may be envisioned that fit the probe appropriately. A number of mechanisms may be constructed which lend themselves to limiting sheath use to a single use, some of which have been illustrated herein. Other mechanisms for ensuring a single use of the sheath may include affixation mechanisms, marker and reader mechanisms, fluid dispensing mechanisms, tearing and breaking mechanisms and other mechanisms adapted for this purpose. Such mechanisms will be familiar to those of ordinary skill in the relevant arts.

Furthermore, it is understood that the systems and methods of the present invention may collect data or may relate to data pertaining to the examination procedure itself The system according to the present invention may measure and record information about the duration of the procedure, the amount of energy or other consumable supplies utilized to perform the procedure, the number of measurements taken during the procedure, or any other features of the procedure of significance. alternatively, the systems and methods of the present invention may interface with a database wherein such data are stored. In one embodiment, the procedure and its duration may be tallied and correlated with patient information so that an appropriate bill for the service may be constructed. Billing information may be entered into a database that can then be accessed by the system to produce a bill for the particular procedure. In certain embodiments, the billing information may include a diagnostic or a procedural code for categorizing the procedure so that a bill bearing this information may be generated that will then be associated with a schedule of predetermined fees. Diagnosis according to ICD-9 codes and procedural terminology according to CPT codes are well-known in the art. Other codes or categories may be used for organizing a patient's billing information, so that each procedure according to these systems and methods will generate an accurate bill. Billing information may differ from one patient to the next according to the fee schedules for various managed care organizations and third-party payors. In one embodiment, the systems and methods of the present information may comprise the entry of billing information for a particular patient into a database. The billing information may then be correlated with data about the procedure itself or with data about the diagnosis produced in order to generate an accurate bill.

Although the embodiments described herein relate to the application of these systems and methods to the diagnosis and treatment of medical conditions and to the delivery of health care services, it is understood that these systems and methods may be directed to the examination of any target, and that these systems and methods may furthermore be correlated with systems for recording data that identifies characteristics of the target so that outcomes of the examination may be usefully stored in relation to other data pertaining to the target.

Accordingly, it will be understood that the invention may be realized by many different systems that include a barrier or a sheath, and is not to be limited to the embodiments disclosed herein, but is to be understood from the following claims, which are to be interpreted as broadly as allowed under the law.

What is claimed is:

1. Apparatus for determining a characteristic of a sample of biological material, comprising:

a probe having an optical assembly that sequentially directs a first set of electromagnetic radiation to a plurality of locations in a sample with an intensity distribution in the sample that drops off substantially monotonically from a first region in a first optical path and that receives a response indicative of a second set of electromagnetic radiation, said second set comprising electromagnetic radiation emanating from each of said locations, said optical assembly collecting said second set of electromagnetic radiation with a collection distribution that drops off substantially monotonically from a second region in a second optical path, said first and second regions at least partially overlapping in each of said locations, said optical assembly comprising at least one array of field stops whose dimensions are large compared to a quotient of wavelength of said electromagnetic radiation divided by a working numerical aperture of said optical assembly, measured from said field stops;

a detector coupled to said received response to produce signals that vary according to said characteristic in each of said locations;

a processor that processes signals produced by the detector to determine the characteristic of the sample; and a sheath that covers the probe.

2. The apparatus of claim 1 wherein the probe comprises at least one pin and the sheath comprises at least one region corresponding to the at least one pin of the probe.

3. apparatus according to claim 2, wherein the optical assembly is inoperative in the absence of the sheath.

4. The apparatus according to claim 2, wherein the sample of biological material exists in continuity with an in-vivo body tissue.

5. The apparatus according to claim 4, wherein the sheath prevents the probe from contacting the in-vivo body tissue.

6. The apparatus according to claim 4, wherein the sheath prevents the probe from contacting a tissue in proximity to the in-vivo body tissue.

7. The apparatus according to claim 4, wherein the sheath is for a single use.

8. The apparatus according to claim 7, wherein the sheath is for positioning upon the probe in a unique position.

9. The apparatus according to claim 7, wherein the sheath is attached to the probe, and wherein a detachment of the sheath from the probe renders the sheath inoperable.

10. The apparatus according to claim 7, wherein the sheath further comprises a marker bearing data identifying the sheath, and wherein the probe further comprises a reader to read the data on the marker, and a processing system to correlate the data on the marker with an indicator that relates to an unused state of the sheath.

11. The apparatus according to claim 7, wherein the sheath further comprises a marker bearing data identifying the sheath, and wherein the probe further comprises a reader to read the data on the marker, and an indicator that relates to a previously used state of the sheath.

12. The apparatus according to claim 7, further comprising a refractive index matching fluid.

13. The apparatus according to claim 2, wherein the sheath comprises a window for transmitting electromagnetic radiation.

14. The apparatus according to claim 13, wherein the window is capable of transmitting electromagnetic radiation without producing significant fluorescent response.

* * * * *